United States Patent
Kanda et al.

(10) Patent No.: US 6,492,392 B1
(45) Date of Patent: Dec. 10, 2002

(54) 2-PIPERIDONE COMPOUNDS

(75) Inventors: Yutaka Kanda, Tokyo (JP); Rieko Tanaka, Shizuoka (JP); Mitsunobu Hara, Shizuoka (JP); Jun Eishima, Shizuoka (JP); Shiro Akinaga, Shizuoka (JP); Tadashi Ashizawa, Shizuoka (JP)

(73) Assignees: Kyowa Hakko Kogyo Co., Ltd., Tokyo (JP); Eli Lilly & Co., Indianapolis, IN (US)

( * ) Notice: Subject to any disclaimer, the term of this patent is extended or adjusted under 35 U.S.C. 154(b) by 0 days.

(21) Appl. No.: 09/481,542

(22) Filed: Jan. 12, 2000

Related U.S. Application Data
(60) Provisional application No. 60/115,522, filed on Jan. 12, 1999.

(51) Int. Cl.$^7$ .................... A61K 31/445; C07D 213/02; C07D 211/40; C07D 211/56; C07D 401/00
(52) U.S. Cl. ................ 514/317; 514/318; 514/326; 514/327; 546/194; 546/207; 546/216; 546/223
(58) Field of Search ................ 546/194, 207, 546/216, 223; 514/317, 318, 326, 327

(56) References Cited

U.S. PATENT DOCUMENTS
5,232,929 A  8/1993  Desai et al. ................ 514/314

OTHER PUBLICATIONS
Chem. abstr. vol. 122, No. 49649, (1994), Pascaal et al, "N-(Pyrid-3-yl) thioares & derivatives as acarcides".*
Chem Abstr vol. 117, No. 7780, (1992), Pascal et al, "Nucleophilic displacement reactions on sterically hindered chloropyridenes".*

* cited by examiner

*Primary Examiner*—Alan L. Rotman
*Assistant Examiner*—Raymond Covington
(74) *Attorney, Agent, or Firm*—Fitzpatrick, Cella, Harper & Scinto

(57) ABSTRACT

The present invention provides 2-piperidone compounds or pharmaceutically acceptable salts thereof, which have a potent activity of inhibiting the proliferation of tumor cells and thus are useful as medicaments, as well as antitumor agents containing these compounds. The 2-piperidone compound is represented by the following formula (I):

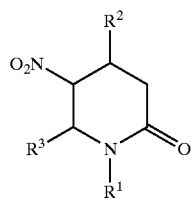

(I)

wherein $R^1$ represents —$(CH_2)_n R^{1a}$ {wherein n is an integer of from 0 to 5, and $R^{1a}$ represents amino, lower alkylamino, di(lower alkyl)amino, substituted or unsubstituted aryl, or a substituted or unsubstituted heterocyclic group}, and $R^2$ and $R^3$ independently represent lower alkyl which may be substituted by lower alkoxycarboyl; lower alkenyl, aralkyl or lower alkynyl which may be substituted by substituted or unsubstituted aryl or a substituted or unsubstituted heterocyclic group; substituted or unsubstituted aryl; or a substituted or unsubstituted heterocyclic group.

9 Claims, No Drawings

2-PIPERIDONE COMPOUNDS

This application claims the benefit of Ser. No. 60/115,522, filed Jan. 12, 1999.

TECHNICAL FIELD

This invention relates to a pharmaceutical composition comprising as an active ingredient a 2-piperidone compound which has antitumor activity and is useful as a medicament such as an antitumor agent.

BACKGROUND ART

Although studies have been widely made on antitumor agents efficacious on solid tumors, there are only few antitumor agents having low toxicity. The present inventors investigated antitumor agents efficacious on solid tumors and, as a result, found that certain 2-piperidone compounds are efficacious on solid tumors while showing low toxicity, thus completing the present invention.

4,6-Diphenyl-5-nitro-2-piperidone has been known as an intermediate for the synthesis of 3-aminopiperidine derivatives (U.S. Pat. No. 5,232,929). However, no pharmacological activity of this compound has been known. Also, 5-nitro-6-phenyl-1-(2-phenylethyl)-2-piperidone has been known (*Synthesis*, 615–616 (1976)) but its pharmacological activity is also unknown.

DISCLOSURE OF THE INVENTION

An object of the present invention is to provide 2-piperidone compounds which have an activity of inhibiting the proliferation of solid tumor cells and are useful as excellent antitumor agents.

The present invention relates to a 2-piperidone compound represented by the following formula (I) or a pharmaceutically acceptable salt thereof:

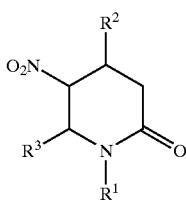

(I)

wherein $R^1$ represents —$(CH_2)_n R^{1a}$ {wherein n is an integer of from 0 to 5, and $R^{1a}$ represents amino, lower alkylamino, di(lower alkyl)amino, substituted or unsubstituted aryl, or a substituted or unsubstituted heterocyclic group}, and $R^2$ and $R^3$ independently represent lower alkyl which may be substituted by lower alkoxycarboyl; lower alkenyl, aralkyl or lower alkynyl which may be substituted by substituted or unsubstituted aryl or a substituted or unsubstituted heterocyclic group; substituted or unsubstituted aryl; or a substituted or unsubstituted heterocyclic group. Among the compounds of the formula (I), the compounds wherein $R^{1a}$ represents a substituted or unsubstituted heterocyclic group and $R^2$ and $R^3$ independently represent substituted or unsubstituted aryl or pharmaceutically acceptable salts thereof are preferable, and the compounds wherein $R^{1a}$ represents a heterocyclic group, and $R^2$ and $R^3$ independently represent substituted aryl or pharmaceutically acceptable salts thereof are further preferable. The present invention also relates to a pharmaceutical composition which comprises as an active ingredient the aforementioned 2-piperidone compound or a pharmaceutically acceptable salt thereof. The present invention further relates to an antitumor agent which comprises as an active ingredient the aforementioned 2-piperidone compound or a pharmaceutically acceptable salt thereof.

The present invention further relates to a pharmaceutical composition which comprises the 2-piperidone compound of the formula (I) or a pharmaceutically acceptable salt thereof; an antitumor agent which comprises the 2-piperidone compound of the formula (I) or a pharmaceutically acceptable salt thereof; a method for preventing or treating a patient having tumor, which comprises administering to the patient an effective amount of any one of the 2-piperidone compounds of the formula (I) or a pharmaceutically acceptable salt thereof; and use of any one of the 2-piperidone compounds of the formula (I) or a pharmaceutically acceptable salt thereof for the production of a pharmaceutical composition which is effective in preventing or treating a patient having tumor; use of any one of the 2-piperidone compounds of the formula (I) or a pharmaceutically acceptable salt thereof for the prevention or treatment of a patient having tumor; and a pharmaceutical composition which comprises a pharmaceutically acceptable carrier and an effective amount of any one of the 2-piperidone compounds of the formula (I) or a pharmaceutically acceptable salt thereof in a pharmaceutically acceptable dosage form.

Hereinafter, the compounds represented by the above formula (I) will be referred to as Compounds (I), and the same will apply to compounds represented by other formula numbers.

In the definition of each group given in the formula (I), the term "aryl" stands for a mono- to tricycle of 3- to 7-membered carbon rings wherein at least one of the rings is an aromatic ring. Examples thereof include phenyl, naphthyl, anthracenyl, tetrahydronaphthyl, indanyl and phenanthrenyl.

Examples of the heterocyclic group include azepinyl, benzimidazolyl, benzofurazanyl, benzopyranyl, benzothiopyranyl, benzofuryl, benzothiazolyl, benzothiadiazolyl, benzothienyl, benzoxazolyl, 1,4-benzodioxanyl, chromanyl, cinnolinyl, dihydrobenzofuryl, dihydrobenzothienyl, dihydrobenzothiopyranyl, furyl, imidazolidinyl, imidazolyl, imidazothiazolyl, indolinyl, indolyl, isochromanyl, isoindolyl, 1,3-dioxolanyl, 1,3-dithiolanyl, isoxazolyl, isoquinolyl, isothiazolyl, isothiazolidinyl, morpholinyl, naphthyridinyl, oxadiazolyl, oxazolyl, 2-oxoazepinyl, 2-oxopiperazinyl, 2-oxopyrrolidinyl, piperidyl, piperazinyl, pyridyl, pyridyl N-oxide, pyrazinyl, pyrazolinyl, pyrazolyl, pyrimidinyl, pyrrolidinyl, pyrrolyl, quinazolinyl, quinolinyl, quinoxalinyl, tetrahydrofuryl, tetrahydroisoquinolyl, tetrahydroquinolyl, tetrahydropyranyl, tetrazolyl, thiadiazolyl, thiazolyl, thiazolinyl, thienofuryl, thienothienyl, thienyl, triazolyl and pyridonyl.

Examples of the aralkyl include $C_{7-20}$ aralkyl such as benzyl, phenethyl, benzhydryl, naphthylmethyl and trityl.

The lower alkyl and the lower alkyl moieties in the lower alkylamino, di(lower alkyl)amino and lower alkoxycarbonyl include linear, branched or cyclic $C_{1-10}$ alkyl such as methyl, ethyl, propyl, isopropyl, butyl, isobutyl, sec-butyl, tert-butyl, pentyl, isopentyl, hexyl, heptyl, octyl, nonyl, decyl, cyclopropyl, cyclobutyl, cyclopentyl, cyclohexyl, cycloheptyl, cyclooctyl and adamantyl.

The lower alkenyl includes linear, branched or cyclic $C_{2-10}$ alkenyl such as vinyl, allyl, crotyl, 1-propenyl, prenyl, isopropenyl, 2-methyl-2-butenyl, pentenyl, hexenyl, heptenyl, 2,6-dimethyl-5-heptenyl, cyclobutenyl, cyclopentenyl, and cyclohexenyl.

The lower alkynyl includes linear or branched $C_{2-10}$ alkynyl such as ethynyl, propynyl, butynyl, pentynyl, hexynyl, heptynyl, and octynyl.

Substituents on the aryl or heterocyclic group may be the same or different 1 to 3 substituents, and examples thereof include hydroxy; halogen; nitro; amino; carboxy; lower alkyl optionally substituted by 1 to 3 halogen, lower alkoxycarbonyl or hydroxy; lower alkoxy optionally substituted by 1 to 3 halogen or lower alkoxy; lower alkoxycarbonyl; lower alkylthio; lower alkenyl optionally substituted by 1 to 3 lower alkoxy, lower alkoxycarbonyl or a heterocyclic group; lower alkynyl; aryl optionally substituted by 1 to 3 halogen atoms; aryloxy; aryloxy(lower alkyl); aroyloxy; lower alkylamino optionally substituted by a heterocyclic group; hydroxyamino; formyl; lower alkanoyl; lower alkanoyloxy; amino substituted by lower alkanoyloxy or lower alkanoyl; di(lower alkyl)amino; di(lower alkyl)aminocarbonyloxy; lower alkanoylamino; lower alkylsulfonylamino; lower alkoxycarbonylamino; aralkylamino; sulfamylamino (aminosulfonylamino); ureido (carbamoylamino); cyano; aralkyl; aralkyloxy; arylsulfonyl; a heterocyclic group; a heterocyclic group-carbonyloxy; camphanoyloxy; methylenedioxy; ethylenedioxy; $B(OH)_2$ and $SO_3H$. The term "halogen" stands for fluorine, chlorine, bromine and iodine atoms. The aralkyl and the aralkyl moieties in the aralkylamino and the aralkyloxy are each as defined above. The lower alkyl and the lower alkyl moieties in the lower alkoxy, lower alkoxycarbonyl, aryloxy(lower alkyl), lower alkanoyl, lower alkylthio, lower alkylamino, lower alkanoyloxy, di(lower alkyl)amino, di(lower alkyl)aminocarbonyloxy, lower alkanoylamino, lower alkylsulfonylamino and lower alkoxycarbonylamino are each as defined above. The aryl and the aryl moieties in the aryloxy, aryloxy(lower alkyl), arylsulfonyl and aroyloxy are each as defined above. The heterocyclic group and the heterocyclic group moiety in the heterocyclic group-carbonyloxy are each as defined above. The lower alkenyl and the lower alkynyl are each as defined above.

Examples of the pharmaceutically acceptable salt of Compounds (I) include pharmaceutically acceptable acid addition salts, metal salts, ammonium salts, organic amine addition salts and amino acid addition salts thereof. Examples of the acid addition salt include inorganic acid addition salts such as hydrochlorides, hydrobromides, sulfates, phosphates and nitrates, and organic acid addition salts such as formates, acetates, propionates, benzoates, maleates, fumarates, succinates, tartrates, citrates, oxalates, methanesulfonates, p-toluenesulfonates, aspartates and glutamates. Examples of the metal salt include alkali metal salts such as lithium salts, sodium salts and potassium salts, alkaline earth metal salts such as magnesium salts and calcium salts, aluminum salts, and zinc salts. Examples of the ammonium salt include ammonium salts and tetramethylammonium salts. Examples of the organic amine addition salt include addition salts with morpholine and piperidine. Examples of the amino acid addition salt include addition salts with glycine, phenylalanine, glutamic acid and lysine.

Next, a process for producing Compounds (I) will be explained.

In the following process, when a group defined therein changes under the employed conditions or the group is inappropriate for carrying out the process, the object compound can be obtained by using the method of introducing and eliminating protective group(s) commonly used in the field of synthetic organic chemistry [see, for example, "Protective Groups in Organic Synthesis", T. W. Greene, John Wiley & Sons, Inc. (1981)]. If necessary, the order of the reaction steps of, for example, introducing substituents may be appropriately changed.

Production Process

Compound (I) can be synthesized starting with Compound (II), which are known compounds or which can easily produce by a known process, via Compound (III) by, for example, the following steps.

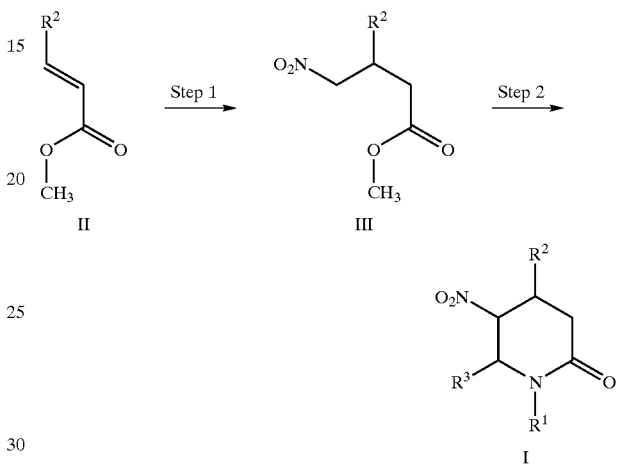

In the formula, $R^1$, $R^2$ and $R^3$ are each as defined above.

(Step 1)

Compound (III) can be synthesized by reacting Compound (II) with 1 to 100 equivalents of nitromethane in an inert solvent (e.g., acetonitrile, dimethylformamide) in the presence of 0.01 to 10 equivalents of a base [e.g., 1,8-diazabicyclo[5.4.0]undec-7-ene (DBU)] in accordance with a method reported in *Synthesis*, 226 (1984). The reaction is usually carried out at −30 to 100° C. and completed within 1 to 72 hours. In this process, nitromethane can be employed also as the solvent.

(Step 2)

Compound (I) can be synthesized by reacting Compound (III) in a solvent (e.g., ethanol, methanol) with Compound (IV) represented by the following formula:

$$R^3\text{—CHO} \qquad (IV)$$

wherein $R^3$ is as defined above;
and Compound (V) represented by the following formula:

$$R^1\text{—NH}_2 \qquad (V)$$

wherein $R^1$ is as defined above. Usually, Compound (IV) and Compound (V) are used each in an amount of 1 to 5 equivalents based upon that of Compound (III). Also, an acid addition salt (e.g., acetate) of Compound (V) can be used instead of Compound (V). The reaction is usually carried out at 0 to 100° C. and completed within 1 to 72 hours.

In the production of Compound (I), the conversion of the functional groups $R^1$, $R^2$ and $R^3$ may be carried out by using a method for converting functional groups commonly employed in synthetic organic chemistry [see, for example, "Comprehensive Organic Transformations", R. C. Larock (1989)].

In the above production process, the product can be isolated and purified by using an appropriately combination of techniques commonly employed in organic synthesis (e.g., filtration, extraction, washing, drying, concentration, crystallization, various types of chromatography).

Some of Compounds (I) can exist in the form of various stereoisomers such as enantiomers or diastereomers. All of the possible isomers and mixtures thereof including the above-mentioned ones fall within the scope of the present invention.

Compounds (I) and their pharmaceutically acceptable salts may exist in the form of adducts with water or various solvents. The above adducts can also be used as the treating agents according to the present invention.

Tables 1 to 6 show the structures and physical data of typical examples of Compound (I).

TABLE 1

Examples of Compound (I) and physical data (1)

(wherein, $R^{2a}$, $R^{2b}$ and $R^{2c}$, and $R^{3a}$, $R^{3b}$ and $R^{3c}$ respectively mean the substituents of the substituted phenyl groups as $R^2$ and $R^3$)

| Compound | $R^{2a}, R^{2b}, R^{2c}$ | $R^{3a}, R^{3b}, R^{3c}$ | FABMS m/z $(M + H)^+$ |
|---|---|---|---|
| 1 | 3-Br | 4-OH | 484, 482 |
| 2 | 3-OCH$_3$ | 4-OH | 434 |
| 3 | 3-OCH$_3$ | 4-OCH$_2$C$_6$H$_5$ | 524 |
| 4 | H | 4-OH | 404 |
| 5 | 3-Br | 3-OH | 484, 482 |
| 6 | 3-Br | 4-CN | 493, 491 |
| 7 | 3-Br | 4-CO$_2$H | 512, 510 |
| 8 | 4-Br | 4-OH | 484, 482 |
| 9 | 3-Br | 3,4-(OH)$_2$ | 500, 498 |
| 10 | 3-COCH$_3$ | 4-OH | 446 |
| 11 | 3-NO$_2$, 4-OCH$_2$OCH$_3$ | 4-OH | 509 |
| 12 | 3-CN | 4-OH | 429 |
| 13 | 2-Br | 3-Br | 548, 546, 544 |
| 14(±) | 2-Br | 4-OH | 484, 482 |
| 15 | 2,3-(Cl)$_2$ | 4-OH | 474, 472 |
| 16 | 3-Cl | 4-OH | 438 |
| 17 | 2,3-(Cl)$_2$ | 2-OH | 474, 472 |
| 18 | 2,3-(Cl)$_2$ | 3-OCH$_3$, 4-OH | 504, 502 |
| 19 | 3-NO$_2$ | 4-OH | 449 |
| 20 | 3-Br | 3,5-(OCH$_3$)$_2$, 4-OH | 544, 542 |
| 21 | 3-CH$_3$ | 4-OH | 418 |
| 22(±) | 2-Br | 3,4-(OH)$_2$ | 500, 498 |
| 23 | 3-Cl | 3,4-(OH)$_2$ | 454 |
| 24 | 3-NHOH | 4-OH | 435 |
| 25 | 3-Br | 4-OCOCH$_3$ | 526, 524 |
| 26 | 3-Br | 4-OCO-(3-pyridyl) | 589, 587 |
| 27 | 3-N(COCH$_3$)OCOCH$_3$ | 4-OCOCH$_3$ | 561 |
| 28 | 3-NH$_2$ | 4-OH | 419 |
| 29 | 2-Cl | 3,4-(OH)$_2$ | 454 |
| 30 | 2-CH$_3$ | 3,4-(OH)$_2$ | 434 |
| 31 | 2,6-(Cl)$_2$ | 3,4-(OH)$_2$ | 490, 488 |
| 32 | 2-Br | 4-OCH$_3$ | 498, 496 |
| 33 | 2-Br | 2-Cl, 4-OH | 518, 516 |
| 34 | 2-Br | 3,4-(OH)$_2$, 5-OCH$_3$ | 530, 528 |
| 35 | 2-Br | 3,4-[OCON(CH$_3$)$_2$]$_2$ | 642, 640 |
| 36 | 2,5-(Cl)$_2$ | 3,4-(OH)$_2$ | 490, 488 |
| 37 | 3,5-(Cl)$_2$ | 3,4-(OH)$_2$ | 490, 488 |
| 38 | 2-CF$_3$ | 3,4-(OH)$_2$ | 488 |
| 39 | 3-F | 3,4-(OH)$_2$ | 438 |
| 40 | 2,3-(Cl)$_2$ | 3,4-(OH)$_2$ | 490, 488 |
| 41 | 2,3,5-(Cl)$_3$ | 3,4-(OH)$_2$ | 554, 552 |
| 42 | 2-CH(—OCH$_2$CH$_2$O—) | 3,4-(OH)$_2$ | 492 |
| 43 | 2-Br | 3-NO$_2$ | 513, 511 |
| 44 | 3,5-(Br)$_2$ | 3,4-(OH)$_2$ | 580, 578, 576 |
| 45 | 2-CHO | 3,4-(OH)$_2$ | 448 |
| 46 | 2-Br | 3,4-(OCOCH$_3$)$_2$ | 584, 582 |
| 47 | 2-Br | 3,4-(OCOC$_6$H$_5$)$_2$ | 708, 706 |
| 48 | 2-Br | 3,4-[OCOCH(CH$_3$)$_2$]$_2$ | 640, 638 |
| 49 | 2-Br | 3,4-[OCO-(cyclopentyl)]$_2$ | 692, 690 |
| 50 | 2-Br | 4-NO$_2$ | 513, 511 |
| 51 | 2-Br | 3-NH$_2$ | 483, 481 |
| 52 | 2-Br | 4-NH$_2$ | 483, 481 |
| 53 | 2-Br | 3,5-(OH)$_2$ | 500, 498 |
| 54 | 2-CH$_2$CH$_3$ | 3,4-(OH)$_2$ | 448 |
| 55 | 2,5-(Cl)$_2$ | 4-OH | 474, 472 |
| 56 | 2-Br | 4-N(CH$_3$)$_2$ | 511, 509 |
| 57 | 2-Br | 3-OH | 484, 482 |
| 58 | 2-Br | 3-OH, 4,5-[OCH$_2$OCH$_3$]$_2$ | 604, 602 |
| 59 | 2-Br | 3-NHOH | 499, 497 |
| 60 | 2-Br | 3-NHCOCH$_3$ | 525, 523 |
| 61 | 2-Br | 3-NHSO$_2$CH$_3$ | 561, 559 |
| 62 | 2-Br | 3,4,5-(OH)$_3$ | 516, 514 |
| 63(+) | 2-Br | 3,4-(OH)$_2$ | 500, 498 |
| 64(−) | 2-Br | 3,4-(OH)$_2$ | 500, 498 |
| 65 | 2-Br | 3-CH$_2$OH, 4-OH | 514, 512 |
| 66 | 2-CH=CHCH$_3$ | 3,4-(OH)$_2$ | 460 |
| 67 | 2-Br | 4-NHCOCH$_3$ | 525, 523 |
| 68[(±)HCl salt] | 2-Br | 3,4-(OH)$_2$ | 500, 498 |
| 69[(−)HCl salt] | 2-Br | 3,4-(OH)$_2$ | 500, 498 |
| 70[(+)HCl salt] | 2-Br | 3,4-(OH)$_2$ | 500, 498 |
| 71 | 2-CH$_2$CH$_2$CH$_3$ | 3,4-(OH)$_2$ | 462 |
| 72 | 2-CH=CHCH$_2$CH(OCH$_2$CH$_3$)$_2$ | 3,4-(OH)$_2$ | 562 |
| 73 | 2-C$_6$H$_5$ | 3,4-(OH)$_2$ | 496 |
| 74 | 2-CH$_3$ | 2-Br | 482, 480 |

TABLE 2

Examples of Compound (I) and physical data (2)

| Compound | R¹ | R² | R³ | FABMS m/z (M + H)⁺ |
|---|---|---|---|---|
| 75 | 3-pyridylmethyl | 1-methylnaphthyl | 4-hydroxyphenyl | 454 |
| 76 | 3-pyridylmethyl | 2,3-dihydro-1,4-benzodioxin-6-yl | 4-hydroxyphenyl | 462 |
| 77 | 4-pyridylmethyl | 3-bromophenyl | 4-hydroxyphenyl | 484, 482 |
| 78 | 3-pyridylmethyl N-oxide | 3-bromophenyl | 4-hydroxyphenyl | 500, 498 |
| 79 | 3-pyridylmethyl | 2-methylpyridin-6-yl | 4-hydroxyphenyl | 405 |
| 80 | 3-pyridylmethyl | 3-bromophenyl | 3-pyridyl | 469, 467 |
| 81 | 3-pyridylmethyl | 3-chlorophenyl | 3-pyridyl | 423 |

TABLE 2-continued

Examples of Compound (I) and physical data (2)

| Compound | R¹ | R² | R³ | FABMS m/z (M + H)⁺ |
|---|---|---|---|---|
| 82 | 3-pyridylmethyl | 3-thienyl | 3,4-dihydroxyphenyl-methyl | 426 |
| 83 | 3-pyridylmethyl | 5-methyl-2-furyl | 3,4-dihydroxyphenyl-methyl | 410 |
| 84 | 3-pyridylmethyl | 3-fluorophenyl | 3-pyridyl | 408 |
| 85 | 2-pyridylpropyl | 2-bromophenyl | 3,4-dihydroxyphenyl-methyl | 514, 512 |
| 86 | 3-pyridylpropyl | 2-bromophenyl | 3,4-dihydroxyphenyl-methyl | 514, 512 |
| 87 | 4-pyridylmethyl | 2-bromophenyl | 3,4-dihydroxyphenyl-methyl | 500, 498 |
| 88 | 1-imidazolylbutyl | 2-bromophenyl | 3,4-dihydroxyphenyl-methyl | 517, 515 |
| 89 | 3-pyridylmethyl | 2-bromophenyl | camphanate-p-tolyl ester | 665, 663 |

TABLE 2-continued

Examples of Compound (I) and physical data (2)

| Compound | R¹ | R² | R³ | FABMS m/z (M + H)⁺ |
|---|---|---|---|---|
| 90 | 3,4-dihydroxybenzyl (ethyl linker to catechol) | 2-bromophenyl | 3-pyridyl | 500, 498 |
| 91 | 2-pyridylethyl | 2-bromophenyl | 3-hydroxyphenyl | 484, 482 |
| 92 | 3-pyridylethyl | (E)-2-(3-methylphenyl)vinyl-2-pyridyl | 4-hydroxyphenyl | 507 |

TABLE 3

Examples of Compound (I) and physical data (3)

| Compound | R¹ | R² | R³ | FABMS m/z (M + H)⁺ |
|---|---|---|---|---|
| 93 | 3-pyridylethyl | 2-iodophenyl | 3,4-dihydroxyphenyl | 546 |
| 94 | 3-pyridylethyl | 2-vinylphenyl | 3,4-dihydroxyphenyl | 446 |

TABLE 3-continued

Examples of Compound (I) and physical data (3)

| Compound | R¹ | R² | R³ | FABMS m/z (M + H)⁺ |
|---|---|---|---|---|
| 95 | 3-pyridyl-CH₂- | 2-(1,3-dithiolan-2-yl)phenyl | 3,4-dihydroxyphenyl | 524 |
| 96 | 3-pyridyl-CH₂- | 2-(2-methylprop-1-enyl)phenyl | 3,4-dihydroxyphenyl | 474 |
| 97 | 3-pyridyl-CH₂- | 2-ethynylphenyl | 3,4-dihydroxyphenyl | 444 |
| 98 | 3-pyridyl-CH₂- | 2-isopropylphenyl | 3,4-dihydroxyphenyl | 467 |
| 99 | 3-pyridyl-CH₂- | 2-bromophenyl | 1H-imidazol-2-yl | 458, 456 |
| 100 | 3-pyridyl-CH₂- | 2-bromophenyl | 1H-indol-3-yl | 507, 505 |
| 101 | 3-pyridyl-CH₂- | 2-bromophenyl | 4-pyridyl | 469, 467 |
| 102 | 3-pyridyl-CH₂- | 2-bromophenyl | 2-pyridyl | 469, 467 |

TABLE 3-continued
Examples of Compound (I) and physical data (3)
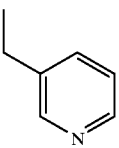
| Compound | R¹ | R² | R³ | FABMS m/z (M + H)⁺ |
|---|---|---|---|---|
| 103 | 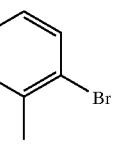 | 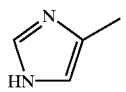 | 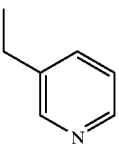 | 458, 456 |
| 104 | 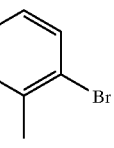 | 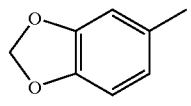 | 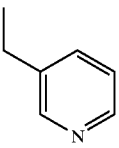 | 512, 510 |
| 105 | 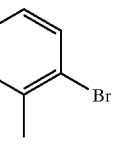 | 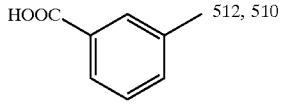 | 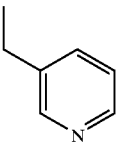 | 512, 510 |
| 106 | 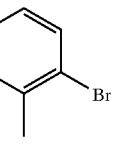 | 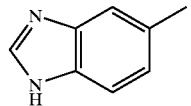 | 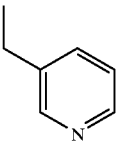 | 510, 508 |
| 107 (+) | 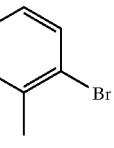 | 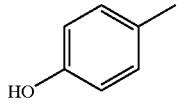 | 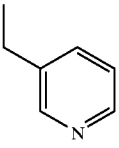 | 484, 482 |
| 108 (−) | 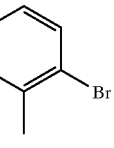 | 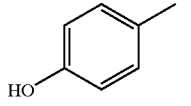 | 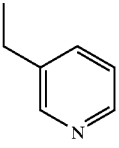 | 484, 482 |
| 109 | 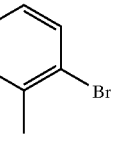 | 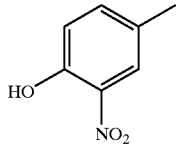 | 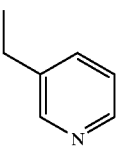 | 529, 527 |
| 110 | 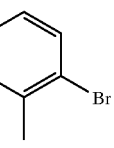 | | 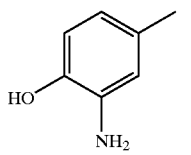 | 499, 497 |

TABLE 4

Examples of Compound (I) and physical data (4)

| Compound | R² | R³ | FABMS (M + H)⁺ or TOFMS (M + H)⁺or EIMS (M⁺) m/z |
|---|---|---|---|
| 111 | 2-Br-phenyl | 2-NO₂-phenyl | 510 (M + H)⁺ |
| 112 | 2-Br-phenyl | 2-NHOH-phenyl | 499, 497 (M + H)⁺ |
| 113 | 2-Br-phenyl | 4-(1-propenyl)-1-trityl-imidazol-4-yl | 726, 724 (M + H)⁺ |
| 114 | 2-Br-phenyl | 4-(1-propenyl)-1H-imidazol-4-yl | 484, 482 (M + H)⁺ |
| 115 | 2-Br-phenyl | 2,4-bis(Boc-NH)-5-methylphenyl | 698, 696 (M + H)⁺ |

TABLE 4-continued
Examples of Compound (I) and physical data (4)
| Compound | R² | R³ | FABMS (M + H)⁺ or TOFMS (M + H)⁺ or EIMS (M⁺) m/z |
|---|---|---|---|
| 116 | 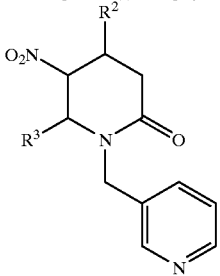 |  | 585, 583 (M + H)$^+$ |
| 117 | 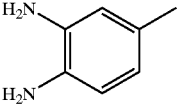 |  | 498, 496 (M + H)$^+$ |
| 118 | 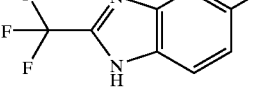 |  | 576, 574 (M + H)$^+$ |
| 119 | 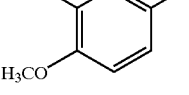 | 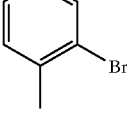 | 528, 526 (M + H)$^+$ |
| 120 | 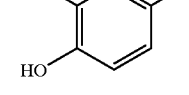 | 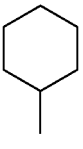 | 514, 512 (M + H)$^+$ |
| 121 | 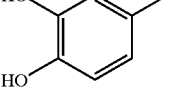 |  | 426 (M + H)$^+$ |
| 122 | 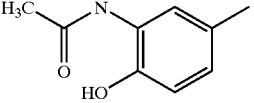 | | 541, 539 (M + H)$^+$ |

TABLE 4-continued

Examples of Compound (I) and physical data (4)

| Compound | R² | R³ | FABMS (M + H)⁺ or TOFMS (M + H)⁺ or EIMS (M⁺) m/z |
|---|---|---|---|
| 123 | 2-methyl-2-butenyl (CH₃, CH₃) | 3-pyridyl | 367 (M + H)⁺ |
| 124 | 2-methyl-2-butenyl (CH₃, CH₃) | 3,4-dihydroxyphenyl | 398 (M + H)⁺ |
| 125 | 2-bromophenyl | 5-methyl-2-hydroxy-benzoic acid (salicylate) | 528, 526 (M + H)⁺ |
| 126 | 2-bromophenyl | 1-benzyl-5-methyl-2-pyridone | 575, 573 (M + H)⁺ |
| 127 | 2-bromophenyl | 3-methylphenyl | 468, 466 (M + H)⁺ |
| 128 | 2-bromophenyl | 4-fluoro-3-methylphenyl | 486, 466 (M + H)⁺ |
| 129 | 2-bromophenyl | 2-methyl-2-butenyl | 446, 444 (M + H)⁺ |

TABLE 4-continued
Examples of Compound (I) and physical data (4)
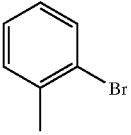
| Compound | R² | R³ | FABMS (M + H)⁺ or TOFMS (M + H)⁺or EIMS (M⁺) m/z |
|---|---|---|---|
| 130 | 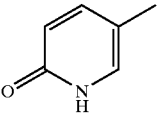 | 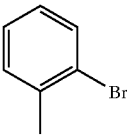 | 517, 515 (M + H)⁺ |
| 131 | 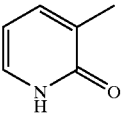 | 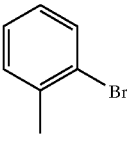 | 485, 483 (M + H)⁺ |
| 132 | 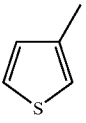 | 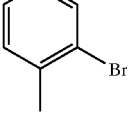 | 474, 472 (M + H)⁺ |
| 133 | 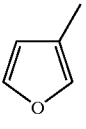 | 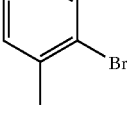 | 458, 456 (M + H)⁺ |
| 134 |  | 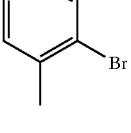 | 458, 456 (M + H)⁺ |
| 135 | 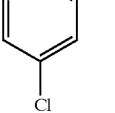 | 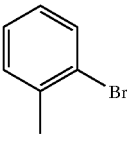 | 501, 499 (M⁺) |
| 136 | 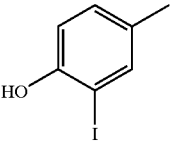 | | 609, 607 (M⁺) |

TABLE 4-continued
Examples of Compound (I) and physical data (4)
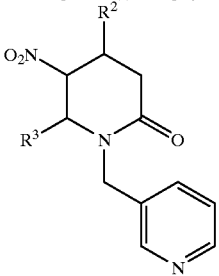
| Compound | R² | R³ | FABMS (M + H)⁺ or TOFMS (M + H)⁺ or EIMS (M⁺) m/z |
|---|---|---|---|
| 137 | 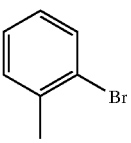 | 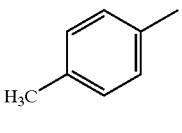 | 481, 479 (M⁺) |
| 138 |  | 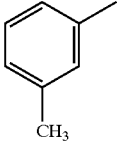 | 481, 479 (M⁺) |
| 139 | 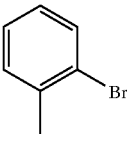 | 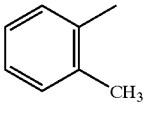 | 481, 479 (M⁺) |
| 140 |  | 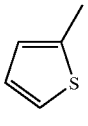 | 473, 471 (M⁺) |
| 141 |  | 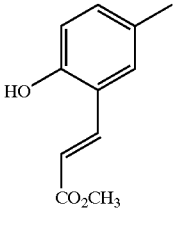 | 568, 566 (M + H)⁺ |
| 142 |  | 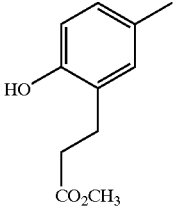 | 570, 568 (M + H)⁺ |
| 143 |  | 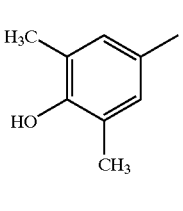 | 512, 510 (M + H)⁺ |

TABLE 4-continued

Examples of Compound (I) and physical data (4)

| Compound | R² | R³ | FABMS (M + H)⁺ or TOFMS (M + H)⁺ or EIMS (M⁺) m/z |
|---|---|---|---|
| 144 | 2-bromophenyl | 2-hydroxy-5-methylphenyl with oct-1-ynyl substituent | 591, 589 (M + H)⁺ |
| 145 | 2-bromophenyl | 3-(dihydroxyboryl)phenyl | 512, 510 (M + H)⁺ |
| 146 | 2-ethylphenyl | 4-hydroxyphenyl | 432 (M + H)⁺ |
| 147 | 2-ethylphenyl | 4-hydroxy-3-nitrophenyl | 477 (M + H)⁺ |
| 148 | 2-(prop-1-enyl)phenyl | 4-hydroxyphenyl | 444 (M + H)⁺ |
| 149 | 2-(methylthio)phenyl | 4-hydroxyphenyl | 450 (M + H)⁺ |

TABLE 4-continued

Examples of Compound (I) and physical data (4)

| Compound | R² | R³ | FABMS (M + H)⁺ or TOFMS (M + H)⁺ or EIMS (M⁺) m/z |
|---|---|---|---|
| 150 | 2-Br-phenyl | 3-CN-phenyl | 493, 491 (M + H)⁺ |
| 151 | 2-Br-phenyl | 5-methyl-2-furyl-SO₃H | 538, 536 (M + H)⁺ |
| 152 | 2-Br-phenyl | 5-methyl-2-thienyl-CO₂H | 516 (M + H)⁺ |

TABLE 5

Examples of Compound (I) and physical data (5)

| Compound | R²ᵃ, R²ᵇ, R²ᶜ | R³ᵃ, R³ᵇ, R³ᶜ | TOFMS m/z (M + H)⁺ |
|---|---|---|---|
| 153 | 2-Br | 2,5-(CH₃)₂ | 496, 494 |
| 154 | 2-I | 2,5-(CH₃)₂ | 542 |
| 155 | 2-CH₃ | 2,5-(CH₃)₂ | 430 |
| 156 | 2-CH₂CH₃ | 2,5-(CH₃)₂ | 444 |
| 157 | 2-Br | 3-OCH₃ | 498, 496 |
| 158 | 2-I | 3-OCH₃ | 544 |
| 159 | 2-CH₃ | 3-OCH₃ | 432 |
| 160 | 2-CH₂CH₃ | 3-OCH₃ | 446 |

TABLE 5-continued

Examples of Compound (I) and physical data (5)

| Compound | $R^{2a}, R^{2b}, R^{2c}$ | $R^{3a}, R^{3b}, R^{3c}$ | TOFMS m/z (M + H)$^+$ |
|---|---|---|---|
| 161 | 2-I | 4-OCH$_3$ | 544 |
| 162 | 2-CH$_3$ | 4-OCH$_3$ | 432 |
| 163 | 2-CH$_2$CH$_3$ | 4-OCH$_3$ | 446 |
| 164 | 2-I | H | 514 |
| 165 | 2-CH$_3$ | H | 402 |
| 166 | 2-CH$_2$CH$_3$ | H | 416 |
| 167 | 2-Br | 2-F | 486, 484 |
| 168 | 2-CH$_2$CH$_3$ | 2-F | 434 |
| 169 | 2-Br | 3-OCH$_2$CH$_3$, 4-OH | 528, 526 |
| 170 | 2-CH$_2$CH$_3$ | 3-OCH$_2$CH$_3$, 4-OH | 476 |
| 171 | 2-Br | 3-OCH$_3$, 4-OH | 498, 496 |
| 172 | 2-CH$_2$CH$_3$ | 3-CH$_3$, 4-OH | 446 |
| 173 | 2-Br | 2-OH, 3-OCH$_3$ | 514, 512 |
| 174 | 2-CH$_2$CH$_3$ | 2-OH, 3-OCH$_3$ | 462 |
| 175 | 2-CH$_2$CH$_3$ | 4-OH, 3,5-(CH$_3$)$_2$ | 460 |
| 176 | 2-Br | 4-OH, 3,5-(OCH$_3$)$_2$ | 542, 544 |
| 177 | 2-CH$_2$CH$_3$ | 4-OH, 3,5-(OCH$_3$)$_2$ | 492 |
| 178 | 2-Br | 3,5-(OCH$_3$)$_2$ | 528, 526 |
| 179 | 2-OCH$_3$, 4-OH | | 462 |
| 180 | 2-Br | 2-Br, 3-OCH$_3$, 4-OH | 594, 592, 590 |
| 181 | 2-CH$_2$CH$_3$ | 2-Br, 3-OCH$_3$, 4-OH | 542, 540 |
| 182 | 2-Br | 4-CN | 493, 491 |
| 183 | 2-CH$_2$CH$_3$ | 4-CN | 441 |
| 184 | 2-CH$_2$CH$_3$ | 3,5-(OCH$_3$)$_2$ | 476 |
| 185 | 2-Br | 4-C$_4$H$_9$ | 524, 522 |
| 186 | 2-CH$_2$CH$_3$ | 4-C$_4$H$_9$ | 472 |
| 187 | 2-Br | 4-SCH$_3$ | 514, 512 |
| 188 | 2-CH$_2$CH$_3$ | 4-SCH$_3$ | 462 |
| 189 | 2-Br | 3-Cl, 4-F | 520, 518 |
| 190 | 2-CH$_2$CH$_3$ | 3-Cl, 4-F | 468 |
| 191 | 2-Br | 4-CF$_3$ | 536, 534 |
| 192 | 2-CH$_2$CH$_3$ | 4-CF$_3$ | 484 |
| 193 | 2-Br | 2,5-(OCH$_3$)$_2$ | 528, 526 |
| 194 | 2-CH$_2$CH$_3$ | 2,5-(OCH$_3$)$_2$ | 476 |
| 195 | 2-Br | 4-CH(CH$_3$)$_2$ | 510, 508 |
| 196 | 2-CH$_2$CH$_3$ | 4-CH(CH$_3$)$_2$ | 458 |
| 197 | 2-Br | 2-OCH$_2$CH$_3$ | 512, 510 |
| 198 | 2-CH$_2$CH$_3$ | 2-OCH$_2$CH$_3$ | 460 |
| 199 | 2-Br | 2,4,5-(OCH$_3$)$_3$ | 558, 556 |
| 200 | 2-CH$_2$CH$_3$ | 2,4,5-(OCH$_3$)$_3$ | 506 |
| 201 | 2-Br | 2,3-(OCH$_3$)$_2$ | 528, 526 |
| 202 | 2-CH$_2$CH$_3$ | 2,3-(OCH$_3$)$_2$ | 476 |
| 203 | 2-Br | 4-Ph | 544, 542 |
| 204 | 2-CH$_2$CH$_3$ | 4-Ph | 492 |
| 205 | 2-Br | 4-OPh | 560, 558 |
| 206 | 2-CH$_2$CH$_3$ | 4-OPh | 508 |
| 207 | 2-Br | 2-OCH$_3$ | 498, 496 |
| 208 | 2-CH$_2$CH$_3$ | 2-OCH$_3$ | 446 |
| 209 | 2-CH$_2$CH$_3$ | 4-B(OH)$_2$ | 460 |
| 210 | 2-Br | 4-B(OH)$_2$ | 512, 510 |

TABLE 6

Examples of Compound (I) and physical data (6)

| Compound | $R^{2a}, R^{2b}, R^{2c}$ | $R^3$ | FABMS m/z (M + H)$^+$ |
|---|---|---|---|
| 211 | 2-Br | 4-hydroxy-3-methoxystyryl | 540, 538 |
| 212 | 2-CH$_2$CH$_3$ | 4-hydroxy-3-methoxystyryl | 488 |
| 213 | 2-Br | 5-methylfuran-2-yl | 472, 470 |
| 214 | 2-CH$_2$CH$_3$ | 5-methylfuran-2-yl | 420 |
| 215 | 2-Br | 5-(hydroxymethyl)furan-2-yl | 488, 486 |
| 216 | 2-CH$_2$CH$_3$ | 5-(hydroxymethyl)furan-2-yl | 436 |
| 217 | 2-Br | styryl | 494, 492 |

TABLE 6-continued

Examples of Compound (I) and physical data (6)

| Compound | R²ᵃ, R²ᵇ, R²ᶜ | R³ | FABMS m/z (M + H)⁺ |
|---|---|---|---|
| 218 | 2-Br | 2-naphthyl | 518, 516 |
| 219 | 2-CH₂CH₃ | 2-naphthyl | 466 |
| 220 | 2-CH₂CH₃ | 5-methyl-2-thienyl | 436 |
| 221 | 2-CH₂CH₃ | 5-bromo-2-thienyl | 502, 500 |
| 222 | 2-Br | isobutyl (CH₂CH(CH₃)₂) | 448, 446 |
| 223 | 2-CH₂CH₃ | isobutyl (CH₂CH(CH₃)₂) | 396 |
| 224 | 2-CH₃ | 2-naphthyl | 452 |
| 225 | 2-Br | ethyl | 420, 418 |
| 226 | 2-Br | 3,7-dimethyl-oct-6-enyl | 516, 514 |
| 227 | 2-Br | ethoxycarbonyl-cyclopropyl | 504, 502 |
| 228 | 2-CH₂CH₃ | phenethyl | 496, 494 |
| 229 | 2-CH₃ | 3,7-dimethyl-oct-6-enyl | 550 |
| 230 | 2-CH₃ | ethoxycarbonyl-cyclopropyl | 438 |
| 231 | 2-CH₃ | phenethyl | 430 |
| 232 | 2-Br | 2-hydroxy-3-(methylsulfonylamino)-5-methylphenyl | 577, 575 |

TABLE 6-continued

Examples of Compound (I) and physical data (6)

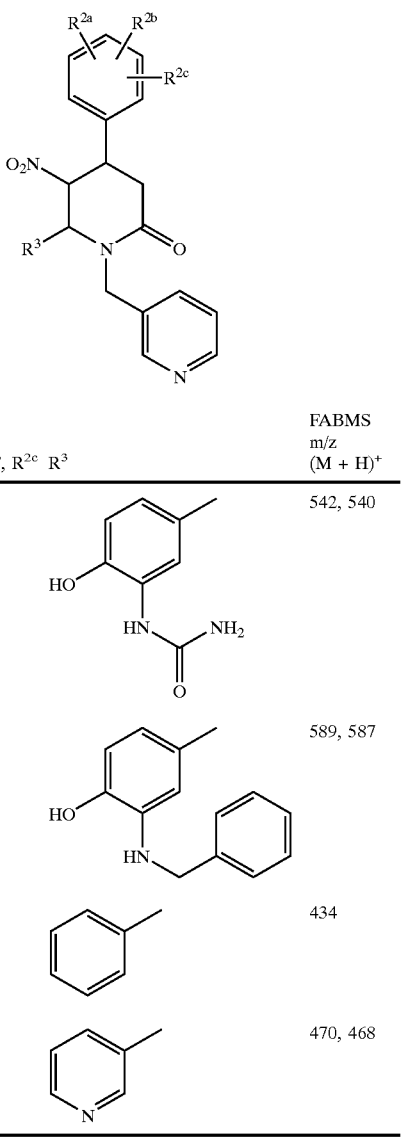

| Compound | $R^{2a}, R^{2b}, R^{2c}$ | $R^3$ | FABMS m/z $(M + H)^+$ |
|---|---|---|---|
| 233 | 2-Br | (2-hydroxy-5-methylphenyl with HN-C(=O)-NH$_2$) | 542, 540 |
| 234 | 2-Br | (2-hydroxy-5-methylphenyl with HN-CH$_2$-phenyl) | 589, 587 |
| 235 | 2-SCH$_3$ | (phenyl) | 434 |
| 236 | 2-Br | (5-methyl-pyridin-3-yl) | 470, 468 |

Next, the pharmacological activities of Compound (I) will be illustrated by reference to Test Examples.

Test Example 1
Proliferation Inhibition Test on Human Colonic Cancer DLD-1 Cell

On a 96-well microtiter plate (Nunc #167008), 1,000/well of human colonic cancer DLD-1 cells were supplied, which were then pre-incubated in RPMI1640 medium containing 5% or 10% fetal calf serum (FCS) in a 5% carbon dioxide gas incubator at 37° C. for 24 hours. Subsequently, a 10 mmol/L solution of each test compound in dimethylsulfoxide (DMSO) was diluted with the incubation medium and then further diluted 3-fold stepwise. The incubation was performed for additional 72 hours. After the completion of the incubation, the medium was discarded followed by the addition of 50 μl/well of a solution of 3-(4,5-dimethylthiazol-2-yl)-2,5-diphenyltetrazolium bromide (Sigma, hereinafter referred to simply as MTT) in the incubation medium (final concentration: 1 mg/ml). After maintaining the plate at 37° C. in a 5% carbon dioxide gas incubator for 4 hours, the MTT solution was discarded and 150 μl/well of DMSO was added. After completely dissolving the MTT-formazane crystals by vigorously stirring with the use of a plate mixer, the difference in the absorbances at 550 nM and 630 nM was measured by using a microplate reader SPECTRAmax 250 (Wako Pure Chemical Industries, Ltd.) The 50% inhibitory concentration ($IC_{50}$) showing the proliferation inhibitory activity was calculated by using 4-parameter logistic curves of the included software SOFTmaxPRO.

TABLE 7

Proliferation inhibitory effect on human colonic cancer DLD-1 cell

| Compound | $IC_{50}$ (μM) |
|---|---|
| 1 | 25 |
| 4 | 25 |
| 14 | 18 |
| 22 | 14 |
| 63 | 5.4 |
| 64 | 9.4 |
| 75 | 27 |
| 121 | 32 |
| 122 | 32 |

Test Example 2
Anti-tumor Activity Test on Human Colonic Cancer DLD-1 Solid Tumor Transplanted in Nude Mouse Fragments (2 mm×2 mm) were excised from well-proliferating parts of human colonic cancer cell DLD-1 tumor masses which had been subcultured in male nude mice (BALB/c-nu/nu mice, Clea Japan). Then, these fragments were subcutaneously transplanted into the abdominal region of 7-week-old male nude mice by using trocars. When the tumor volume (see, Formula-1) attained 50 to 70 mm³, the mice were divided into groups each having 5 animals. Next, each test compound was dissolved in physiological saline containing polyoxyethyelne sorbitan monooleate and the resulting solution was intraperitoneally administered to the mice twice a day continuously for 10 days. The value T/C (%) of each test compound was determined by measuring the tumor volume before the administration (V0) and that after the administration (V) and calculating the ratio (V/V0), as Formula-2 shows. The results are given in Table 8.

Tumor volume (mm³)={major diameter (mm)×(minor diameter (mm))²}×1/2  Formula-1

T/C (%)=((V/V0 of test group)/(V/V0 of control group))× 100.  Formula-2

TABLE 8

Antitumor effect on human colonic cancer DLD-1 solid tumor transplanted in nude mouse

| Compound | Dose (mg/kg) | T/C (%) |
|---|---|---|
| 14 | 50 | 47 |
| 22 | 50 | 40 |

Test Example 3
Proliferation Inhibition Test on Human Pancreatic Cancer MIA-PaCa2 Cell On a 96-well microtiter plate (Nunc #167008), 2,000/well of human pancreatic cancer MIA-PaCa2 cells were supplied, which were then preincubated in RPMI1640 medium containing 10% fetal calf serum (FCS) in a 5% carbon dioxide gas incubator at 37° C. for 24 hours. Subsequently, a 10 mmol/L solution of each test compound in dimethyl sulfoxide (DMSO) was diluted with the incubation medium and then further diluted 3-fold stepwise. The incubation was performed for additional 72 hours. After the completion of the incubation, the medium was discarded, followed by the addition of 50 μl/well of a solution of 3-(4,5-dimethylthiazol-2-yl)-2,5-diphenyltetrazolium bromide (Sigma, hereinafter referred to simply as MTT) in the incubation medium (final concentration: 1 mg/ml). After maintaining the plate at 37° C. in a 5% carbon dioxide gas incubator for 4 hours, the MTT solution was discarded and 150 μl/well of DMSO was added. After completely dissolving the MTT-formazane crystals by vigorously stirring with the use of a plate mixer, the difference in the absorbances at 550 nM and 630 nM was measured by using a microplate reader SPECTRAmax 250 (Wako Pure Chemical Industries, Ltd.). The 50% inhibitory concentration ($IC_{50}$) showing the proliferation inhibitory activity was calculated by using 4-parameter logistic curves of the included software SOFTmaxPRO.

TABLE 9

Proliferation inhibitory effect on human pancreatic cancer MIA-PaCa2 cell

| Compound | $IC_{50}$ (μM) |
|---|---|
| 132 | 71 |
| 139 | 21 |
| 140 | 41 |
| 141 | 26 |
| 142 | 16 |
| 143 | 22 |
| 144 | 13 |
| 148 | 26 |
| 149 | 19 |
| 153 | 20 |
| 160 | 17 |
| 168 | 27 |
| 170 | 19 |
| 171 | 8.2 |
| 172 | 9.3 |
| 174 | 12 |
| 175 | 6.1 |
| 177 | 24 |
| 178 | 28 |
| 179 | 17 |
| 180 | 17 |
| 185 | 3.4 |
| 186 | 11 |
| 187 | 9.1 |
| 188 | 28 |
| 189 | 4.1 |
| 190 | 23 |
| 191 | 14 |
| 193 | 1.9 |
| 194 | 4 |
| 195 | 5 |
| 196 | 10 |
| 197 | 2.1 |
| 198 | 2.8 |
| 199 | 15 |
| 200 | 7.5 |
| 201 | 5.7 |
| 202 | 5.7 |
| 203 | 8.1 |
| 204 | 5.1 |
| 205 | 7.4 |
| 206 | 4.1 |
| 207 | 6.4 |
| 208 | 7.3 |
| 209 | 16 |

TABLE 9-continued

Proliferation inhibitory effect on human pancreatic cancer MIA-PaCa2 cell

| Compound | $IC_{50}$ (μM) |
|---|---|
| 211 | 14 |
| 212 | 14 |
| 217 | 9 |
| 218 | 5 |
| 219 | 8.5 |
| 220 | 13 |
| 221 | 17 |
| 226 | 3.8 |
| 235 | 31 |

The above Compound (I) have an effect of inhibiting the proliferation of human colonic cancer DLD-1 cells and human pancreatic cancer MIA-PaCa2 cells and, therefore, are useful as the active ingredient of medicaments, preferably antitumor agents. The first embodiment of the pharmaceutical composition of the present invention is characterized by containing as the active ingredient substances selected from the group consisting of Compound (I), pharmaceutically acceptable salts thereof, and hydrates and solvates of the same. The pharmaceutical compositions of the present invention are useful as antitumor agents in treating non-solid cancers such as leukemia, malignant lymphoma and myeloma and solid cancers such as gastric cancer, esophageal cancer, intestinal cancer, rectum cancer, pancreatic cancer, hepatic cancer, renal cancer, bladder cancer, pulmonary cancer, uterus cancer, ovarian cancer, mammary cancer, prostatic cancer, skin cancer and brain tumor.

For the medicaments of the present invention, the above-mentioned substances as such may be administered as the active ingredient. However, it is generally preferable to administer them in the form of pharmaceutical compositions comprising the above substances together with one or more pharmaceutical additives. These pharmaceutical compositions can be produced by using methods which are well known or have been conventionally employed in the field of pharmaceutics. The medicaments of the present invention in the form of such pharmaceutical compositions may contain one or more other pharmaceutically active ingredients. The medicaments of the present invention are applicable to mammals including humans.

The medicaments of the present invention may be administered via an arbitrary route without restriction, and the most suitable administration route may be selected from oral and parenteral routes depending on the purpose of treatment and/or prevention. Examples of the parenteral administration route include tracheobronchial, rectal, subcutaneous, intramuscular and intravenous routes. Examples of the preparation appropriate for oral administration include tablets, granules, fine granules, powders, syrups, solutions, capsules and suspensions, while examples of the preparation appropriate for parenteral administration include injections, drips, inhalants, sprays, suppositories, transdermal absorption preparations and mucosal absorption preparations.

To prepare liquid preparations appropriate for oral administration, pharmaceutical additives such as water; saccharides (e.g., sucrose, sorbitol, fructose); glycols (e.g., polyethylene glycol, propylene glycol); oils (e.g., sesame oil, olive oil, soybean oil); preservatives (e.g., p-hydroxybenzoates); and the like can be used. To prepare solid preparations such as capsules, tablets or granules, excipients (e.g., lactose, glucose, sucrose, mannitol); disintegrating agents (e.g., starch, sodium alginate); lubricating agents (e.g., magnesium stearate, talc); binders (e.g., polyvinyl alcohol, hydroxypropylcellulose, gelatin); surfactants (e.g., fatty acid esters); and plasticizers (e.g., glycerol); and the like may be used.

Among the preparations appropriate for parenteral administration, those for intravascular administration (e.g., injections, drips) may be prepared preferably with the use of aqueous media isotonic to human blood. For example, injections may be prepared with the use of aqueous media selected from salt solutions, glucose solutions and saline/glucose solution mixtures in accordance with a conventional manner by using appropriate adjuvants to give solutions, suspensions or dispersions. Suppositories for rectal administration may be prepared by using carriers such as cacao fat, hydrogenated fats or hydrogenated carboxylic acids. Sprays may be prepared by using carriers which can promote the dispersion of the above-mentioned substances serving as the active ingredient in the form of fine particles and the absorption thereof without irritating human oral cavity or respiratory mucosa. As such a carrier, lactose, glycerol, or the like may be used. These preparations may be in the form of aerosols, dry powders, etc. depending on the properties of the above-mentioned substances serving as the active ingredient as well as the properties of the carriers selected. To produce preparations for parenteral administration, one or more pharmaceutical additives selected from diluents, flavors, preservatives, excipients, disintegrating agents, lubricating agents, binders, surfactants, plasticizers, and the like may be used. The dosage forms and production processes of the medicaments of the present invention are not restricted to those described above in detail.

The dose and administration frequency of the medicaments of the present invention are not particularly restricted but can be appropriately determined depending on various factors, for example, the type of the above-described substance as the active ingredient, the type of the cancer to be treated, the administration route, the age and body weight of the patient, and the conditions and severity of the disease. For example, about 0.01 to 500 mg/kg/day may be administered to an adult at a frequency of once to 5 times in a day or once in several days to several weeks, though neither the dose nor the administration frequency is restricted thereto. The medicament of the present invention can be used together with other antitumor agents. It is generally favorable to combine the medicament of the present invention with several antitumor agents differing in the functional mechanism.

BEST MODE FOR CARRYING OUT THE INVENTION

Hereinafter, Examples and Production Examples of the present invention will be given.

Production Example 1
Tablet

A tablet of the following composition is prepared in a conventional manner:

| | |
|---|---|
| Compound 1 | 10 mg |
| Lactose | 30 mg |
| Potato starch | 15 mg |
| Polyvinyl alcohol | 1.5 mg |
| Magnesium stearate | 0.5 mg. |

Production Example 2
Capsule

A capsule of the following composition is prepared in a conventional manner:

| | |
|---|---|
| Compound 1 | 10 mg |
| Lactose | 100 mg |
| Magnesium stearate | 2.5 mg. |

The above components are mixed and packed into a gelatin capsule.

Production Example 3
Injection

An injection of the following composition is prepared in a conventional manner:

| | |
|---|---|
| Compound 1 | 2 mg |
| Refined soybean oil | 200 mg |
| Refined yolk lecithin | 24 mg |
| Glycerol for injection | 50 mg |
| Distilled water for injection | 1.72 ml. |

EXAMPLE 1
Synthesis of Compound 1

Methyl 3-(3-bromophenyl)-4-nitrobutyrate (302 mg, 1.0 mmol), 4-hydroxybenzaldehyde (122 mg, 1.0 mmol) and 3-aminomethylpyridine (0.20 mL, 2.0 mmol) were heated under reflux in ethanol for 20 hours. After evaporating ethanol under reduced pressure, the residue was purified by silica gel column chromatography (eluted with chloroform/methanol=95/5) to give Compound 1 (293 mg, yield 61%).

$^1$HNMR (DMSO-$d_6$, 300 MHz) δ9.65 (br s, 1H), 8.42 (br d, J=3.1 Hz, 1H), 8.16 (br s, 1H), 7.73 (m, 1H), 7.50–7.20 (m, 5H), 7.09 (m, 2H), 6.69 (m, 2H), 5.73 (dd, J=11.1, 10.0 Hz, 1H), 4.79 (d, J=10.0 Hz, 1H), 4.70 (d, J=15.6 Hz, 1H), 3.94 (d, J=15.6 Hz, 1H), 3.94 (m, 1H), 3.14 (dd, J=17.0, 13.2 Hz, 1H), 2.75 (dd, J=17.0, 3.7 Hz, 1H)

EXAMPLE 2
Synthesis of Compound 2

From methyl 3-(3-methoxyphenyl)-4-nitrobutyrate (253 mg, 1.0 mmol), 4-hydroxybenzaldehyde (82 mg, 0.67 mmol) and 3-aminomethylpyridine (0.135 mL, 1.33 mmol), Compound 2 (173 mg, yield 60%) was obtained in the same manner as in Example 1.

$^1$HNMR (DMSO-$d_6$, 300 MHz) δ9.62 (br s, 1H), 8.42 (br dd, J=4.8, 2.0 Hz, 1H), 8.16 (br d, J=2.0 Hz, 1H), 7.50–6.80 (m, 10H), 5.66 (dd, J=11.5, 10.0 Hz, 1H), 4.79 (d, J=10.0 Hz, 1H), 4.72 (d, J=15.6 Hz, 1H), 3.93 (d, J=15.6 Hz, 1H), 3.86 (m, 1H), 3.74 (s, 3H), 3.16 (dd, J=16.9, 13.0 Hz, 1H), 2.72 (dd, J=16.9, 4.9 Hz, 1H)

EXAMPLE 3
Synthesis of Compound 3

From methyl 3-(3-methoxyphenyl)-4-nitrobutyrate (253 mg, 1.0 mmol), 4-benzyloxybenzaldehyde (140 mg, 0.66 mmol) and 3-aminomethylpyridine (0.134 mL, 1.32 mmol), Compound 3 (135 mg, yield 39%) was obtained in the same manner as in Example 1.

$^1$HNMR (DMSO-$d_6$, 300 MHz) δ8.37 (dd, J=4.7, 1.8 Hz, 1H), 8.10 (br d, J=1.8 Hz, 1H), 7.43–6.78 (m, 15H), 5.67 (dd, J=11.4, 10.1 Hz, 1H), 5.03 (br s, 2H), 4.86 (d, J=10.1 Hz, 1H), 4.58 (d, J=15.6 Hz, 1H), 4.03 (d, J=15.6 Hz, 1H), 3.85 (m, 1H), 3.78 (s, 3H), 3.15 (dd, J=17.0, 13.0 Hz, 1H), 2.73 (dd, J=17.0, 5.0 Hz, 1H)

EXAMPLE 4
Synthesis of Compound 4

Compound 1 obtained in Example 1 (20 mg, 0.041 mmol) was dissolved in methanol (5.0 mL), and palladium-carbon (10%, 4.3 mg) was added thereto, followed by stirring under a hydrogen atmosphere at room temperature for 19 hours. After removing palladium-carbon by filtration, the filtrate was purified by preparative thin layer chromatography (developed with chloroform/methanol=95/5) to give Compound 4 (4.0 mg, yield 24%).

$^1$HNMR (CDCl$_3$+CD$_3$OD, 300 MHz) δ8.46 (br dd, J=4.7, 1.4 Hz, 1H), 8.09 (br d, J=1.4 Hz, 1H), 7.58 (m, 1H), 7.40–7.28 (m, 6H), 6.95 (m, 2H), 6.80 (m, 2H), 5.08 (dd, J=11.7, 9.5 Hz, 1H), 5.07 (d, J=15.0 Hz, 1H), 4.78 (d, J=9.5 Hz, 1H), 3.94 (d, J=15.0 Hz, 1H), 3.70 (m, 1H), 3.03–2.90 (m, 2H)

EXAMPLE 5
Synthesis of Compound 5

From methyl 3-(3-bromophenyl)-4-nitrobutyrate (302 mg, 1.0 mmol), 3-hydroxybenzaldehyde (122 mg, 1.0 mmol) and 3-aminomethylpyridine (0.20 mL, 2.0 mmol), Compound 5 (95 mg, yield 19%) was obtained in the same manner as in Example 1.

$^1$HNMR (DMSO-d$_6$, 300 MHz) δ9.61 (br s, 1H), 8.44 (br d, J=4.6 Hz, 1H), 8.20 (br s, 1H), 7.94 (m, 1H), 7.52–6.60 (m, 9H), 5.72 (dd, J=11.4, 10.0 Hz, 1H), 4.83 (d, J=15.4 Hz, 1H), 4.79 (d, J=10.0 Hz, 1H), 3.95 (m, 1H), 3.83 (d, J=15.4 Hz, 1H), 3.17 (dd, J=17.0, 12.7 Hz, 1H), 2.75 (dd, J=17.0, 4.8 Hz, 1H)

EXAMPLE 6
Synthesis of Compound 7

From methyl 3-(3-bromophenyl)-4-nitrobutyrate (151 mg, 0.50 mmol), 4-cyanobenzaldehyde (66 mg, 0.50 mmol) and 3-aminomethylpyridine (0.10 mL, 1.0 mmol), Compound 7 (28 mg, yield 11%) was obtained in the same manner as in Example 1.

$^1$HNMR (CDCl$_3$, 300 MHz) δ8.59 (br d, J=4.5 Hz, 1H), 8.25 (br s, 1H), 7.80–7.10 (m, 10H), 5.34 (d, J=15.0 Hz, 1H), 5.00–4.80 (m, 2H), 3.70 (m, 1H), 3.64 (d, J=17.0 Hz, 1H), 3.03 (dd, J=17.5, 5.0 Hz, 1H), 2.89 (dd, J=17.5, 13.0 Hz, 1H)

EXAMPLE 7
Synthesis of Compound 9

From methyl 3-(3-bromophenyl)-4-nitrobutyrate (151 mg, 0.50 mmol), 3,4-dihydroxybenzaldehyde (69 mg, 0.50 mmol) and 3-aminomethylpyridine (0.10 mL, 1.0 mmol), Compound 9 (160 mg, yield 64%) was obtained in the same manner as in Example 1.

$^1$HNMR (DMSO-d$_6$, 300 MHz) δ9.22 (br s, 1H), 8.97 (br s, 1H), 8.45 (m, 1H), 8.23 (br s, 1H), 7.74 (br s, 1H), 7.52–7.23 (m, 5H), 6.73–6.62 (m, 2H), 6.50 (m, 1H), 5.66 (dd, J=11.4, 10.0 Hz, 1H), 4.86 (d, J=15.4 Hz, 1H), 4.67 (d, J=10.0 Hz, 1H), 3.91 (m, 1H), 3.80 (d, J=15.4 Hz, 1H), 3.14 (dd, J=17.0, 13.0 Hz, 1H), 2.73 (dd, J=17.0, 4.4 Hz, 1H)

EXAMPLE 8
Synthesis of Compound 10

Under an argon atmosphere, (1-ethoxyvinyl)tributyltin (0.013 mL, 0.04 mmol) and Compound 1 (19 mg, 0.04 mmol) were added to a solution (2 mL) of bis (triphenylphosphine)palladium (II) dichloride (14 mg, 0.02 mmol) in dimethylformamide (DMF), followed by stirring at 80° C. for 4 hours. Next, the reaction solution was filtered through celite and chloroform was added to the filtrate, followed by washing with hydrochloric acid (1 mol/L). Subsequently, the organic layer was neutralized with a saturated aqueous solution of hydrogen bicarbonate and dried over sodium sulfate. After evaporating the solvent under reduced pressure, the residue was purified by silica gel column chromatography (eluted with chloroform/methanol= 1/19) to give Compound 10 (4.7 mg, yield 26%).

$^1$HNMR (CD$_3$OD, 300 MHz) δ8.37 (d, J=3.9 Hz, 1H), 8.10 (s, 1H), 8.01 (t, J=1.5 Hz, 1H), 7.93 (dt, J=7.9, 1.5 Hz, 1H), 7.62 (dt, J=7.9, 1.5 Hz, 1H), 7.55 (dt, J=7.9, 1.9 Hz, 1H), 7.47 (t, J=7.9 Hz, 1H), 7.32 (dd, J=7.9, 5.3 Hz, 1H), 7.07 (dd, J=8.6, 2.6 Hz, 2H), 6.68 (dt, J=8.7, 2.6 Hz, 2H), 5.53 (dd, J=11.7, 9.7 Hz, 1H), 4.93 (d, J=9.7 Hz, 1H), 4.71 (d, J=15.4 Hz, 1H), 4.31 (d, J=15.4 Hz, 1H), 3.97 (m, 1H), 3.17 (dd, J=17.4, 13.0 Hz, 1H), 2.90 (dd, J=17.4, 5.0 Hz, 1H), 2.59 (s, 3H)

EXAMPLE 9
Synthesis of Compound 11

From methyl 3-(3-nitro-4-methoxymethoxyphenyl)-4-nitrobutyrate (140 mg, 0.43 mmol), 4-hydroxybenzaldehyde (52 mg, 0.43 mmol) and 3-aminomethylpyridine (0.087 mL, 0.86 mmol), Compound 11 (27 mg, yield 12%) was obtained in the same manner as in Example 1.

$^1$HNMR (DMSO-d$_6$, 300 MHz) δ9.67 (brs, 1H), 8.42 (d, J=4.7 Hz, 1H), 8.16 (br s, 1H), 8.05 (d, J=1.6 Hz, 1H), 7.66 (d, J=9.0 Hz, 1H), 7.37–7.45 (m, 2H), 7.29 (dd, J=4.7, 7.9 Hz, 1H), 7.09 (d, J=8.3 Hz, 2H), 6.68 (d, J=8.3 Hz, 2H), 5.76 (t, J=10.5 Hz, 1H), 5.34 (s, 2H), 4.80 (d, J=9.9 Hz, 1H), 4.70 (d, J=15.7 Hz, 1H), 3.90–4.05 (m, 2H), 3.39 (s, 3H), 3.11 (dd, J=17.2, 16.8 Hz, 1H), 2.76 (dd, J=16.8, 4.8 Hz, 1H)

EXAMPLE 10
Synthesis of Compound 12

From methyl 3-(3-cyanophenyl)-4-nitrobutyrate (248 mg, 1.0 mmol), 4-hydroxybenzaldehyde (100 mg, 0.80 mmol) and 3-aminomethylpyridine (0.20 mL, 2.0 mmol), Compound 12 (68 mg, yield 16%) was obtained in the same manner as in Example 1.

$^1$HNMR (DMSO-d$_6$, 300 MHz) δ9.66 (br s, 1H), 8.42 (d, J=3.3 Hz, 1H), 8.16 (s, 1H), 8.05 (s, 1H), 7.74–7.78 (m, 2H), 7.57 (t, J=7.8 Hz, 1H), 7.44 (d, J=7.8 Hz, 1H), 7.29 (dd, J=7.8, 4.6 Hz, 1H), 7.09 (d, J=8.4 Hz, 2H), 6.68 (d, J=8.4 Hz, 2H), 5.78 (dd, J=11.7, 8.2 Hz, 1H), 4.82 (d, J=9.9 Hz, 1H), 4.70 (d, J=15.8 Hz, 1H), 3.98–4.03 (m, 2H), 3.10 (dd, J=17.2, 16.8 Hz, 1H), 2.78 (dd, J=16.8, 4.8 Hz, 1H)

EXAMPLE 11
Synthesis of Compound 13

From methyl 3-(2-bromophenyl)-4-nitrobutyrate (300 mg, 1.0 mmol), 3-bromobenzaldehyde (0.10 mL, 1.0 mmol) and 3-aminomethylpyridine (0.20 mL, 2.0 mmol), Compound 13 (130 mg, yield 24%) was obtained in the same manner as in Example 1.

$^1$HNMR (DMSO-d$_6$, 300 MHz) δ8.36 (d, J=4.8 Hz, 1H), 8.07 (s, 1H), 7.78 (d, J=6.6 Hz, 1H), 7.66 (s, 1H), 7.62 (d, J=8.0 Hz, 1H), 7.42–7.48 (m, 1H), 7.31–7.36(m, 2H), 7.19–7.26 (m, 3H), 5.97 (dd, J=9.7, 11.6 Hz, 2H), 5.18 (d, J=9.7 Hz, 1H), 4.51 (d, J=15.6 Hz, 1H), 4.39–4.48 (m, 1H), 4.21 (d, J=15.6 Hz, 1H), 3.08 (dd, J=16.9, 12.7 Hz, 1H), 2.76 (dd, J=16.9, 5.2 Hz, 1H)

EXAMPLE 12
Synthesis of Compound 14

From methyl 3-(2-bromophenyl)-4-nitrobutyrate (300 mg, 1.0 mmol), 4-hydroxybenzaldehyde (100 mg, 0.80 mmol) and 3-aminomethylpyridine (0.20 mL, 2.0 mmol), Compound 14 (87 mg, yield 18%) was obtained in the same manner as in Example 1.

$^1$HNMR (DMSO-$d_6$, 300 MHz) δ9.62 (s, 1H), 8.38 (d, J=4.8 Hz, 1H), 8.11 (s, 1H), 7.78 (d, J=7.9 Hz, 1H), 7.61 (d, J=7.9 Hz, 1H), 7.39–7.46 (m, 2H), 7.22–7.27 (m, 2H), 7.14 (d, J=8.0 Hz, 2H), 6.64 (d, J=8.0 Hz, 2H), 5.89 (dd, J=11.0, 9.5 Hz, 1H), 4.94 (d, J=9.5 Hz, 1H), 4.47 (d, J=15.8 Hz, 1H), 4.38 (m, 1H), 4.18 (d, J=15.8 Hz, 1H), 3.05 (dd, J=16.8, 11.0 Hz, 1H), 2.74 (dd, J=16.8, 4.7 Hz, 1H)

EXAMPLE 13
Synthesis of Compound 15

From methyl 3-(2,3-dichlorophenyl)-4-nitrobutyrate (290 mg, 1.0 mmol), 4-hydroxybenzaldehyde (100 mg, 0.80 mmol) and 3-aminomethylpyridine (0.20 mL, 2.0 mmol), Compound 15 (96 mg, yield 20%) was obtained in the same manner as in Example 1.

$^1$HNMR (DMSO-$d_6$, 300 MHz) δ9.62 (s, 1H), 8.38 (dd, J=4.8, 1.5 Hz, 1H), 8.11 (d, J=2.0 Hz, 1H), 7.79 (d, J=7.5 Hz, 1H), 7.58 (d, J=7.0 Hz, 1H), 7.45 (d, J=7.9 Hz, 1H), 7.41 (m, 1H), 7.24 (d, J=7.9, 4.6 Hz, 1H), 7.12 (d, J=8.4 Hz, 2H), 6.64 (d, J=8.4 Hz, 2H), 5.87 (dd, J=11.2, 9.9 Hz, 1H), 4.94 (d, J=9.9 Hz, 1H), 4.47–4.59 (m, 2H), 4.16 (d, J=15.6 Hz, 1H), 3.05 (dd, J=17.1, 12.6 Hz, 1H), 2.80 (dd, J=17.1, 5.4 Hz, 1H)

EXAMPLE 14
Synthesis of Compound 16

From methyl 3-(3-chlorophenyl)-4-nitrobutyrate (260 mg, 1.0 mmol), 4-hydroxybenzaldehyde (120 mg, 1.0 mmol) and 3-aminomethylpyridine (0.20 mL, 2.0 mmol), Compound 16 (107 mg, yield 24%) was obtained in the same manner as in Example 1.

$^1$HNMR (DMSO-$d_6$, 300 MHz) δ9.65 (s, 1H), 8.42 (d, J=3.5 Hz, 1H), 8.16 (s, 1H), 7.59 (s, 1H), 7.43 (d, J=7.9 Hz, 1H), 7.30–7.36 (m, 3H), 7.28 (dd, J=17.6, 4.7 Hz, 1H), 7.09 (d, J=7.7 Hz, 2H), 6.68 (d, J=7.7 Hz, 2H), 5.73 (dd, J=11.6, 10.1 Hz, 1H), 4.79 (d, J=10.1 Hz, 1H), 4.69 (d, J=15.7 Hz, 1H), 3.91–3.90 (m, 2H), 3.15 (dd, J=16.9, 12.9 Hz, 1H), 2.75 (dd, J=16.9, 5.0 Hz, 1H)

EXAMPLE 15
Synthesis of Compound 17

From methyl 3-(2,3-dichlorophenyl)-4-nitrobutyrate (145 mg, 0.50 mmol), 2-hydroxybenzaldehyde (61 mg, 0.50 mmol) and 3-aminomethylpyridine (0.10 mL, 1.0 mmol), Compound 17 (46 mg, yield 20%) was obtained in the same manner as in Example 1.

$^1$HNMR (DMSO-$d_6$, 300 MHz) δ9.96 (s, 1H), 8.38 (d, J=5.7 Hz, 1H), 8.18 (s, 1H), 7.68 (d, J=7.3 Hz, 1H), 7.58 (d, J=8.1 Hz, 1H), 7.38–7.47 (m, 2H), 7.23–7.27 (m, 2H), 7.14 (t, J=7.3 Hz, 1H), 6.72–6.79 (m, 2H), 5.84 (t, J=11.8 Hz, 1H), 5.38 (d, J=8.1 Hz, 1H), 4.63 (d, J=15.4 Hz, 1H), 4.49 (m, 1H), 4.07 (d, J=15.4 Hz, 1H), 2.99 (dd, J=16.5, 13.9 Hz, 1H), 2.76 (dd, J=16.5, 3.5 Hz, 1H)

EXAMPLE 16
Synthesis of Compound 18

From methyl 3-(2,3-dichlorophenyl)-4-nitrobutyrate (145 mg, 0.50 mmol), 4-hydroxy-3-methoxybenzaldehyde (76 mg, 0.50 mmol) and 3-aminomethylpyridine (0.10 mL, 1.0 mmol), Compound 18 (27 mg, yield 11%) was obtained in the same manner as in Example 1.

$^1$HNMR (DMSO-$d_6$, 300 MHz) δ9.16 (s, 1H), 8.37 (dd, J=1.8, 5.0 Hz, 1H), 8.14 (d, J=1.8 Hz, 1H), 7.78 (d, J=8.9 Hz, 1H), 7.59 (dd, J=1.6, 7.9 Hz, 1H), 7.37–7.48 (m, 2H), 7.22 (dd, J=7.9, 4.8 Hz, 1H), 6.91 (s, 1H), 6.64 (s, 2H), 5.91 (dd, J=11.2, 10.0 Hz, 1H), 4.98 (d, J=10.0 Hz, 1H), 4.56 (m, 1H), 4.34 (br s, 2H), 3.59 (s, 3H), 3.02 (dd, J=16.5, 12.0 Hz, 1H), 2.81 (dd, J=16.5, 4.8 Hz, 1H)

EXAMPLE 17
Synthesis of Compound 19

From methyl 3-(3-nitrophenyl)-4-nitrobutyrate (134 mg, 0.50 mmol), 4-hydroxybenzaldehyde (61 mg, 0.50 mmol) and 3-aminomethylpyridine (0.10 mL, 1.0 mmol), Compound 19 (23 mg, yield 10%) was obtained in the same manner as in Example 1.

$^1$HNMR (DMSO-$d_6$, 300 MHz) δ9.67 (s, 1H), 8.44 (s, 1H), 8.43 (d, J=5.5 Hz, 1H), 8.17 (s, 1H), 8.15 (d, J=8.6 Hz, 1H), 7.88 (d, J=7.9 Hz, 1H), 7.66 (t, J=7.9 Hz, 1H), 7.45 (d, J=7.9 Hz, 1H), 7.29 (dd, J=7.9, 4.8 Hz, 1H), 7.12 (d, J=8.2 Hz, 2H), 6.68 (d, J=8.2 Hz, 2H), 5.88 (t, J=10.7 Hz, 1H), 4.83 (d, J=10.7 Hz, 1H), 4.70 (d, J=15.8 Hz, 1H), 4.18 (m, 1H), 3.95 (d, J=15.8 Hz, 1H), 3.22 (dd, J=17.6, 13.0 Hz, 1H), 2.80 (dd, J=17.6, 5.3 Hz, 1H)

EXAMPLE 18
Synthesis of Compound 20

From methyl 3-(3-bromophenyl)-4-nitrobutyrate (300 mg, 1.0 mmol), 4-hydroxy-3,5-dimethoxybenzaldehyde (182 mg, 1.0 mmol) and 3-aminomethylpyridine (0.20 mL, 2.0 mmol), Compound 20 (63 mg, yield 12%) was obtained in the same manner as in Example 1.

$^1$HNMR (DMSO-$d_6$, 300 MHz) δ8.39 (d, J=4.7 Hz, 1H), 8.19 (s, 1H), 7.71 (s, 1H), 7.49 (d, J=7.4 Hz, 1H), 7.30–7.43 (m, 4H), 7.25 (dd, J=7.4, 4.8 Hz, 1H), 6.53 (s, 2H), 5.77 (t, J=10.5 Hz, 1H), 4.85 (d, J=9.7 Hz, 1H), 4.50 (d, J=15.4 Hz, 1H), 4.23 (d, J=15.4 Hz, 1H), 3.96 (m, 1H), 3.64 (s, 6H), 3.15 (dd, J=17.2, 13.0 Hz, 1H), 2.78 (dd, J=17.2, 4.8 Hz, 1H)

EXAMPLE 19
Synthesis of Compound 21

From methyl 3-(3-methylphenyl)-4-nitrobutyrate (237 mg, 1.0 mmol), 4-hydroxybenzaldehyde (100 mg, 0.80 mmol) and 3-aminomethylpyridine (0.20 mL, 2.0 mmol), Compound 21 (47 mg, yield 11%) was obtained in the same manner as in Example 1.

$^1$HNMR (DMSO-$d_6$, 300 MHz) δ9.63 (s, 1H), 8.42 (dd, J=5.0, 1.8 Hz, 1H), 8.15 (d, J=1.8 Hz, 1H), 7.44 (d, J=7.8 Hz, 1H), 7.28 (dd, J=7.8, 4.9 Hz, 1H), 7.20–7.23 (m, 3H), 7.08–7.11 (m, 3H), 6.67 (d, J=8.4 Hz, 2H), 5.65 (dd, J=11.8, 9.8 Hz, 1H), 4.79 (d, J=9.8 Hz, 1H), 4.70 (d, J=15.4 Hz, 1H), 3.93 (d, J 15.4 Hz, 1H), 3.83 (m, 1H), 3.15 (dd, J=17.3, 12.6 Hz, 1H), 2.70 (dd, J=17.3, 4.9 Hz, 1H), 2.28 (s, 3H)

EXAMPLE 20
Synthesis of Compound 22

From methyl 3-(2-bromophenyl)-4-nitrobutyrate (150 mg, 0.50 mmol), 3,4-dihydroxybenzaldehyde (69 mg, 0.50 mmol) and 3-aminomethylpyridine (0.10 mL, 1.0 mmol), Compound 22 (47 mg, yield 19%) was obtained in the same manner as in Example 1.

$^1$HNMR (DMSO-$d_6$, 300 MHz) δ9.23 (s, 1H), 8.95 (s, 1H), 8.43 (dd, J=4.6, 1.5 Hz, 1H), 8.18 (d, J=2.0 Hz, 1H), 7.79 (d, J=7.2 Hz, 1H), 7.61 (dd, J=7.8, 1.1 Hz, 1H), 7.41–7.47 (m, 2H), 7.29 (dd, J=7.8, 4.7 Hz, 1H), 7.22 (dt, J=7.8, 1.5 Hz, 1H), 6.75 (d, J=2.0 Hz, 1H), 6.64 (d, J=8.1 Hz, 1H), 6.56 (dd, J=8.1, 2.0 Hz, 1H), 5.84 (dd, J=11.3, 9.8 Hz, 1H), 4.80 (d, J=9.8 Hz, 1H), 4.65 (d, J=15.6 Hz, 1H), 4.35 (m, 1H), 3.99 (d, J=15.6 Hz, 1H), 3.02 (dd, J=16.9, 12.5 Hz, 1H), 2.72 (dd, J=16.9, 4.6 Hz, 1H)

EXAMPLE 21
Synthesis of Compound 23

From methyl 3-(3-chlorophenyl)-4-nitrobutyrate (130 mg, 0.50 mmol), 3,4-dihydroxybenzaldehyde (69 mg, 0.50 mmol) and 3-aminomethylpyridine (0.10 mL, 1.0 mmol), Compound 23 (27 mg, yield 12%) was obtained in the same manner as in Example 1.

$^1$HNMR (DMSO-d$_6$, 300 MHz) δ9.25 (s, 1H), 8.99 (s, 1H), 8.45 (d, J=3.3 Hz, 1H), 8.31 (s, 1H), 7.60 (s, 1H), 7.49 (dt, J=7.8, 1.8 Hz, 1H), 7.30–7.39 (m, 4H), 6.71 (d, J=8.1 Hz, 1H), 6.67 (d, J=8.1 Hz, 1H), 6.49 (dd, J=8.1, 2.0 Hz, 1H), 5.69 (dd, J=11.9, 9.9 Hz, 1H), 4.86 (d, J=15.4 Hz, 1H), 4.67(d, J=9.9 Hz, 1H), 3.92 (m, 1H), 3.79 (d, J=15.4 Hz, 1H), 3.15 (dd, J=17.0, 13.2 Hz, 1H), 2.75 (dd, J=17.0, 4.6 Hz, 1H)

EXAMPLE 22

Synthesis of Compound 24

Palladium-carbon (15 mg) was added to a solution (3.0 mL) of Compound 19 (45 mg, 0.10 mmol) in DMF, followed by stirring under a hydrogen atmosphere at room temperature for 6 hours. Next, the reaction solution was filtered through celite to remove the catalyst, and purified by silica gel column chromatography (eluted with chloroform/methanol=19/1) to give Compound 24 (32 mg, yield 73%).

$^1$HNMR (DMSO-d$_6$, 300 MHz) δ9.62 (s, 1H) , 8.41 (d, J=3.4 Hz, 1H), 8.29–8.33 (m, 2H), 7.95 (br s, 1H), 7.45 (d, J=7.9 Hz, 1H), 7.27 (dd, J=7.9, 3.1 Hz, 1H), 7.08–7.13 (m, 3H), 6.64–6.85 (m, 5H), 5.60 (dd, J=11.5, 10.0 Hz, 1H), 4.77 (d, J=10.0 Hz, 1H), 4.69 (d, J=15.6 Hz, 1H), 3.94 (d, J=15.6 Hz, 1H), 3.78 (m, 1H), 3.15 (dd, J=16.8, 13.6 Hz, 1H), 2.75 (dd, J=16.8, 4.8 Hz, 1H)

EXAMPLE 23

Synthesis of Compound 25

Acetyl chloride (0.0047 mL, 0.066 mmol) and triethylamine (0.018 mL, 0.132 mmol) were added under ice-cooling to a solution of Compound 14 (16 mg, 0.033 mmol) in DMF, followed by stirring at room temperature for 1 hour. After adding water thereto, the reaction solution was extracted with chloroform and the organic layer was dried over sodium sulfate. After evaporating the solvent under reduced pressure, the residue was purified by silica gel column chromatography (eluted with chloroform/methanol=97/3) to give Compound 25 (12 mg, yield 72%).

$^1$HNMR (DMSO-d$_6$, 300 MHz) δ8.41 (d, J=4.7 Hz, 1H), 8.19 (br s, 1H), 7.73 (br s, 1H), 7.48 (d, J=8.1 Hz, 1H), 7.23–7.43 (m, 6H), 7.09 (d, J=8.1 Hz, 2H), 5.79 (dd, J=11.8, 9.7 Hz, 1H), 4.98 (d, J=9.7 Hz, 1H), 4.65 (d, J=15.6 Hz, 1H), 3.94–4.03 (m, 2H), 3.21 (dd, J=17.2, 12.5 Hz, 1H), 2.78 (dd, J=17.2, 4.8 Hz, 1H), 2.05 (s, 3H)

EXAMPLE 24

Synthesis of Compound 26

From Compound 14 (16 mg, 0.033 mmol), nicotinoyl chloride hydrochloride (12 mg, 0.066 mmol) and triethylamine (0.018 mL, 0.132 mmol), Compound 26 (20 mg, yield 100%) was obtained in the same manner as in Example 23.

$^1$HNMR (DMSO-d$_6$, 300 MHz) δ9.25 (s, 1H), 8.90 (d, J=4.8 Hz, 1H), 8.43–8.48 (m, 2H), 8.24 (s, 1H), 7.75 (s, 1H), 7.65 (dd, J=8.1, 3.4 Hz, 1H), 7.42–7.51 (m, 5H), 7.28–7.34 (m, 4H), 5.83 (dd, J=11.2, 10.1 Hz, 1H), 5.02 (d, J=10.1 Hz, 1H), 4.72 (d, J=15.6 Hz, 1H), 3.96–4.05 (m, 2H), 3.18 (dd, J=16.7, 12.1 Hz, 1H), 2.79 (dd, J=16.7, 5.1 Hz, 1H)

EXAMPLE 25

Synthesis of Compound 27

From Compound 24 (20 mg, 0.046 mmol), acetyl chloride (0.0066 mL, 0.092 mmol) and triethylamine (0.010 mL, 0.1 mmol), Compound 27 (4.2 mg, yield 16%) was obtained in the same manner as in Example 23.

$^1$HNMR (DMSO-d$_6$, 300 MHz) δ8.42 (d, J=4.2 Hz, 1H), 8.19 (s, 1H), 7.61 (s, 1H), 7.28–7.40 (m, 6H), 7.09 (d, J=8.4 Hz, 2H), 5.79 (dd, J=10.6, 9.7 Hz, 1H), 4.99 (d, J=9.7 Hz, 1H), 4.67 (d, J=15.8 Hz, 1H), 3.97–4.10 (m, 2H), 3.18 (dd, J=16.2, 11.7 Hz, 1H), 2.78 (dd, J=16.2, 4.0 Hz, 1H), 2.26 (s, 6H), 2.00 (s, 3H)

EXAMPLE 26

Synthesis of Compound 28

Palladium-carbon (10%, 15 mg) was added to a solution (5.0 mL) of Compound 19 (15 mg, 0.034 mmol) in DMF, followed by stirring under a hydrogen atmosphere at 50° C. for 6 hours. Next, the reaction solution was filtered through celite to remove the catalyst, and purified by silica gel column chromatography (eluted with chloroform/methanol=19/1) to give Compound 28 (13 mg, yield 87%).

$^1$HNMR (DMSO-d$_6$, 300 MHz) δ9.61 (s, 1H) , 8.41 (d, J=4.0 Hz, 1H), 8.14 (s, 1H), 7.41 (d, J=7.1 Hz, 1H), 7.27 (dd, J=7.1, 4.9 Hz, 1H), 7.09 (d, J=8.3 Hz, 2H), 6.95 (t, J=7.6 Hz, 1H), 6.65 (d, J=8.3 Hz, 2H), 6.56 (d, J=7.1 Hz, 1H), 6.43–6.48 (m, 2H), 5.52 (dd, J=12.3, 10.2 Hz, 1H), 5.05 (br s, 2H), 4.75 (d, J=10.2 Hz, 1H), 4.68 (d, J=15.6 Hz, 1H), 3.94 (d, J=15.6 Hz, 1H), 3.66 (m, 1H), 3.10 (dd, J=15.9, 12.4 Hz, 1H), 2.69 (dd, J=15.9, 3.8 Hz, 1H)

EXAMPLE 27

Synthesis of Compound 29

From methyl 3-(2-chlorophenyl)-4-nitrobutyrate (1.86 g, 7.2 mmol), 3,4-dihydroxybenzaldehyde (890 mg, 7.2 mmol) and 3-aminomethylpyridine (1.4 mL, 14 mmol), Compound 29 (1.22 g, yield 37%) was obtained in the same manner as in Example 1.

$^1$HNMR (DMSO-d$_6$, 300 MHz) δ9.23 (s, 1H), 8.96 (s, 1H), 8.42 (dd, J=4.8, 1.7 Hz, 1H), 8.19 (s, 1H), 7.80 (d, J=6.8 Hz, 1H), 7.27–7.48 (m, 5H), 6.74 (d, J=1.6 Hz, 1H), 6.64 (d, J=8.1 Hz, 1H), 6.54 (dd, J=8.1, 1.6 Hz, 1H), 5.81 (dd, J=11.3, 9.9 Hz, 1H), 4.80 (d, J=9.9 Hz, 1H), 4.69 (d, J=15.5 Hz, 1H), 4.39 (m, 1H), 3.98 (d, J=15.5 Hz, 1H), 3.05 (dd, J=16.7, 12.7 Hz, 1H), 2.74 (dd, J=16.7, 4.9 Hz, 1H)

EXAMPLE 28

Synthesis of Compound 30

From methyl 3-(2-methylphenyl)-4-nitrobutyrate (240 mg, 1.0 mmol), 3,4-dihydroxybenzaldehyde (138 mg; 1.0 mmol) and 3-aminomethylpyridine (0.20 mL, 2.0 mmol), Compound 30 (70 mg, yield 16%) was obtained in the same manner as in Example 1.

$^1$HNMR (DMSO-d$_6$, 300 MHz) δ9.21 (s, 1H), 8.94 (s, 1H), 8.42 (dd, J=4.6, 1.6 Hz, 1H), 8.20 (d, J=2.0 Hz, 1H), 7.64 (d, J=7.7 Hz, 1H), 7.49 (dt, J=7.7, 2.0 Hz, 1H), 7.28 (dt, J=7.7, 4.7 Hz, 1H), 7.19 (m, 1H), 7.08–7.12 (m, 2H), 6.73 (d, J=2.0 Hz, 1H), 6.64 (d, J=8.4 Hz, 1H), 6.53 (dd, J=8.4, 2.0 Hz, 1H), 5.69 (dd, J=11.4, 9.8 Hz, 1H), 4.75 (d, J=9.8 Hz, 1H), 4.74 (d, J=15.4 Hz, 1H), 4.14 (m, 1H), 3.93 (d, J=15.4 Hz, 1H), 3.00 (dd, J=17.2, 12.0 Hz, 1H), 2.71 (dd, J=17.2, 4.8 Hz, 1H), 2.08 (s, 3H)

EXAMPLE 29

Synthesis of Compound 31

From methyl 3-(2,6-dichlorophenyl)-4-nitrobutyrate (590 mg, 2.0 mmol), 3,4-dihydroxybenzaldehyde (262 mg, 1.9 mmol) and 3-aminomethylpyridine (0.40 mL, 4.0 mmol), Compound 31 (86 mg, yield 8.8%) was obtained in the same manner as in Example 1.

$^1$HNMR (DMSO-d$_6$, 300 MHz) δ9.21 (s, 1H), 9.03 (s, 1H), 8.42 (d, J=5.9 Hz, 1H), 8.21 (br s, 1H), 7.47–7.53 (m, 3H), 7.27–7.39 (m, 2H), 6.65–6.67 (m, 2H), 6.53 (d, J=7.3 Hz, 1H), 5.97 (dd, J=11.7, 9.7 Hz, 1H), 4.93 (d, J=9.7 Hz, 1H), 4.70–4.86 (m, 2H), 3.99 (d, J=15.1 Hz, 1H), 3.47 (dd, J=16.5, 13.8 Hz, 1H), 2.84 (dd, J=16.5, 4.6 Hz, 1H)

EXAMPLE 30
Synthesis of Compound 32

From methyl 3-(2-bromophenyl)-4-nitrobutyrate (300 mg, 1.0 mmol), 4-methoxybenzaldehyde (0.10 mL, 0.9 mmol) and 3-aminomethylpyridine (0.20 mL, 2.0 mmol), Compound 32 (220 mg, yield 45%) was obtained in the same manner as in Example 1.

$^1$HNMR (DMSO-$d_6$, 300 MHz) δ8.38 (dd, J=4.8, 1.5 Hz, 1H), 8.11 (d, J=1.5 Hz, 1H), 7.78 (d, J=7.0 Hz, 1H), 7.61 (dd, J=8.1, 1.1 Hz, 1H), 7.44 (t, J=7.0 Hz, 1H), 7.37 (d, J=8.1 Hz, 1H), 7.20–7.29 (m, 4H), 6.83 (d, J=8.8 Hz, 2H), 5.92 (dd, J=11.5, 10.1 Hz, 1H), 5.02 (d, J=10.1 Hz, 1H), 4.35–4.48 (m, 2H), 4.21 (d, J=15.4 Hz, 1H), 3.70 (s, 3H), 3.04 (dd, J=16.8, 12.8 Hz, 1H), 2.75 (dd, J=16.8, 5.2 Hz, 1H)

EXAMPLE 31
Synthesis of Compound 33

From methyl 3-(2-bromophenyl)-4-nitrobutyrate (300 mg, 1.0 mmol), 2-chloro-4-hydroxybenzaldehyde (141 mg, 0.9 mmol) and 3-aminomethylpyridine (0.20 mL, 2.0 mmol), Compound 33 (143 mg, yield 28%) was obtained in the same manner as in Example 1.

$^1$HNMR (DMSO-$d_6$, 300 MHz) δ10.16 (s, 1H), 8.39 (dd, J=4.8, 1.4 Hz, 1H), 8.12 (d, J=1.7 Hz, 1H), 7.76 (d, J=7.3 Hz, 1H), 7.62 (dd, J=8.0, 1.1 Hz, 1H), 7.40–7.46 (m, 3H), 7.20–7.27 (m, 2H), 6.73 (d, J=2.4 Hz, 1H), 6.64 (dd, J=8.0, 2.4 Hz, 1H), 5.87 (dd, J=11.2, 10.1 Hz, 1H), 5.45 (d, J=10.1 Hz, 1H), 4.42–4.51 (m, 2H), 4.30 (d, J=15.4 Hz, 1H), 3.04 (dd, J=16.7, 13.0 Hz, 1H), 2.77 (dd, J=16.7, 5.1 Hz, 1H)

EXAMPLE 32
Synthesis of Compound 34

From methyl 3-(2-bromophenyl)-4-nitrobutyrate (300 mg, 1.0 mmol), 3,4-dihydroxy-5-methoxybenzaldehyde (151 mg, 0.9 mmol) and 3-aminomethylpyridine (0.20 mL, 2.0 mmol), Compound 34 (134 mg, yield 25%) was obtained in the same manner as in Example 1.

$^1$HNMR (DMSO-$d_6$, 300 MHz) δ8.95 (s, 1H), 8.47 (s, 1H), 8.39 (dd, J=4.6, 1.8 Hz, 1H), 8.20 (d, J=1.8 Hz, 1H), 7.78 (d, J=7.0 Hz, 1H), 7.61 (dd, J=8.1, 1.1 Hz, 1H), 7.42–7.47 (m, 2H), 7.20–7.28 (m, 2H), 6.47 (d, J=1.8 Hz, 1H), 6.36 (d, J=1.8 Hz, 1H), 5.88 (dd, J=11.4, 10.1 Hz, 1H), 4.85 (d, J=10.1 Hz, 1H), 4.45 (d, J=15.8 Hz, 1H), 4.37 (dt, J=12.6, 5.1 Hz, 1H), 4.24 (d, J=15.8 Hz, 1H), 3.59 (s, 3H), 3.01 (dd, J=17.0, 12.6 Hz, 1H), 2.75 (dd, J=17.0, 5.1 Hz, 1H)

EXAMPLE 33
Synthesis of Compound 35

From Compound 22 (50 mg, 0.10 mmol), N,N-dimethylcarbamoyl chloride (0.032 mL, 0.5 mmol) and triethylamine (0.1 mL, 1.0 mmol), Compound 35 (14 mg, yield 22%) was obtained in the same manner as in Example 23.

$^1$HNMR (DMSO-$d_6$, 300 MHz) δ8.41 (d, J=5.3 Hz, 1H), 8.28 (d, J=2.6 Hz, 1H), 7.76 (d, J=7.2 Hz, 1H), 7.62 (d, J=8.1 Hz, 1H), 7.33–7.47 (m, 3H), 7.15–7.26 (m, 4H), 5.93 (dd, J=11.3, 10.1 Hz, 1H), 5.10 (d, J=9.7 Hz, 1H), 4.57 (d, J=15.6 Hz, 1H), 4.40 (m, 1H), 4.08 (d, J=15.6 Hz, 1H), 3.00 (s, 3H), 2.99 (dd, J=16.5, 12.1 Hz, 1H), 2.98 (s, 3H), 2.92 (s, 3H), 2.90 (s, 3H), 2.78 (dd, J=16.5, 4.2 Hz, 1H)

EXAMPLE 34
Synthesis of Compound 36

From methyl 3-(2,5-dichlorophenyl)-4-nitrobutyrate (210 mg, 0.72 mmol), 3,4-dihydroxybenzaldehyde (99 mg, 0.72 mmol) and 3-aminomethylpyridine (0.14 mL, 1.4 mmol), Compound 36 (92 mg, yield 26%) was obtained in the same manner as in Example 1.

$^1$HNMR (DMSO-$d^6$, 400 MHz) δ9.22 (s, 1H), 8.93 (s, 1H), 8.41 (dd, J=4.8, 1.6 Hz, 1H), 8.18 (d, J=1.6 Hz, 1H), 8.00 (d, J=1.6 Hz, 1H), 7.48 (d, J=8.6 Hz, 1H), 7.45 (dt, J=7.8, 1.9 Hz, 1H), 7.38 (dd, J=9.8, 2.5 Hz, 1H), 7.28 (ddd, J=0.7, 4.9, 7.8 Hz, 1H), 6.73 (d, J=2.0 Hz, 1H), 6.64 (d, J=8.1 Hz, 1H), 6.53 (dd, J=8.1, 2.0 Hz, 1H), 5.86 (dd, J=11.5, 9.8 Hz, 1H), 4.81 (d, J=9.8 Hz, 1H), 4.65 (d, J=15.6 Hz, 1H), 4.39 (dt, J=12.7, 4.9 Hz, 1H), 4.00 (d, J=15.6 Hz, 1H), 3.02 (dd, J=17.3, 12.7 Hz, 1H), 2.75 (dd, J=17.3, 4.9 Hz, 1H)

EXAMPLE 35
Synthesis of Compound 37

From methyl 3-(3,5-dichlorophenyl)-4-nitrobutyrate (116 mg, 0.40 mmol), 3,4-dihydroxybenzaldehyde (55 mg, 0.40 mmol) and 3-aminomethylpyridine (0.80 mL, 0.80 mmol), Compound 37 (29 mg, yield 15%) was obtained in the same manner as in Example 1.

$^1$HNMR (DMSO-$d_6$, 300 MHz) δ9.24 (s, 1H), 8.98 (s, 1H), 8.45 (dd, J=4.9, 1.6 Hz, 1H), 8.22 (d, J=1.6 Hz, 1H), 7.58 (d, J=2.0 Hz, 2H), 7.53 (t, J=1.7 Hz, 1H), 7.48 (td, J=7.8, 2.0 Hz, 1H), 7.32 (ddd, J=7.8, 4.7, 0.7 Hz, 1H), 6.71 (d, J=2.2 Hz, 1H), 6.67 (dd, J=8.0, 2.2 Hz, 1H), 6.48 (dd, J=8.0, 2.2 Hz, 1H), 5.73 (dd, J=11.7, 9.7 Hz, 1H), 4.86 (d, J=15.6 Hz, 1H), 4.67 (d, J=9.7 Hz, 1H), 3.97 (dd, J=13.0, 4.7 Hz, 1H), 3.79 (d, J=15.6 Hz, 1H), 3.11 (dd, J=17.1, 13.0 Hz, 1H), 2.76 (dd, J=17.1, 4.9 Hz, 1H)

EXAMPLE 36
Synthesis of Compound 38

From methyl 3-(2-trifluoromethylphenyl)-4-nitrobutyrate (319 mg, 1.23 mmol), 3,4-dihydroxybenzaldehyde (169 mg, 1.23 mmol) and 3-aminomethylpyridine (0.256 mL, 2.45 mmol), Compound 38 (190 mg, yield 30%) was obtained in the same manner as in Example 1.

$^1$HNMR (DMSO-$d_6$, 400 MHz) δ9.19 (br s, 1H), 8.91 (br s, 1H), 8.41 (dd, J=4.6, 1.7 Hz, 1H), 8.16 (m, 1H), 8.10 (d, J=7.8 Hz, 1H), 7.71–7.76 (m, 2H), 7.51 (t, J=7.6 Hz, 1H), 7.43 (dt, J=8.6, 2.2 Hz, 1H), 6.71 (ddd, J=7.8, 4.9, 0.7 Hz, 1H), 6,77 (d, J=2.0 Hz, 1H), 6.77 (d, J=8.0 Hz, 1H), 6.59 (dd, J=2.0, 8.0 Hz, 1H), 5.98 (dd, J=10.9, 10.0 Hz, 1H), 4.84 (d, J=10.0 Hz, 1H), 4.56 (d, J=16.6 Hz, 1H), 4.07–4.14 (m, 2H), 3.08 (dd, J=17.2, 4.4 Hz, 1H), 2.70 (dd, J=17.2, 5.1 Hz, 1H)

EXAMPLE 37
Synthesis of Compounds 39 and 84

From methyl 3-(3-fluorophenyl)-4-nitrobutyrate (220 mg, 0.91 mmol), 3,4-dihydroxybenzaldehyde (124 mg, 0.90 mmol) and 3-aminomethylpyridine (0.19 mL, 1.82 mmol), Compound 39 (26 mg, yield 6.5%) and Compound 84 (87 mg, yield 46%) were obtained in the same manner as in Example 1.

Compound 39

$^1$HNMR (DMSO-$d_6$, 300 MHz) δ9.24 (br s, 1H), 9.01 (br s, 1H), 8.45 (dd, J=4.7, 1.7 Hz, 1H), 8.22 (br s, 1H), 7.51 (dt, J=7.9, 1.6 Hz, 1H), 7.30–7.41 (m, 3H), 7.23 (d, J=7.9 Hz, 1H), 7.11 (td, J=8.5, 2.6 Hz, 1H), 6.71 (d, J=2.0 Hz, 1H), 6.66 (d, J=8.0 Hz, 1H), 6.49 (dd, J=2.0, 8.0 Hz, 1H), 5.67 (dd, J=11.6, 9.9 Hz, 1H), 4.87 (d, J=15.4 Hz, 1H), 4.67 (d, J=9.9 Hz, 1H), 3.93 (m, 1H), 3.78 (d, J=15.4 Hz, 1H), 3.15 (dd, J=17.0, 13.0 Hz, 1H), 2.74 (dd, J=17.0, 4.4 Hz, 1H)

Compound 84

$^1$HNMR (DMSO-$d_6$, 300 MHz) δ8.47–8.51 (m, 2H), 8.35 (dd, J=4.8, 1.6 Hz, 1H), 8.11 (d, J=2.4 Hz, 1H), 7.80 (td, J=1.8, 7.9 Hz, 1H), 7.22–7.44 (m, 6H), 7.13 (td, J=10.7, 1.8 Hz, 1H), 5.85 (dd, J=9.9, 11.4 Hz, 1H), 5.09 (d, J=10.1 Hz, 1H), 4.50 (d, J=15.7 Hz, 1H), 4.26 (d, J=15.7 Hz, 1H), 4.05 (m, 1H), 3.18 (dd, J=17.3, 12.6 Hz, 1H), 2.80 (dd, J=17.3, 5.0 Hz, 1H)

EXAMPLE 38
Synthesis of Compound 40

From methyl 3-(2,3-dichlorophenyl)-4-nitrobutyrate (291 mg, 1.0 mmol), 3,4-dihydroxybenzaldehyde (140 mg, 1.0 mmol) and 3-aminomethylpyridine (0.20 mL, 2.0 mmol), Compound 40 (107 mg, yield 22%) was obtained in the same manner as in Example 1.

$^1$HNMR (DMSO-$d_6$, 300 MHz) δ9.24 (br s, 1H), 8.96 (br s, 1H), 8.41 (d, J=4.4 Hz, 1H), 8.18 (br s, 1H), 7.82 (d, J=7.9 Hz, 1H), 7.58 (d, J=7.9 Hz, 1H), 7.46 (t, J=7.9 Hz, 1H), 7.43 (t, J=7.9 Hz, 1H), 7.28 (dd, J=7.7, 4.8 Hz, 1H), 6.74 (s, 1H), 6.64 (d, J=8.2 Hz, 1H), 6.55 (d, J=8.2 Hz, 1H), 5.84 (dd, J=11.2, 10.0 Hz, 1H), 4.82 (d, J=10.0 Hz, 1H), 4.67 (d, J=15.6 Hz, 1H), 4.49 (m, 1H), 3.99 (d, J=15.6 Hz, 1H), 3.13 (dd, J=17.1, 12.7 Hz, 1H), 2.74 (dd, J=17.1, 5.1 Hz, 1H)

EXAMPLE 39
Synthesis of Compound 41

From methyl 3-(2,3,5-trichlorophenyl)-4-nitrobutyrate (325 mg, 1.0 mmol), 3,4-dihydroxybenzaldehyde (140 mg, 1.0 mmol) and 3-aminomethylpyridine (0.20 mL, 2.0 mmol), Compound 41 (72 mg, yield 14%) was obtained in the same manner as in Example 1.

$^1$HNMR (DMSO-$d_6$, 300 MHz) δ9.26 (br s, 1H), 8.96 (br s, 1H), 8.41 (dd, J=4.8, 1.7 Hz, 1H), 8.18 (d, J=1.7 Hz, 1H), 8.04 (d, J=2.4 Hz, 1H), 7.81 (d, J=2.4 Hz, 1H), 7.45 (d, J=7.8 Hz, 1H), 7.28 (dd, J=7.8, 4.8 Hz, 1H), 6.73 (d, J=2.4 Hz, 1H), 6.64 (d, J=8.0 Hz, 1H), 6.53 (d, J=8.0 Hz, 1H), 5.88 (dd, J=11.6, 10.0 Hz, 1H), 4.82 (d, J=10.0 Hz, 1H), 4.63 (d, J=15.5 Hz, 1H), 4.50 (m, 1H), 4.01 (d, J=15.5 Hz, 1H), 2.99 (dd, J=16.7, 13.6 Hz, 1H), 2.78 (dd, J=16.7, 5.3 Hz, 1H)

EXAMPLE 40
Synthesis of Compound 42

From methyl 3-[2-(1,3-dioxolan-2-yl)phenyl]-4-nitrobutyrate (280 mg, 0.96 mmol), 3,4-dihydroxybenzaldehyde (132 mg, 0.96 mmol) and 3-aminomethylpyridine (0.20 mL, 1.9 mmol), Compound 42 (162 mg, yield 34%) was obtained in the same manner as in Example 1.

$^1$HNMR (DMSO-$d_6$, 300 MHz) δ9.00 (br s, 2H), 8.42 (dd, J=4.7, 1.5 Hz, 1H), 8.19 (d, J=1.9 Hz, 1H), 7.76 (d, J=7.5 Hz, 1H), 7.38–7.49 (m, 3H), 7.26–7.32 (m, 2H), 6.76 (d, J=2.0 Hz, 1H), 6.64 (d, J=8.1 Hz, 1H), 6.55 (dd, J=8.1, 2.0 Hz, 1H), 5.98 (s, 1H), 5.83 (dd, J=11.6, 9.7 Hz, 1H), 4.77 (d, J=9.7 Hz, 1H), 4.70 (d, J=15.4 Hz, 1H), 3.94–4.08 (m, 6H), 3.01 (dd, J=17.1, 12.9 Hz, 1H), 2.69 (dd, J=17.1, 4.7 Hz, 1H)

EXAMPLE 41
Synthesis of Compound 43

Methyl 3-(2-bromophenyl)-4-nitrobutyrate (425 mg, 1.4 mmol), m-nitrobenzaldehyde (213 mg, 1.4 mmol) and 3-aminomethylpyridine (0.28 mL, 2.8 mmol) were stirred in ethanol at room temperature for 24 hours. After evaporating ethanol under reduced pressure, the residue was purified by silica gel column chromatography (eluted with chloroform/methanol=99/1) to give Compound 43 (264 mg, yield 37%).

$^1$HNMR (CDCl$_3$, 300 MHz) δ8.53–8.51 (m, 1H), 8.26–8.23 (m, 1H), 8.12–8.06 (m, 2H), 7.59–7.55 (m, 2H), 7.50 (d, J=7.9 Hz, 1H), 7.44 (d, J=7.9 Hz, 1H), 7.32–7.23 (m, 3H), 7.18–7.12 (m, 1H), 5.35 (t, J=9.4 Hz, 1H), 5.11–5.05 (m, 2H), 4.49–4.40 (m, 1H), 4.00 (d, J=15.0 Hz, 1H), 3.12 (dd, J=18.0, 5.1 Hz, 1H), 2.96–2.86 (m, 1H)

EXAMPLE 42
Synthesis of Compound 44

From methyl 3-(3,5-dibromophenyl)-4-nitrobutyrate (892 mg, 2.3 mol), 3,4-dihydroxybenzaldehyde (317 mg, 2.3 mmol) and 3-aminomethylpyridine (0.47 mL, 2.0 mmol), Compound 44 (67 mg, yield 12%) was obtained in the same manner as in Example 1.

$^1$HNMR (DMSO-$d_6$, 300 MHz) δ9.24 (br s, 1H), 8.99 (br s, 1H), 8.45 (d, J=3.5 Hz, 1H), 8.22 (br s, 1H), 7.74 (s, 2H), 7.73 (s, 1H), 7.47 (d, J=7.9 Hz, 1H), 7.31 (dd, J=7.9, 4.8 Hz, 1H), 6.71 (s, 1H), 6.68 (d, J=8.2 Hz, 1H), 6.55 (d, J=8.2 Hz, 1H), 5.74 (dd, J=11.4, 9.8 Hz, 1H), 4.88 (d, J=15.4 Hz, 1H), 4.64 (d, J=9.8 Hz, 1H), 3.93 (m, 1H), 3.78 (d, J=15.4 Hz, 1H), 3.11 (dd, J=17.2, 12.7 Hz, 1H), 2.74 (dd, J=17.2, 4.8 Hz, 1H)

EXAMPLE 43
Synthesis of Compound 45

2 mol/L hydrochloric acid (1 mL) was added to a solution (10 mL) of Compound 42 (162 mg, 0.24 mmol) in acetone, followed by stirring at room temperature for 12 hours. Next, the reaction solution was neutralized with a saturated aqueous solution of hydrogen bicarbonate and extracted with a 10% methanol-chloroform solution. The organic layer was dried over sodium sulfate. After evaporating the solvent under reduced pressure, the residue was purified by silica gel column chromatography (eluted with chloroform/methanol=50/1) to give Compound 45 (24 mg, yield 22%).

$^1$HNMR (DMSO-$d_6$, 300 MHz) δ10.36 (s, 1H), 9.24 (br s, 1H), 8.98 (br s, 1H), 8.44 (dd, J=4.8, 1.5 Hz, 1H), 8.22 (d, J=1.5 Hz, 1H), 7.94 (d, J=7.9 Hz, 1H), 7.84 (dd, J=7.9, 1.2 Hz, 1H), 7.71 (td, J=7.5, 1.2 Hz, 1H), 7.47–7.74 (m, 2H), 7.31 (dd, J=4.8, 7.9 Hz, 1H), 6.74 (d, J=1.9 Hz, 1H), 6.65 (d, J=8.2 Hz, 1H), 6.53 (dd, J=8.2, 1.9 Hz, 1H), 5.82 (dd, J=10.5, 9.9 Hz, 1H), 5.08 (m, 1H), 4.80 (d, J=16.6 Hz, 1H), 4.75 (d, J=10.1 Hz, 1H), 3.90 (d, J=16.6 Hz, 1H), 3.14 (dd, J=16.9, 12.8 Hz, 1H), 2.74 (dd, J=16.9, 5.0 Hz, 1H)

EXAMPLE 44
Synthesis of Compound 46

From Compound 22 (50 mg, 0.10 mmol), acetyl chloride (0.022 mL, 0.30 mmol) and triethylamine (0.5 mL, 5.0 mmol), Compound 46 (16 mg, yield 28%) was obtained in the same manner as in Example 23.

$^1$HNMR (CDCl$_3$, 300 MHz) δ8.56 (dd, J=4.7, 1.7 Hz, 1H), 8.39 (d, J=1.7 Hz, 1H), 7.56 (dd, J=7.9, 1.1 Hz, 1H), 7.48 (dt, J=7.9, 1.7 Hz, 1H), 7.11–7.33 (m, 5H), 7.05 (d, J=2.1 Hz, 1H), 7.01 (dd, J=8.3, 2.1 Hz, 1H), 5.34 (d, J=15.1 Hz, 1H), 5.25 (dd, J=10.6, 8.5 Hz, 1H), 4.92 (d, J=8.5 Hz, 1H), 4.36 (m, 1H), 3.80 (d, J=15.1 Hz, 1H), 3.04 (dd, J=17.6, 5.0 Hz, 1H), 2.79 (m, 1H), 2.31 (s, 6H)

EXAMPLE 45
Synthesis of Compound 47

From Compound 22 (50 mg, 0.10 mmol), benzoyl chloride (0.036 mL, 0.30 mmol) and triethylamine (0.5 mL, 5.0 mmol), Compound 47 (41 mg, yield 58%) was obtained in the same manner as in Example 23.

$^1$HNMR (CDCl$_3$, 300 MHz) δ8.60 (dd, J=4.7, 1.7 Hz, 1H), 8.49 (br s, 1H), 8.04–8.10 (m, 6H), 7.11–7.57 (m, 11H), 7.05–7.17 (m, 2H), 5.29–5.40 (m, 2H), 5.02 (d, J=8.4 Hz, 1H), 4.43 (m, 1H), 4.00 (d, J=15.2 Hz, 1H), 3.08 (dd, J=17.5, 5.0 Hz, 1H), 2.79 (m, 1H)

EXAMPLE 46
Synthesis of Compound 48

From Compound 22 (50 mg, 0.10 mmol), isobutyryl chloride (0.031 mL, 0.3 mmol) and triethylamine (0.5 mL, 5.0 mmol), Compound 48 (40 mg, yield 63%) was obtained in the same manner as in Example 23.

$^1$HNMR (CDCl$_3$, 300 MHz) δ8.56 (dd, J=4.3, 1.2 Hz, 1H), 8.39 (d, J=1.2 Hz, 1H), 7.56 (dd, J=7.9, 1.2 Hz, 1H), 7.55 (dt, J=7.9, 1.8 Hz, 1H), 7.19–7.47 (m, 3H), 7.26 (d, J=8.4 Hz, 1H), 7.14 (td, J=7.9, 1.8 Hz, 1H), 7.05 (d, J=2.0 Hz, 1H), 6.97 (dd, J=8.3, 2.0 Hz, 1H), 5.34 (d, J=15.0 Hz, 1H), 5.24 (dd, J=9.8, 9.0 Hz, 1H), 4.91 (d, J=9.0 Hz, 1H), 4.41 (m, 1H), 3.80 (d, J=15.0 Hz, 1H), 3.05 (dd, J=17.6, 5.0 Hz, 1H), 2.73–2.87 (m, 3H), 1.32 (d, J=7.0 Hz, 6H), 1.31 (d, J=7.0 Hz, 6H)

EXAMPLE 47
Synthesis of Compound 49

From Compound 22 (50 mg, 0.10 mmol), cyclopentyl-carbonyl chloride (0.036 mL, 0.30 mmol) and triethylamine (0.5 mL, 5.0 mmol), Compound 49 (38 mg, yield 55%) was obtained in the same manner as in Example 23.

$^1$HNMR (CDCl$_3$, 300 MHz) δ8.57 (dd, J=4.7, 1.5 Hz, 1H), 8.39 (d, J=1.5 Hz, 1H), 7.56 (dd, J=8.0, 1.5 Hz, 1H), 7.45 (dt, J=8.0, 1.5 Hz, 1H), 7.14–7.33 (m, 5H), 7.05 (d, J=2.2 Hz, 1H), 6.96 (dd, J=8.3, 2.2 Hz, 1H), 5.35 (d, J=15.1 Hz, 1H), 5.24 (dd, J=9.8, 9.0 Hz, 1H), 4.91 (d, J=9.0 Hz, 1H), 4.37 (m, 1H), 3.67 (d, J=15.1 Hz, 1H), 2.92–3.09 (m, 3H), 2.79 (m, 1H), 1.60–2.05 (m, 16H)

EXAMPLE 48
Synthesis of Compound 50

Methyl 3-(2-bromophenyl)-4-nitrobutyrate (411 mg, 1.4 mmol), p-nitrobenzaldehyde (206 mg, 1.4 mmol) and 3-aminomethylpyridine (0.28 mL, 2.8 mmol) were stirred in ethanol at room temperature for 2 days. After evaporating ethanol under reduced pressure, the residue was purified by silica gel column chromatography (eluted with chloroform/methanol=99/1) to give Compound 50 (20 mg, yield 3.0%).

$^1$HNMR (CDCl$_3$, 300 MHz) δ8.58–8.56 (m, 1H), 8.33–8.16 (m, 4H), 7.58–7.53 (m, 1H), 7.50–7.48 (m, 1H), 7.38–7.34 (m, 2H), 7.31–7.29 (m, 1H), 7.22–7.13 (m, 2H), 5.31–5.26 (m, 2H), 5.05 (d, J=8.6 Hz, 1H), 4.41–4.36 (m, 1H), 3.78 (d, J=15.0 Hz, 1H), 3.13 (dd, J=17.0, 5.4 Hz, 1H), 2.–92–2.86 (m, 1H)

EXAMPLE 49
Synthesis of Compound 51

Compound 43 (23 mg, 0.045 mmol) was dissolved in ethanol (5.0 mL), and palladium-carbon (10%, 20 mg) was added thereto, followed by stirring under a hydrogen atmosphere at room temperature for 20 hours. After removing palladium-carbon by filtration, the filtrate was purified by preparative thin layer chromatography (developed with chloroform/methanol=95/5) to give Compound 51 (4.0 mg, yield 19%).

$^1$HNMR (CDCl$_3$, 300 MHz) δ8.56–8.55 (m, 1H), 8.30–8.29 (m, 1H), 7.58–7.55 (m, 2H), 7.33–7.11 (m, 5H), 6.70–6.68 (m, 1H), 6.54–6.52 (m, 1H), 6.41–6.40 (m, 1H), 5.28–5.23 (m, 2H), 4.78 (d, J=8.8 Hz, 1H), 4.35–4.30 (m, 1H), 3.86–3.74 (m, 3H), 3.04 (dd, J=18.0, 5.0 Hz, 1H), 2.97–2.78 (m, 1H)

EXAMPLE 50
Synthesis of Compound 52

Compound 50 (14 mg, 0.028 mmol) was dissolved in ethanol (3.0 mL), and palladium-carbon (10%, 5.0 mg) was added thereto, followed by stirring under a hydrogen atmosphere at room temperature for 5 hours. After removing palladium-carbon by filtration, the filtrate was purified by preparative thin layer chromatography (developed with chloroform/methanol=95/5) to give Compound 52 (3.5 mg, yield 26%).

$^1$HNMR (CDCl$_3$, 300 MHz) δ8.55–8.53 (m, 1H), 8.23–8.22 (m, 1H), 7.61–7.51 (m, 2H), 7.33–7.11 (m, 4H), 6.91 (d, J=8.4 Hz, 2H), 6.65 (d, J=8.4 Hz, 2H), 5.24–5.22 (m, 1H), 5.19 (d, J=15.0 Hz, 1H), 4.75 (d, J=9.4 Hz, 1H), 4.39–4.30 (m, 1H), 3.87–3.78 (m, 3H), 3.06 (dd, J=18.0, 6.1 Hz, 1H), 2.98–2.76 (m, 1H)

EXAMPLE 51
Synthesis of Compound 53

Methyl 3-(2-bromophenyl)-4-nitrobutyrate (508 mg, 1.7 mmol), 3,5-dihydroxybenzaldehyde (233 mg, 1.7 mmol) and 3-aminomethylpyridine (0.34 mL, 3.4 mmol) were heated under reflux in ethanol for 20 hours. After evaporating ethanol under reduced pressure, the residue was purified by silica gel column chromatography (eluted with chloroform/methanol=95/5) to give Compound 53 (44 mg, yield 5.0%).

$^1$HNMR (DMSO-d$_6$, 300 MHz) δ9.78 (s, 1H), 9.73 (s, 1H), 8.44 (dd, J=4.8, 2.0 Hz, 1H), 8.24 (d, J=2.0 Hz, 1H), 7.80 (d, J=7.5 Hz, 1H), 7.62–7.58 (m, 1H), 7.53–7.49 (m, 1H), 7.42 (t, J=7.5 Hz, 1H), 7.34–7.29 (m, 1H), 7.24–7.19 (m, 1H), 6.25–6.19 (m, 3H), 5.85–5.78 (m, 1H), 4.81–4.74 (m, 2H), 4.36–4.26 (m, 1H), 3.95 (d, J=15.0 Hz, 1H), 3.09–2.99 (m, 1H), 2.71 (dd, J=17.0, 5.0 Hz, 1H)

EXAMPLE 52
Synthesis of Compound 54

From methyl 3-(2-ethylphenyl)-4-nitrobutyrate (251 mg, 1.0 mol), 3,4-dihydroxybenzaldehyde (138 mg, 1.0 mmol) and 3-aminomethylpyridine (0.20 mL, 2.0 mmol), Compound 54 (57 mg, yield 13%) was obtained in the same manner as in Example 1.

$^1$HNMR (DMSO-d$_6$, 300 MHz) δ9.20 (br s, 1H), 8.92 (br s, 1H), 8.41 (d, J=4.8 Hz, 1H), 8.18 (br s, 1H), 7.66 (d, J=7.0 Hz, 1H), 7.46 (d, J=8.1 Hz, 1H), 7.28 (m, 1H), 7.15–7.19 (m, 3H), 6.73 (s, 1H), 6.62 (d, J=8.1 Hz, 1H), 6.53 (d, J=8.1 Hz, 1H), 5.75 (dd, J=10.8, 10.1 Hz, 1H), 4.78(d, J =10.1 Hz, 1H), 4.65 (d, J=15.4 Hz, 1H), 4.17 (m, 1H), 4.00 (d, J=15.4 Hz, 1H), 3.17 (dd, J=17.2, 12.6 Hz, 1H), 2.44–2.70 (m, 3H), 1.13 (d, J=7.4 Hz, 3H)

EXAMPLE 53
Synthesis of Compound 55

From methyl 3-(2,5-dichlorophenyl)-4-nitrobutyrate (291 mg, 1.0 mol), 4-hydroxybenzaldehyde (108 mg, 1.0 mmol) and 3-aminomethylpyridine (0.20 mL, 2.0 mmol), Compound 55 (103 mg, yield 22%) was obtained in the same manner as in Example 1.

$^1$HNMR (DMSO-d$_6$, 300 MHz) δ9.63 (br s, 1H), 8.41 (d, J =4.8, 1.7 Hz, 1H), 8.18 (d, J=1.8 Hz, 1H), 7.99 (d, J=1.8 Hz, 1H), 7.48 (d, J=8.6 Hz, 1H), 7.38–7.41 (m, 2H), 7.24 (dd, J=7.9, 4.9 Hz, 1H), 7.11 (d, J=8.4 Hz, 2H), 6.63 (d, J=8.4 Hz, 2H), 6.53 (d, J=8.1 Hz, 1H), 5.75 (dd, J=11.5, 9.9 Hz, 1H), 4.97 (d, J=9.9 Hz, 1H), 4.39–4.49 (m, 2H), 4.18 (d, J=15.6 Hz, 1H), 3.02 (dd, J=17.1, 12.8 Hz, 1H), 2.78 (dd, J=17.1, 5.3 Hz, 1H)

EXAMPLE 54
Synthesis of Compound 56

Methyl 3-(2-bromophenyl)-4-nitrobutyrate (409 mg, 1.4 mmol), p-dimethylaminobenzaldehyde (202 mg, 1.4 mmol) and 3-aminomethylpyridine (0.48 mL, 2.8 mmol) were heated under reflux in ethanol for 2 days. After evaporating ethanol under reduced pressure, the residue was purified by silica gel column chromatography (eluted with chloroform/methanol=97/3) to give Compound 56 (116 mg, yield 23%).

$^1$HNMR (CDCl$_3$, 300 MHz) δ8.53 (dd, J=5.0, 2.0 Hz, 1H), 8.24 (d, J=2.0 Hz, 1H), 7.57–7.51 (m, 2H), 7.28–7.24 (m, 3H), 7.16–7.11 (m, 1H), 6.98 (d, J=8.8 Hz, 2H), 6.66 (d, J=8.8 Hz, 2H), 5.32–5.21 (m, 1H), 5.23 (d, J=15.0 Hz, 1H), 4.76 (d, J=9.4 Hz, 1H), 4.38–4.30 (m, 1H), 3.81 (d, J=15.0

Hz, 1H), 3.06 (dd, J=18.0, 5.0 Hz, 1H), 2.98 (s, 6H), 2.75–2.61 (m, 1H)

EXAMPLE 55
Synthesis of Compound 57

Methyl 3-(2-bromophenyl)-4-nitrobutyrate (439 mg, 1.5 mmol), 3-hydroxybenzaldehyde (160 mg, 1.5 mmol) and 3-aminomethylpyridine (0.49 mL, 2.9 mmol) were heated under reflux in ethanol for 20 hours. After evaporating ethanol under reduced pressure, the residue was purified by silica gel column chromatography (eluted with chloroform/methanol=98/2) to give Compound 57 (101 mg, yield 15%).

$^1$HNMR (DMSO-$d_6$, 300 MHz) δ9.56 (s, 1H), 8.41 (dd, J=4.6, 2.0 Hz, 1H), 8.16 (d, J=2.0 Hz, 1H), 7.81–7.78 (m, 1H), 7.62–7.59 (m, 1H), 7.45–7.40 (m, 2H), 7.29–7.19 (m, 2H), 7.12–7.07 (m, 1H), 6.76–6.72 (m, 3H), 5.91–5.84 (m, 1H), 4.93 (d, J=9.7 Hz, 1H), 4.61 (d, J=15.0 Hz, 1H), 4.42–4.32 (m, 1H), 4.07 (d, J=15.0 Hz, 1H), 3.16–3.04 (m, 1H), 2.74 (dd, J=17.0, 5.0 Hz, 1H)

EXAMPLE 56
Synthesis of Compound 58

3,4,5-Trihydroxybenzaldehyde (628 mg, 3.6 mmol) was dissolved in dimethylformamide (30 mL), and potassium carbonate (2.0 g, 14 mmol) was added thereto, followed by stirring at room temperature for 30 minutes. Next, chloromethyl methyl ether (0.96 mL, 13 mmol) was added thereto, followed by stirring at room temperature for 2 hours. After the conventional post-treatment, the residue was purified by preparative thin layer chromatography (developed with chloroform/methanol=98/2) to give 3-hydroxy-4,5-bis(methoxymethoxy)benzaldehyde (140 mg, yield 17%).

$^1$HNMR (CDCl$_3$, 300 MHz) δ9.83 (s, 1H), 7.24 (d, J=1.8 Hz, 1H), 7.19 (d, J=1.8 Hz, 1H), 6.90 (s, 1H), 5.26 (s, 2H), 5.23 (s, 2H), 3.64 (s, 3H), 3.51 (s, 3H)

Subsequently, 3-hydroxy-4,5-bis(methoxymethoxy) benzaldehyde (140 mg, 0.61 mmol) obtained above, methyl 3-(2-bromophenyl)-4-nitrobutyrate (204 mg, 0.68 mmol) and 3-aminomethylpyridine (0.16 mL, 1.4 mmol) were heated under reflux in ethanol for 20 hours. After evaporating ethanol under reduced pressure, the residue was purified by silica gel column chromatography (eluted with chloroform/methanol=95/5) to give Compound 58 (33 mg, yield 8.0%).

$^1$HNMR (CDCl$_3$, 300 MHz) δ10.10 (s, 1H), 8.47 (dd, J=5.0, 1.7 Hz, 1H), 8.29 (d, J=1.7 Hz, 1H), 7.57 (d, J=7.8 Hz, 2H), 7.41–7.31 (m, 4H), 7.19–7.13 (m, 1H), 6.48–6.45 (m, 2H), 5.43–5.36 (m, 1H), 5.15 (s, 2H), 5.12 (s, 2H), 5.05 (d, J=15.0 Hz, 1H), 4.81 (d, J=8.8 Hz, 1H), 4.42–4.32 (m, 1H), 3.62 (s, 3H), 3.51 (s, 3H), 3.00 (dd, J=18.0, 5.3 Hz, 1H), 2.92–2.87 (m, 1H)

EXAMPLE 57
Synthesis of Compound 59

Compound 43 (200 mg, 0.39 mmol) was dissolved in ethanol (5.0 mL), and palladium-carbon (10%, 10 mg) was added thereto, followed by stirring under a hydrogen atmosphere at room temperature for 9 hours. After removing palladium-carbon by filtration, the filtrate was purified by preparative thin layer chromatography (developed with chloroform/methanol=90/10) to give Compound 59 (115 mg, yield 60%).

$^1$HNMR (CDCl$_3$, 300 MHz) δ8.49 (dd, J=4.8, 1.6 Hz, 1H), 8.19 (d, J=1.6 Hz, 1H), 7.76–7.53 (m, 2H), 7.49–7.21 (m, 2H), 7.15–7.09 (m, 2H), 6.96–6.82 (m, 3H), 6.70 (d, J=7.4 Hz, 1H), 5.23 (t, J=10.0 Hz, 1H), 5.09 (d, J=15.0 Hz, 1H), 4.85 (d, J=10.0 Hz, 1H), 4.42–4.32 (m, 1H), 3.95 (d, J =15.0 Hz, 1H), 3.03 (dd, J=18.0, 5.0 Hz, 1H), 2.83–2.72 (m, 1H)

EXAMPLE 58
Synthesis of Compound 60

Compound 51 (10 mg, 0.021 mmol) was dissolved in dichloromethane (2.0 mL). Acetyl chloride (1.7 μL, 0.025 mmol) and triethylamine (3.0 μL, 0.021 mmol) were added thereto, followed by stirring at room temperature for 2 hours. After the conventional post-treatment, the residue was purified by preparative thin layer chromatography (developed with chloroform/methanol=90/10) to give Compound 60 (11 mg, yield 98%).

$^1$HNMR (CDCl$_3$, 300 MHz) δ8.52 (dd, J=4.8, 2.0 Hz, 1H), 8.20 (d, J=2.0 Hz, 1H), 7.61–7.45 (m, 5H), 7.36–7.22 (m, 4H), 7.20–7.11 (m, 1H), 6.88 (d, J=7.8 Hz, 1H), 5.30 (t, J=10.0 Hz, 1H), 5.17 (d, J=15.0 Hz, 1H), 4.87 (d, J=10.0 Hz, 1H), 4.41–4.32 (m, 1H), 3.89 (d, J=15.0 Hz, 1H), 3.05 (dd, J=18.0, 5.0 Hz, 1H), 2.84–2.80 (m, 1H), 2.18 (s, 3H)

EXAMPLE 59
Synthesis of Compound 61

Compound 51 (10 mg, 0.021 mmol) was dissolved in dichloromethane (2.0 mL). Methanesulfonyl chloride (20 μL, 0.25 mmol) and triethylamine (30 μL, 0.21 mmol) were added thereto, followed by stirring at room temperature for 5 hours. After the conventional post-treatment, the residue was purified by preparative thin layer chromatography (developed with chloroform/methanol=90/10) to give Compound 61 (9.2 mg, yield 76%).

$^1$HNMR (CDCl$_3$, 300 MHz) δ8.50 (dd, J=5.0, 2.0 Hz, 1H), 8.19 (d, J=2.0 Hz, 1H), 7.61–7.55 (m, 2H), 7.40–7.22 (m, 6H), 7.17–7.07 (m, 2H), 6.99 (d, J=7.5 Hz, 1H), 5.34–5.30 (m, 1H), 5.05 (d, J=15.0 Hz, 1H), 4.91 (d, J=9.0 Hz, 1H), 4.57–4.40 (m, 1H), 4.05 (d, J=15.0 Hz, 1H), 3.07 (dd, J=18.0, 5.1 Hz, 1H), 3.00 (s, 3H), 2.87–2.83 (m, 1H)

EXAMPLE 60
Synthesis of Compound 62

Compound 58 (21 mg, 0.34 mmol) was dissolved in methanol, and a 10% hydrochloric acid-methanol solution (0.4 mL) was added thereto under ice-cooling, followed by stirring for 2 hours to eliminate the protecting group. After the completion of the reaction, methanol was evaporated under reduced pressure to give Compound 62 (18 mg, hydrochloride, yield 94%).

$^1$HNMR (CD$_3$OD, 300 MHz) δ8.64–8.62 (m, 1H), 8.39 (m, 1H), 8.20 (d, J=7.8 Hz, 1H), 7.90–7.86 (m, 1H), 7.67–7.58 (m, 2H), 7.41–7.37 (m, 1H), 7.22–7.19 (m, 1H), 6.30 (s, 2H), 5.71 (t, J=10.0 Hz, 1H), 5.14 (d, J=16.0 Hz, 1H), 5.00 (d, J=10.0 Hz, 1H), 4.64–4.52 (m, 1H), 4.24 (d, J=16.0 Hz, 1H), 3.12–3.03 (m, 1H), 2.90 (dd, J=18.0, 5.0 Hz, 1H)

EXAMPLE 61
Synthesis of Compounds 63 and 64

Compound 48 (4.0 g, 6.2 mmol) was optically resolved by high performance liquid chromatography (HPLC) with the use of Chiralcel OD (2 cm in diameter, 25 cm in length; eluent: ispropylamine: n-hexane: diethylamine=4:6:0.01) to give the (+)-optical isomer (1.0 g, yield 19%) of Compound 48 and the (−)-optical isomer (1.3 g, yield 25%) thereof.
Compound63 ((+)-optical Isomer of Compound 22)

An aqueous solution (1.0 mL) of sodium bicarbonate (66 mg, 0.78 mmol) was added to a solution (10 mL) of the (+)-optical isomer (47 mg, 0.074 mmol) of Compound 48 in methanol, followed by stirring at room temperature for 6 hours. Next, the reaction solution was neutralized with a saturated aqueous solution of ammonium chloride and extracted with chloroform. The obtained organic layer was dried over sodium sulfate. After evaporating the solvent under reduced pressure, the residue was purified by column chromatography (eluted with chloroform/methanol=5/95) to give Compound 63 (23 mg, yield 63%).

$[\alpha]^{28}_D$=+83° (c=0.66, methanol).

Compound 64 ((−)-optical Isomer of Compound 22)

An aqueous solution (1.0 mL) of sodium bicarbonate (66 mg, 0.78 mmol) was added to a solution (10 mL) of the (−)-optical isomer (47 mg, 0.074 mmol) of Compound 48 in methanol, followed by stirring at room temperature for 6 hours. Next, the reaction solution was neutralized with a saturated aqueous solution of ammonium chloride and extracted with chloroform. The obtained organic layer was dried over sodium sulfate. After evaporating the solvent under reduced pressure, the residue was purified by column chromatography (eluted with chloroform/methanol=5/95) to give Compound 64 (18 mg, yield 48%).

$[\alpha]^{28}_D$=−90° (c=0.30, methanol).

EXAMPLE 62

Synthesis of Compound 65

Methyl 3-(2-bromophenyl)-4-nitrobutyrate (436 mg, 1.4 mmol), 4-hydroxy-3-(hydroxymethyl)benzaldehyde (198 mg, 1.3 mmol) and 3-aminomethylpyridine (0.29 mL, 2.8 mmol) were heated under reflux in ethanol for 20 hours. After evaporating ethanol under reduced pressure, the residue was purified by silica gel column chromatography (eluted with chloroform/methanol=98/2) to give Compound 65 (24 mg, yield 3.2%).

$^1$HNMR (DMSO-$d_6$, 300 MHz) δ9.61 (s, 1H), 8.40 (dd, J=5.0, 1.8 Hz, 1H), 8.13 (d, J=1.8 Hz, 1H), 7.82–7.79 (m, 1H), 7.62–7.59 (m, 1H), 7.45–7.39 (m, 2H), 7.30–7.19 (m, 3H), 6.99–6.96 (m, 1H), 6.63 (d, J=8.3 Hz, 1H), 5.90–5.83 (m, 1H), 5.01 (br s, 1H), 4.90 (d, J=9.7 Hz, 1H), 4.58 (d, J=15.0 Hz, 1H), 4.43–4.32 (m, 3H), 4.05 (d, J=15.0 Hz, 1H), 3.26–3.20 (m, 1H), 2.74 (dd, J=17.0, 5.3 Hz, 1H)

EXAMPLE 63

Synthesis of Compound 66

From methyl 3-[2-((E)-1-propenyl)phenyl]-4-nitrobutyrate (52 mg, 0.20 mol), 3,4-dihydroxybenzaldehyde (28 mg, 0.20 mmol) and 3-aminomethylpyridine (0.041 mL, 0.40 mmol), Compound 66 (6.2 mg, yield 6.8%) was obtained in the same manner as in Example 1.

$^1$HNMR (DMSO-$d_6$, 300 MHz) δ9.20 (br s, 1H), 8.90 (br s, 1H), 8.41 (d, J=4.2 Hz, 1H), 8.19 (br s, 1H), 7.65 (d, J=7.5 Hz, 1H), 7.47 (d, J=8.9 Hz, 1H), 7.40 (d, J=8.9 Hz, 1H), 7.19–7.30 (m, 3H), 6.86 (d, J=15.0 Hz, 1H), 6.73 (s, 1H), 6.62 (d, J=8.3 Hz, 1H), 6.58 (d, J=8.3 Hz, 1H), 6.10 (dq, J=15.0, 6.2 Hz, 1H), 5.73 (dd, J=11.0, 10.0 Hz, 1H), 4.78 (d, J=10.0 Hz, 1H), 4.67 (d, J=15.6 Hz, 1H), 4.32 (ddd, J=12.9, 11.0, 4.4 Hz, 1H), 3.99 (d, J=15.6 Hz, 1H), 3.01 (dd, J=17.2, 12.9 Hz, 1H), 2.65 (dd, J=17.2, 4.4 Hz, 1H), 1.90 (d, J=6.2 Hz, 3H)

EXAMPLE 64

Synthesis of Compound 67

Compound 52 (2.0 mg, 0.0042 mmol) was dissolved in dichloromethane (2.0 mL). Acetyl chloride (0.6 μL, 0.0084 mmol) and triethylamine (2.3 μL, 0.017 mmol) were added thereto, followed by stirring at room temperature for 2 hours. After the conventional post-treatment, the residue was purified by preparative thin layer chromatography (developed with chloroform/methanol=95/5) to quantitatively give Compound 67 (2.2 mg).

$^1$HNMR (CDCl$_3$, 300 MHz) δ8.54 (dd, J=4.6, 2.0 Hz, 1H), 8.18 (d, J=2.0 Hz, 1H), 7.61–7.51 (m, 6H), 7.26–7.20 (m, 3H), 7.17–7.09 (m, 2H), 5.39–5.19 (m, 2H), 4.85 (d, J=9.0 Hz, 1H), 4.44–4.28 (m, 1H), 3.83 (d, J=14.0 Hz, 1H), 3.04 (dd, J=18.0, 5.0 Hz, 1H), 2.99–2.88 (m, 1H), 2.20 (s, 3H)

EXAMPLE 65

Synthesis of Compound 68 (Hydrochloride of Compound 22)

A solution (4 mol/L, 2.5 mL) of hydrochloric acid in dioxane was added to a solution (600 mL) of Compound 22 (4.0 mg, 8.1 mmol) in ethanol, followed by stirring at room temperature for 30 minutes. After evaporating the solvent of the reaction solution under reduced pressure, the residue was powdered with ethanol/diethyl ether (30 mL/300 mL) to give Compound 68 (3.65 g, yield 85%).

$^1$HNMR (DMSO-$d_6$, 300 MHz) δ8.71 (d, J 5.3 Hz, 1H), 8.46 (br s, 1H), 8.07 (d, J=8.1 Hz, 1H), 7.78–7.82 (m, 2H), 7.61 (d, J=7.8 Hz, 1H), 7.45 (d, J=7.8 Hz, 1H), 7.21 (d, J=7.8 Hz, 1H), 6.76 (br s, 1H), 6.59–6.61 (m, 2H), 5.89 (dd, J=11.3, 10.1 Hz, 1H), 5.00 (d, J=10.1 Hz, 1H), 4.39–4.45 (m, 3H), 3.03 (dd, J=17.3, 12.5 Hz, 1H), 2.73 (dd, J=17.3, 4.8 Hz, 1H)

EXAMPLE 66

Synthesis of Compound 69 (Hydrochloride of Compound 64)

A solution (4 mol/L, 0.4 mL) of hydrochloric acid in dioxane was added to a solution (100 mL) of Compound 64 (500 mg, 1.0 mmol) in ethanol, followed by stirring at room temperature for 1 hour. After evaporating the solvent of the reaction solution under reduced pressure, the residue was powdered with ethanol/diethyl ether (20 mL/250 mL) to give Compound 69 (220 mg, yield 41%).

$[\alpha]^{28}_D$=−101° (c=0.12, methanol).

EXAMPLE 67

Synthesis of Compound 70 (Hydrochloride of Compound 63)

A solution (4 mol/L, 0.4 mL) of hydrochloric acid in dioxane was added to a solution (100 mL) of Compound 63 (500 mg, 1.0 mmol) in ethanol, followed by stirring at room temperature for 1 hour. After evaporating the solvent of the reaction solution under reduced pressure, the residue was powdered with ethanol/diethyl ether (20 mL/250 mL) to give Compound 70 (320 mg, yield 60%).

$[\alpha]^{28}_D$=+100° (c=0.18, methanol).

EXAMPLE 68

Synthesis of Compound 71

From methyl 3-(2-n-propylphenyl)-4-nitrobutyrate (83 mg, 0.30 mol), 3,4-dihydroxybenzaldehyde (41.4 mg, 0.30 mmol) and 3-aminomethylpyridine (0.061 mL, 0.60 mmol), Compound 71 (25 mg, yield 18%) was obtained in the same manner as in Example 1.

$^1$HNMR (DMSO-$d_6$, 300 MHz) δ9.20 (br s, 1H), 8.91 (br s, 1H), 8.42 (dd, J=4.8, 1.6 Hz, 1H), 8.18 (br s, 1H), 7.67 (d, J=7.7 Hz, 1H), 7.46 (d, J=7.7 Hz, 1H), 7.14–7.29 (m, 4H), 6.74 (d, J=1.6 Hz, 1H), 6.62 (d, J=9.1 Hz, 1H), 6.55 (d, J=9.1 Hz, 1H), 5.74 (dd, J=11.4, 9.9 Hz, 1H), 4.80 (d, J =9.9 Hz, 1H), 4.62 (d, J=15.6 Hz, 1H), 4.03–4.18 (m, 2H), 3.05 (dd, J=17.0, 13.0 Hz, 1H), 2.51–2.74 (m, 3H), 1.52 (qt, J=7.5, 7.1 Hz, 2H), 0.95 (t, J=7.5 Hz, 3H)

EXAMPLE 69

Synthesis of Compound 72

Under an argon atmosphere, triethylamine (1.0 mL), 4,4-diethoxy-1-butene (0.1 mL, 0.82 mmol) and Compound 22 (98 mg, 0.20 mmol) were added to a solution (2 mL) of palladium (II) diacetate (11.3 mg, 0.05 mmol) and tris(2- methylphenyl)phosphine (60.8 mg, 0.20 mmol) in DMF, followed by stirring at 80° C. for 5 hours. Next, the reaction solution was filtered through celite and purified by silica gel column chromatography (eluted with chloroform/methanol= 19/1) to give Compound 72 (56 mg, yield 50%).

$^1$HNMR (DMSO-$d_6$, 300 MHz) δ9.22 (br s, 1H), 8.94 (br s, 1H), 8.42 (d, J=3.3 Hz, 1H), 8.19 (br s, 1H), 7.66 (d, J=7.5 Hz, 1H), 7.47 (d, J=7.9 Hz, 1H), 7.21–7.38 (m, 4H), 6.93 (d, J=15.5 Hz, 1H), 6.73 (s, 1H), 6.63 (d, J=8.3 Hz, 1H), 6.55 (d, J=8.3 Hz, 1H), 5.99 (dt, J=15.5, 7.3 Hz, 1H), 5.75 (dd, J=11.0, 10.2 Hz, 1H), 4.70–4.76 (m, 2H), 4.60 (t, J=5.5 Hz, 1H), 4.24–4.33 (m, 1H), 3.95 (d, J=15.4 Hz, 1H), 3.46–3.65 (m, 6H), 2.98 (dd, J=16.8, 13.2 Hz, 2H), 2.65 (dd, J=16.8, 5.5 Hz, 2H), 1.12 (t, J=7.3 Hz, 3H)

EXAMPLE 70
Synthesis of Compound 73
From Compound 22 (99 mg, 0.20 mmol) and phenylboric acid (60.8 mg, 0.20 mmol), Compound 73 (9.8 mg, yield 9.9%) was obtained in the same manner as in Example 69.

$^1$HNMR (DMSO-$d_6$, 300 MHz) δ9.23 (br s, 1H), 9.20 (br s, 1H), 8.37 (dd, J=4.4, 1.9 Hz, 1H), 8.06 (br s, 1H), 7.85 (d, J=7.7 Hz, 1H), 7.15–7.52 (m, 10H), 6.70 (d, J=1.6 Hz, 1H), 6.59 (d, J=8.1 Hz, 1H), 6.50 (d, J=8.1 Hz, 1H), 5.75 (dd, J=10.6, 10.2 Hz, 1H), 4.53 (d, J=15.4 Hz, 1H), 4.46 (d, J =9.7 Hz, 1H), 3.93 (d, J=15.4 Hz, 1H), 3.74–3.82 (m, 1H), 3.16 (dd, J=17.2, 16.2 Hz, 1H), 2.80 (dd, J=17.2, 4.8 Hz, 1H)

EXAMPLE 71
Synthesis of Compound 74
From methyl 3-(2-methylphenyl)-4-nitrobutyrate (240 mg, 1.0 mmol), 2-bromobenzaldehyde (183 mg, 1.0 mmol) and 3-aminomethylpyridine (0.21 mL, 2.0 mmol), Compound 74 (278 mg, yield 58%) was obtained in the same manner as in Example 1.

$^1$HNMR (DMSO-$d_6$, 300 MHz) δ9.20 (br s, 1H), 8.91 (br s, 1H), 8.42 (dd, J=4.8, 1.6 Hz, 1H), 8.18 (br s, 1H), 7.67 (d, J=7.7 Hz, 1H), 7.46 (d, J=7.7 Hz, 1H), 7.14–7.29 (m, 4H), 6.74 (d, J=1.6 Hz, 1H), 6.62 (d, J=9.1 Hz, 1H), 6.55 (d, J=9.1 Hz, 1H), 5.74 (dd, J=11.4, 9.9 Hz, 1H), 4.80 (d, J =9.9 Hz, 1H), 4.62 (d, J=15.6 Hz, 1H), 4.03–4.18 (m, 2H), 3.05 (dd, J=17.0, 13.0 Hz, 1H), 2.51–2.74 (m, 3H), 1.52 (qt, J=7.5, 7.1 Hz, 2H), 0.95 (t, J=7.5 Hz, 3H)

EXAMPLE 72
Synthesis of Compound 75
From methyl 3-(1-naphthyl)-4-nitrobutyrate (409 mg, 1.5 mmol), 4-hydroxybenzaldehyde (122 mg, 1.0 mmol) and 3-aminomethylpyridine (0.204 mL, 2.0 mmol), Compound 75 (190 mg, yield 42%) was obtained in the same manner as in Example 1.

$^1$HNMR (DMSO-$d_6$, 300 MHz) δ9.60 (br s, 1H), 8.46–8.38 (m, 2H), 8.19 (br s, 1H), 7.93–7.70 (m, 3H), 7.62–7.48 (m, 4H), 7.28 (m, 1H), 7.12 (m, 2H), 6.68 (m, 2H), 5.97 (dd, J=11.0, 10.0 Hz, 1H), 5.02 (m, 1H), 4.95 (d, J=10.0 Hz, 1H), 4.75 (d, J=15.5 Hz, 1H), 4.04 (d, J=15.5 Hz, 1H), 3.22–2.80 (m, 2H)

EXAMPLE 73
Synthesis of Compound 76
From methyl 3-(3,4-ethylenedioxyphenyl)-4-nitrobutyrate (250 mg, 0.89 mmol), 4-hydroxybenzaldehyde (72 mg, 0.59 mmol) and 3-aminomethylpyridine (0.12 mL, 1.2 mmol), Compound 76 (45 mg, yield 11%) was obtained in the same manner as in Example 1.

$^1$HNMR (DMSO-$d_6$, 300 MHz) δ9.63 (br s, 1H), 8.41 (m, 1H), 8.14 (br s, 1H), 7.50–6.60 (m, 9H), 5.59 (dd, J=11.8, 9.7 Hz, 1H), 4.74 (d, J=11.8 Hz, 1H), 4.69 (d, J=15.5 Hz, 1H), 4.20 (br s, 4H), 3.90 (d, J=15.5 Hz, 1H), 3.75 (m, 1H), 3.09 (dd, J=17.0, 13.6 Hz, 1H), 2.65 (dd, J=17.0, 4.5 Hz, 1H)

EXAMPLE 74
Synthesis of Compound 77
From methyl 3-(3-bromophenyl)-4-nitrobutyrate (302 mg, 1.0 mmol), 4-hydroxybenzaldehyde (122 mg, 1.0 mmol) and 4-aminomethylpyridine (0.20 mL, 2.0 mmol), Compound 77 (120 mg, yield 25%) was obtained in the same manner as in Example 1.

$^1$HNMR (DMSO-$d_6$, 300 MHz) δ9.67 (br s, 1H), 8.44 (m, 2H), 7.75 (br s, 1H), 7.50–6.60 (m, 9H), 5.76 (dd, J=11.5, 9.9 Hz, 1H), 4.82 (d, J=9.9 Hz, 1H), 4.67 (d, J=16.2 Hz, 1H), 4.00 (m, 1H), 3.90 (d, J=16.2 Hz, 1H), 3.17 (dd, J=16.9, 13.0 Hz, 1H), 2.77 (dd, J=16.9, 4.9 Hz, 1H)

EXAMPLE 75
Synthesis of Compound 78
Compound 1 (12 mg, 0.025 mmol) was dissolved in dichloromethane (1.0 mL), and m-chloroperbenzoic acid (24 mg, 0.10 mmol) was added thereto, followed by stirring at room temperature for 1 hour. After the reaction mixture was concentrated, the residue was purified by thin layer chromatography (developed with chloroform/methanol=95/5) to give Compound 78 (7.4 mg, yield 59%).

$^1$HNMR (DMSO-$d_6$, 300 MHz) δ9.66 (br s, 1H), 8.03 (br d, J=6.2 Hz, 1H), 7.86 (br s, 1H), 7.72 (br s, 1H), 7.53–6.56 (m, 9H), 5.77 (dd, J=10.5, 9.7 Hz, 1H), 4.90 (d, J=9.7 Hz, 1H), 4.37 (d, J=15.8 Hz, 1H), 4.12 (d, J=15.8 Hz, 1H), 3.96 (m, 1H), 3.15 (dd, J=16.5, 13.0 Hz, 1H), 2.75 (dd, J=16.5, 4.5 Hz, 1H)

EXAMPLE 76
Synthesis of Compound 79
From methyl 3-(2-pyridyl)-4-nitrobutyrate (230 mg, 1.0 mmol), 4-hydroxybenzaldehyde (120 mg, 1.0 mmol) and 3-aminomethylpyridine (0.20 mL, 2.0 mmol), Compound 79 (87 mg, yield 22%) was obtained in the same manner as in Example 1.

$^1$HNMR (DMSO-$d_6$, 300 MHz) δ9.62 (s, 1H), 8.51 (d, J=4.8 Hz, 1H), 8.44 (dd, J=4.8, 1.8 Hz, 1H), 8.19 (d, J=1.8 Hz, 1H), 7.78 (dt, J=7.9, 1.8 Hz, 1H), 7.48 (d, J=4.9 Hz, 1H), 7.40 (d, J=7.9 Hz, 1H), 7.27–7.31 (m, 2H), 7.11 (d, J =8.6 Hz, 2H), 6.68 (d, J=8.6 Hz, 2H), 5.61 (dd, J=11.2, 9.5 Hz, 1H), 4.81 (d, J=9.5 Hz, 1H), 4.77 (d, J=15.8 Hz, 1H), 4.14 (m, 1H), 3.88 (d, J=15.8 Hz, 1H), 3.14 (dd, J=16.5, 12.5 Hz, 1H), 2.78 (dd, J=16.5, 4.5 Hz, 1H)

EXAMPLE 77
Synthesis of Compound 80
From methyl 3-(3-bromophenyl)nitrobutyrate (300 mg, 1.0 mmol), 3-pyridinecarbaldehyde (0.10 mL, 1.0 mmol) and 3-aminomethylpyridine (0.20 mL, 2.0 mmol), Compound 80 (79 mg, yield 17%) was obtained in the same manner as in Example 1.

$^1$HNMR (DMSO-$d_6$, 300 MHz) δ8.48–8.50 (m, 2H), 8.39 (d, J=4.8 Hz, 1H), 8.11 (s, 1H), 7.80 (d, J=8.1 Hz, 1H), 7.73 (s, 1H), 7.50 (d, J=7.7 Hz, 1H), 7.21–7.51 (m, 5H), 5.87 (dd, J=11.6, 9.9 Hz, 1H), 5.09 (d, J=9.9 Hz, 1H), 4.48 (d, J=15.8 Hz, 1H), 4.27 (d, J=15.8 Hz, 1H), 4.03 (dt, J=12.2, 4.8 Hz, 1H), 3.18 (dd, J=17.2, 12.2 Hz, 1H), 2.80 (dd, J=17.2, 4.8 Hz, 1H)

EXAMPLE 78
Synthesis of Compound 81
From methyl 3-(3-chlorophenyl)-4-nitrobutyrate (260 mg, 1.0 mmol), 3-pyridinecarbaldehyde (0.10 mL, 1.0 mmol) and 3-aminomethylpyridine (0.20 mL, 2.0 mmol), Compound 81 (49 mg, yield 12%) was obtained in the same manner as in Example 1.

$^1$HNMR (DMSO-d$_6$, 300 MHz) δ8.48–8.51 (m, 2H), 8.39 (dd, J=4.9, 1.3 Hz, 1H), 8.11 (d, J=1.9 Hz, 1H), 7.79 (td, J=8.1, 1.9 Hz, 1H), 7.38 (s, 1H), 7.22–7.38 (m, 6H), 5.88 (dd, J=11.2, 9.9 Hz, 1H), 5.09 (d, J=9.9 Hz, 1H), 4.48 (d, J=16.0 Hz, 1H), 4.27 (d, J=16.0 Hz, 1H), 4.04 (dt, J=12.3, 4.9 Hz, 1H), 3.22 (dd, J=17.0, 12.3 Hz, 1H), 2.80 (dd, J=17.0, 4.9 Hz, 1H)

EXAMPLE 79
Synthesis of Compound 82

From methyl 3-(3-thienyl)-4-nitrobutyrate (590 mg, 2.6 mmol), 3,4-dihydroxybenzaldehyde (360 mg, 2.6 mmol) and 3-aminomethylpyridine (5.1 mL, 5.2 mmol), Compound 82 (167 mg, yield 15%) was obtained in the same manner as in Example 1.

$^1$HNMR (DMSO-d$_6$, 300 MHz) δ9.23 (br s, 1H), 9.00 (br s, 1H), 8.45 (dd, J=3.1, 1.5 Hz, 1H), 8.20 (d, J=1.5 Hz, 1H), 7.47–7.50 (m, 2H), 7.40 (m, 1H), 7.32 (dd, J=7.8, 5.0 Hz, 1H), 7.20 (d, J=7.8 Hz, 1H), 6.49 (s, 1H), 6.48 (d, J=7.4 Hz, 1H), 6.47 (dd, J=7.4, 2.0 Hz, 1H), 5.52 (dd, J=11.5, 9.9 Hz, 1H), 4.88 (d, J=15.4 Hz, 1H), 4.65 (d, J=9.9 Hz, 1H), 4.00 (m, 1H), 3.77 (d, J=15.4 Hz, 1H), 3.19 (dd, J=17.1, 12.1 Hz, 1H), 2.91 (dd, J=17.1, 4.5 Hz, 1H)

EXAMPLE 80
Synthesis of Compound 83

From methyl 3-(2-furyl)-4-nitrobutyrate (450 mg, 2.1 mmol), 3,4-dihydroxybenzaldehyde (270 mg, 2.0 mmol) and 3-aminomethylpyridine (0.42 mL, 4.2 mmol), Compound 83 (272 mg, yield 32%) was obtained in the same manner as in Example 1.

$^1$HNMR (DMSO-d$_6$, 300 MHz) δ9.21 (s, 1H), 8.98 (s, 1H), 8.43 (dd, J=4.8, 3.2 Hz, 1H), 8.19 (d, J=2.0 Hz, 1H), 7.59 (dd, J=1.9, 0.6 Hz, 1H), 7.49 (dt, J=8.0, 1.9 Hz, 1H), 7.31 (dd, J=4.8, 0.6 Hz, 1H), 6.63–6.66 (m, 2H), 6.48 (dd, J=8.8, 2.1 Hz, 1H), 6.39 (m, 1H), 6.31 (d, J=3.2 Hz, 1H), 5.41 (dd, J=11.4, 9.7 Hz, 1H), 4.83 (d, J=15.6 Hz, 1H), 4.69 (d, J=9.7 Hz, 1H), 4.12 (m, 1H), 3.79 (d, J=15.6 Hz, 1H), 3.19 (dd, J=17.0, 12.6 Hz, 1H), 2.78 (dd, J=17.0, 4.6 Hz, 1H)

EXAMPLE 81
Synthesis of Compound 85

Methyl 3-(2-bromophenyl)-4-nitrobutyrate (205 mg, 0.68 mmol), 3,4-dihydroxybenzaldehyde (90 mg, 0.68 mmol) and 2-(2-aminoethyl)pyridine (0.16 mL, 1.4 mmol) were heated under reflux in ethanol for 20 hours. After evaporating ethanol under reduced pressure, the residue was purified by silica gel column chromatography (eluted with chloroform/methanol=95/5) to give Compound 85 (32 mg, yield 9.1%).

$^1$HNMR (DMSO-d$_6$, 300 MHz) δ9.20 (br s, 1H), 9.05 (br s, 1H), 8.55–8.53 (m, 1H), 7.44–7.69 (m, 2H), 7.60 (dd, J=8.1, 1.0 Hz, 1H), 7.39 (t, J=7.5 Hz, 1H), 7.26–7.16 (m, 3H), 6.78–6.77 (m, 1H), 6.74 (d, J=8.1 Hz, 1H), 6.62–6.59 (m, 1H), 5.72–5.65 (m, 1H), 4.66 (d, J=9.7 Hz, 1H), 4.26–4.16 (m, 1H), 4.02–3.92 (m, 1H), 3.06–2.96 (m, 1H), 2.82–2.72 (m, 2H), 2.53–2.50 (m, 2H)

EXAMPLE 82
Synthesis of Compound 86

Methyl 3-(2-bromophenyl)-4-nitrobutyrate (213 mg, 0.71 mmol), 3,4-dihydroxybenzaldehyde (98 mg, 0.71 mmol) and 3-(2-aminoethyl)pyridine (0.17 mL, 1.4 mmol) were heated under reflux in ethanol for 24 hours. After evaporating ethanol under reduced pressure, the residue was purified by silica gel column chromatography (eluted with chloroform/methanol=95/5) to give Compound 86 (2.0 mg, yield 0.55%).

$^1$HNMR (DMSO-d$_6$, 300 MHz) δ9.39 (br s, 1H), 9.04 (br s, 1H), 8.42–8.41 (m, 1H), 8.30–8.25 (m, 1H), 7.75 (d, J=7.9 Hz, 1H), 7.60 (d, J=7.9 Hz, 1H), 7.46–7.37 (m, 2H), 7.33–7.28 (m, 1H), 7.20 (t, J=7.9 Hz, 1H), 6.87–6.71 (m, 3H), 5.76 (t, J=10.0 Hz, 1H), 4.72 (d, J=10.0 Hz, 1H), 4.26–4.13 (m, 1H), 3.72–3.63 (m, 1H), 2.92–2.70 (m, 3H), 2.62–2.52 (m, 2H)

EXAMPLE 83
Synthesis of Compound 87

Methyl 3-(2-bromophenyl)-4-nitrobutyrate (409 mg, 1.4 mmol), 3,4-dihydroxybenzaldehyde (186 mg, 1.4 mmol) and 4-aminomethylpyridine (0.28 mL, 2.8 mmol) were heated under reflux in ethanol for 20 hours. After evaporating ethanol under reduced pressure, the residue was purified by silica gel column chromatography (eluted with chloroform/methanol=95/5) to give Compound 87 (81 mg, yield 11%).

$^1$HNMR (DMSO-d$_6$, 300 MHz) δ9.22 (br s, 1H), 8.94 (br s, 1H), 8.44 (d, J=5.5 Hz, 2H), 7.81 (d, J=7.9 Hz, 1H), 7.61 (d, J=7.9 Hz, 1H), 7.44 (t, J=7.2 Hz, 1H), 7.22 (t, J=7.2 Hz, 1H), 7.13 (d, J=5.5 Hz, 1H), 6.81–6.55 (m, 4H), 5.88 (t, J=10.0 Hz, 1H), 4.84 (d, J=10.0 Hz, 1H), 4.61 (d, J=16.0 Hz, 1H), 4.44–4.35 (m, 1H), 4.00 (d, J=16.0 Hz, 1H), 3.09–2.99 (m, 1H), 2.75 (dd, J=16.0, 5.0 Hz, 1H)

EXAMPLE 84
Synthesis of Compound 88

Methyl 3-(2-bromophenyl)-4-nitrobutyrate (376 mg, 1.2 mmol), 3,4-dihydroxybenzaldehyde (172 mg, 1.2 mmol) and 1-(3-aminopropyl)imidazole (0.30 mL, 2.5 mmol) were heated under reflux in ethanol for 20 hours. After evaporating ethanol under reduced pressure, the residue was purified by silica gel column chromatography (eluted with chloroform/methanol=95/5) to give Compound 88 (32 mg, yield 9.1%).

$^1$HNMR (CDCl$_3$, 300 MHz) δ7.52–7.47 (m, 2H), 7.33–7.26 (m, 2H), 7.15–7.09 (m, 1H), 6.93–6.88 (m, 2H), 6.77–6.70 (m, 2H), 6.58–6.55 (m, 1H), 5.38 (t, J=10.0 Hz, 1H), 4.84 (d, J =10.0 Hz, 1H), 4.40–4.30 (m, 1H), 3.88 (t, J=6.5 Hz, 2H), 3.53–3.43(m, 1H), 3.02–2.74 (m, 3H), 2.05–1.86 (m, 2H)

EXAMPLE 85
Synthesis of Compound 90

Methyl 3-(2-bromophenyl)-4-nitrobutyrate (400 mg, 1.3 mmol), 3-pyridinecarbaldehyde (0.11 mL, 1.3 mmol) and 3,4-dihydroxybenzylamine hydrobromide (580 mg, 2.6 mmol) were heated under reflux in ethanol for 2 days. After evaporating ethanol under reduced pressure, the residue was purified by silica gel column chromatography (eluted with chloroform alone) to give Compound 90 (28 mg, yield 4.2%).

$^1$HNMR (DMSO-d$_6$, 300 MHz) δ8.87 (s, 1H), 8.83 (s, 1H), 8.58 (dd, J=5.0, 2.0 Hz, 1H), 8.41 (d, J=2.0 Hz, 1H), 7.83–7.74 (m, 2H), 7.63–7.60 (m, 1H), 7.46–7.39 (m, 2H), 7.25–7.20 (m, 1H), 6.58 (d, J=8.1 Hz, 1H), 6.45 (d, J=2.0 Hz, 1H), 6.10 (dd, J=8.1, 2.0 Hz, 1H), 6.00–5.92 (m, 1H), 4.89 (d, J=9.7 Hz, 1H), 4.78 (d, J=15.0 Hz, 1H), 4.34–4.25 (m, 1H), 3.54 (d, J=15.0 Hz, 1H), 3.09–3.00 (m, 1H), 2.77 (dd, J=17.0, 5.0 Hz, 1H)

EXAMPLE 86
Synthesis of Compound 91

Methyl 3-(2-bromophenyl)-4-nitrobutyrate (403 mg, 1.3 mmol), 3-hydroxybenzaldehyde (90 mg, 0.68 mmol) and 2-aminomethylpyridine (0.40 mL, 3.9 mmol) were heated under reflux in ethanol for 20 hours. After evaporating ethanol under reduced pressure, the residue was purified by silica gel column chromatography (eluted with chloroform/methanol=99/1) to give Compound 91 (110 mg, yield 18%).

$^1$HNMR (CDCl$_3$, 300 MHz) δ8.53–8.50 (m, 1H), 7.71–7.66 (m, 1H), 7.53 (d, J=7.7 Hz, 1H), 7.26–7.07 (m, 6H), 6.80–6.71 (m, 2H), 6.64 (d, J=7.7 Hz, 1H), 5.36 (t, J=8.8 Hz, 1H), 5.28 (d, J=15.0 Hz, 1H), 5.22 (d, J=8.8 Hz, 1H), 4.61–4.51 (m, 1H), 3.97 (d, J=15.0 Hz, 1H), 2.99 (dd, J=17.0, 5.1 Hz, 1H), 2.84–2.62 (m, 1H)

EXAMPLE 87
Synthesis of Compound 92
From Compound 1 (19 mg, 0.04 mmol) and 2-vinylpyridine (11 mg, 0.1 mmol), Compound 92 (21 mg, yield 100%) was obtained in the same manner as in Example 69.

$^1$HNMR (DMSO-d$_6$, 300 MHz) δ9.66 (br s, 1H), 8.57 (br s, 1H), 8.43 (br s, 1H), 8.17 (br s, 1H), 7.75–7.79 (m, 2H), 7.29–7.67 (m, 9H), 7.11 (d, J=8.0 Hz, 2H), 6.69 (d, J=8.0 Hz, 2H), 5.73 (t, J=10.8 Hz, 1H), 4.83 (d, J=9.7 Hz, 1H), 4.73 (d, J=15.2 Hz, 1H), 3.90–3.99 (m, 2H), 3.23 (dd, J=14,4, 12.8 Hz, 1H), 2.80 (dd, J=12.8, 1.6 Hz, 1H)

EXAMPLE 88
Synthesis of Compound 93
From methyl 3-(2-iodophenyl)-4-nitrobutyrate (7.1 g, 20 mmol), 3,4-dihydroxybenzaldehyde (2.8 g, 20 mmol) and 3-aminomethylpyridine (4.1 mL, 40 mmol), Compound 93 (5.3 g, yield 47%) was obtained in the same manner as in Example 1.

$^1$HNMR (DMSO-d$_6$, 300 MHz) δ8.93 (br s, 2H), 8.42 (dd, J=4.8, 1.6 Hz, 1H), 8.18 (d, J=1.6 Hz, 1H), 7.84 (dd, J=8.0, 1.3 Hz, 1H), 7.74 (d, J=7.2 Hz, 1H), 7.46–7.40 (m, 2H), 7.27 (dd, J=4.7, 0.7 Hz, 1H), 7.03 (td, J=8.0, 1.2 Hz, 1H), 6.77 (d, J=1.9 Hz, 1H), 6.64 (d, J=8.1 Hz, 1H), 6.59 (dd, J=8.1, 1.9 Hz, 1H), 5.76 (dd, J=10.4, 9.8 Hz, 1H), 4.79 (d, J=9.8 Hz, 1H), 4.65 (d, J=15.4 Hz, 1H), 4.16 (m, 1H), 4.03 (d, J=15.4 Hz, 1H), 2.98 (dd, J=16.9, 13.0 Hz, 1H), 2.69 (dd, J=16.9, 5.1 Hz, 1H)

EXAMPLE 89
Synthesis of Compound 94
Under an argon atmosphere, triethylamine (1.0 mL), vinyltributyltin (0.15 mL, 0.50 mmol) and Compound 93 (109 mg, 0.20 mmol) were added to a solution (2 mL) of palladium (II) diacetate (11 mg, 0.050 mmol) and tris(2-methylphenyl)phosphine (53 mg, 0.20 mmol) in DMF, followed by stirring at 80° C. for 5 hours. Next, the reaction solution was filtered through celite and purified by silica gel column chromatography (eluted with chloroform/methanol=19/1) to give Compound 94 (16 mg, yield 18%).

$^1$HNMR (DMSO-d$_6$, 300 MHz) δ9.22 (br s, 1H), 8.94 (br s, 1H), 8.42 (d, J=3.3 Hz, 1H), 8.20 (br s, 1H), 7.48–7.72 (m, 4H), 7.18–7.32 (m, 3H), 6.72 (s, 1H), 6.64 (d, J=7.9 Hz, 1H), 6.51 (d, J=7.9 Hz, 1H), 5.63–5.77 (m, 2H), 5.37 (d, J =11.5 Hz, 1H), 4.73–4.79 (m, 2H), 4.33 (m, 1H), 3.90 (d, J=15.6 Hz, 1H), 3.02 (dd, J=16.9, 12.8 Hz, 1H), 2.68 (dd, J=16.9, 5.1 Hz, 1H)

EXAMPLE 90
Synthesis of Compound 95
Under ice-cooling, ethanedithiol (0.063 mL, 0.75 mmol) and boron trifluoride-ether complex salt (0.095 mL, 0.75 mmol) were added to a solution (20 ml) of Compound 42 (74 mg, 0.15 mmol) in methylene chloride, followed by stirring at the same temperature for 1 hour. Next, the reaction solution was neutralized by adding an aqueous solution of sodium bicarbonate and extracted with chloroform. The extract was dried over sodium carbonate. After evaporating the solvent under reduced pressure, the residue was purified by silica gel column chromatography (eluted with chloroform/methanol=19/1) to give Compound 95 (41 mg, yield 52%).

$^1$HNMR (DMSO-d$_6$, 300 MHz) δ9.19 (br s, 1H), 8.91 (br s, 1H), 8.42 (d, J=4.0 Hz, 1H), 8.23 (br s, 1H), 7.77 (d, J=7.0 Hz, 1H), 7.67 (d, J=7.0 Hz, 1H), 7.48 (d, J=7.9 Hz, 1H), 7.27–7.31 (m, 3H), 6.73 (d, J=1.7 Hz, 1H), 6.64 (d, J =8.1 Hz, 1H), 6.53 (dd, J=8.1, 1.7 Hz, 1H), 6.18 (s, 1H), 5.80 (dd, J=10.8, 10.0 Hz, 1H), 4.79 (d, J=10.0 Hz, 1H), 4.73 (d, J=15.4 Hz, 1H), 4.59 (m, 1H), 3.95 (d, J=15.4 Hz, 1H), 3.38–3.59 (m, 4H), 2.99 (dd, J=16.8, 12.8 Hz, 1H), 2.72 (dd, J=16.8, 5.1 Hz, 1H)

EXAMPLE 91
Synthesis of Compound 96
From methyl 3-[2-(2-methyl-1-propenyl)phenyl]-4-nitrobutyrate (1.5 g, 5.4 mmol), 3,4-dihydroxybenzaldehyde (750 mg, 5.4 mmol) and 3-aminomethylpyridine (1.1 mL, 10.8 mmol), Compound 96 (1.4 g, yield 68%) was obtained in the same manner as in Example 1.

$^1$HNMR (DMSO-d$_6$, 300 MHz) δ9.18 (s, 1H), 8.89 (s, 1H), 8.41 (dd, J=3.7 Hz, 1H), 8.18 (s, 1H), 7.66 (dd, J=7.8, 1.0 Hz, 1H), 7.43 (d, J=7.8 Hz, 1H), 7.29–7.19 (m, 3H), 7.04 (d, J=7.8 Hz, 1H), 6.74 (dd, J=2.1, 1.9 Hz, 1H), 6.63 (d, J=8.2 Hz, 1H), 6.55 (dd, J=8.2, 2.1 Hz, 1H), 6.33 (s, 1H), 5.69 (dd, J=11.6, 9.8 Hz, 1H), 4.74 (d, J=9.8 Hz, 1H), 4.63 (d, J=15.6 Hz, 1H), 4.06–3.98 (m, 2H), 3.03 (dd, J=17.1, 13.1 Hz, 1H), 2.62 (dd, J=17.1, 4.9 Hz, 1H), 1.91 (d, J=1.2 Hz, 3H), 1.56 (d, J=1.2 Hz, 3H)

EXAMPLE 92
Synthesis of Compound 97
Under an argon atmosphere, diethylamine (0.5 mL), trimethylethynylsilane (0.14 mL, 0.20 mmol), copper (I) iodide (190 mg, 1.0 mmol) and Compound 93 (109 mg, 0.20 mmol) were added to a solution (2 mL) of palladium (II) diacetate (22 mg, 0.10 mmol) and triphenylphosphine (105 mg, 0.40 mmol) in DMF, followed by stirring at room temperature for 1 hour. Next, the reaction solution was filtered through celite and purified by silica gel column chromatography (eluted with chloroform/methanol=19/1) to give a trimethylsilylethynyl derivative (56 mg, yield 54%).

To a solution (10 mL) of the resulting trimetylsilylethynyl derivative in methanol was added potassium carbonate (140 mg, 1.0 mmol), followed by stirring at room temperature for 1 hour. Next, the reaction solution was neutralized with dilute hydrochloric acid and extracted with chloroform. The organic layer was dried over sodium carbonate. After evaporating the solvent under reduced pressure, the residue was purified by silica gel thin layer chromatography (developed with chloroform/acetonitrile=1/1) to give Compound 97 (21 mg, yield 44%).

$^1$HNMR (DMSO-d$_6$, 300 MHz)δ9.23 (s, 1H), 8.97 (s, 1H), 8.42 (br s, 1H), 8.18 (br s, 1H), 7.72 (d, J=7.8 Hz, 1H), 7.49–7.41 (m, 3H), 7.32–7.27 (m, 2H), 6.74 (d, J=2.0 Hz, 1H), 6.64 (d, J=8.0 Hz, 1H), 6.55 (dd, J=8.0, 2.0 Hz, 1H), 5.83 (dd, J=11.6, 9.9 Hz, 1H), 4.79 (d, J=9.9 Hz, 1H), 4.63 (d, J=15.6 Hz, 1H), 4.50 (s, 1H), 4.06–3.98 (m, 2H), 3.03 (dd, J=17.1, 13.1 Hz, 1H), 2.62 (dd, J=17.1, 4.9 Hz, 1H), 1.91 (d, J=1.2 Hz, 3H), 1.56 (d, J=1.2 Hz, 3H)

EXAMPLE 93
Synthesis of Compound 98
From methyl 3-(2-isopropylphenyl)-4-nitrobutyrate (300 mg, 1.1 mmol), 3,4-dihydroxybenzaldehyde (157 mg, 1.1 mmol) and 3-aminomethylpyridine (0.22 mL, 2.2 mmol), Compound 98 (123 mg, yield 24%) was obtained in the same manner as in Example 1.

$^1$HNMR (DMSO-d$_6$, 300 MHz) δ9.20 (s, 1H), 8.91 (s, 1H), 8.41 (dd, J=4.8, 1.5 Hz, 1H), 8.20 (d, J=1.8 Hz, 1H), 7.65 (d, J=7.9 Hz, 1H), 7.48 (d, J=7.9 Hz, 1H), 7.30–7.18 (m, 3H), 6.74 (d, J=1.8 Hz, 1H), 6.62 (d, J=8.1 Hz, 1H), 6.53 (dd, J=8.1, 1.8 Hz, 1H), 5.75 (dd, J=11.0, 10.4 Hz, 1H), 4.48 (d, J=9.7 Hz, 1H), 4.68 (d, J=15.4 Hz, 1H), 4.32 (m, 1H), 4.63 (d, J=15.4 Hz, 1H), 3.98 (d, J=15.4 Hz, 1H), 3.35 (m, 1H), 3.01 (dd, J=17.1, 12.8 Hz, 1H), 2.66 (dd, J=17.1, 4.8 Hz, 1H), 1.17 (d, J=6.8 Hz, 3H), 1.14 (d, J=6.8 Hz, 3H)

EXAMPLE 94
Synthesis of Compound 99

From methyl 3-(2-bromophenyl)-4-nitrobutyrate (602 mg, 2.0 mmol), 2-imidazolecarbaldehyde (192 mg, 2.0 mmol) and 3-aminomethylpyridine (0.41 mL, 4.0 mmol), Compound 99 (23 mg, yield 2.5%) was obtained in the same manner as in Example 1.

$^1$HNMR (DMSO-d$_6$, 300 MHz) δ10.3 (m, 1H), 8.49 (d, J=3.7 Hz, 1H), 8.34 (s, 1H), 7.62–7.54 (m, 2H), 7.33–7.14 (m, 6H), 5.78 (dd, J=10.4, 6.8 Hz, 1H), 5.26 (d, J=6.8 Hz, 1H), 5.09 (d, J=15.1 Hz, 1H), 4.42 (m, 1H), 4.15 (d, J=15.1 Hz, 1H), 2.94–2.84 (m, 2H)

EXAMPLE 95
Synthesis of Compound 100

From methyl 3-(2-bromophenyl)-4-nitrobutyrate (602 mg, 2.0 mmol), indole-3-carbaldehyde (290 mg, 2.0 mmol) and 3-aminomethylpyridine (0.41 mL, 4.0 mmol), Compound 100 (62 mg, yield 6.1%) was obtained in the same manner as in Example 1.

$^1$HNMR (DMSO-d$_6$, 300 MHz) δ9.49 (br s, 1H), 8.47 (d, J =3.7 Hz, 1H), 8.10 (br s, 1H), 7.65–7.45 (m, 3H), 7.38–7.09 (m, 7H), 6.97 (br s, 1H), 5.63 (m, 1H), 5.23 (d, J=14.9 Hz, 1H), 5.16 (d, J=9.6 Hz, 1H), 4.41 (m, 1H), 3.99 (d, J=14.9 Hz, 1H), 3.14 (dd, J=15.6, 5.1 Hz, 1H), 2.81 (m, 1H)

EXAMPLE 96
Synthesis of Compound 101

From methyl 3-(2-bromophenyl)-4-nitrobutyrate (602 mg, 2.0 mmol), 4-pyridinecarbaldehyde (210 mg, 2.0 mmol) and 3-aminomethylpyridine (0.41 mL, 4.0 mmol), Compound 101 (73 mg, yield 7.8%) was obtained in the same manner as in Example 1.

$^1$HNMR (DMSO-d$_6$, 300 MHz) δ8.52 (d, J=2.0 Hz, 1H), 8.46 (dd, J=4.7, 1.5 Hz, 1H), 8.35 (d, J=4.7, 1.1 Hz, 1H), 8.06 (d, J=2.0 Hz, 1H), 7.85–7.75 (m, 2H), 7.62 (d, J =8.0 Hz, 1H), 7.47–7.15 (m, 5H), 6.04 (dd, J=11.6, 9.9 Hz, 1H), 5.24 (d, J=9.9 Hz, 1H), 4.54–4.38 (m, 2H), 4.27 (d, J =15.7 Hz, 1H), 3.06 (d, J=17.1, 13.0 Hz, 1H), 2.79 (dd, J =17.1, 5.1 Hz, 1H)

EXAMPLE 97
Synthesis of Compound 102

From methyl 3-(2-bromophenyl)-4-nitrobutyrate (602 mg, 2.0 mmol), 2-pyridinecarbaldehyde (214 mg, 2.0 mmol) and 3-aminomethylpyridine (0.41 mL, 4.0 mmol), Compound 102 (96 mg, yield 10%) was obtained in the same manner as in Example 1.

$^1$HNMR (DMSO-d$_6$, 300 MHz) δ8.63 (m, 1H), 8.50 (dd, J=4.7, 1.4 Hz, 1H), 8.23 (d, J=4.7 Hz, 1H), 7.72–7.53 (m, 3H), 7.31–7.04 (m, 6H), 5.73 (dd, J=10.7, 7.0 Hz, 1H), 5.14–5.08 (m, 2H), 4.47 (m, 1H), 3.97 (d, J=15.2 Hz, 1H), 3.02–2.60 (m, 2H)

EXAMPLE 98
Synthesis of Compound 103

From methyl 3-(2-bromophenyl)-4-nitrobutyrate (602 mg, 2.0 mmol), 4-imidazolecarbaldehyde (192 mg, 2.0 mmol) and 3-aminomethylpyridine (0.41 mL, 4.0 mmol), Compound 103 (31 mg, yield 3.4%) was obtained in the same manner as in Example 1.

$^1$HNMR (DMSO-d$_6$, 300 MHz) δ12.10 (br s, 1H), 8.39 (dd, J=4.7, 1.5 Hz, 1H), 8.25 (d, J=1.5 Hz, 1H), 7.74 (d, J=7.4 Hz, 1H), 7.63–7.60 (m, 2H), 7.52 (d, J=7.8 Hz, 1H), 7.42 (t, J=7.4 Hz, 1H), 7.29–7.17 (m, 3H), 5.93 (dd, J=11.6, 8.6 Hz, 1H), 5.14 (d, J=8.6 Hz, 1H), 4.64 (d, J=15.4 Hz, 1H), 4.36 (m, 1H), 4.22 (d, J=15.4 Hz, 1H), 3.01 (dd, J=16.9, 13.1 Hz, 1H), 2.67 (dd, J=16.9, 5.1 Hz, 1H)

EXAMPLE 99
Synthesis of Compound 104

From methyl 3-(2-bromophenyl)-4-nitrobutyrate (301 mg, 1.0 mmol), piperonal (150 mg, 1.0 mmol) and 3-aminomethylpyridine (0.21 mL, 2.0 mmol), Compound 104 (258 mg, yield 51%) was obtained in the same manner as in Example 1

$^1$HNMR (CDCl$_3$, 300 MHz) δ8.56 (dd, J=5.0, 1.6 Hz, 1H), 8.26 (d, J=1.8 Hz, 1H), 7.59–7.52 (m, 2H), 7.34–7.12 (m, 6H), 6.77 (d, J=7.9 Hz, 1H), 6.65 (d, J=1.7 Hz, 1H), 6.57 (dd, J=7.9, 1.9 Hz, 1H), 6.03 (d, J=1.3 Hz, 1H), 5.24–5.19 (m, 2H), 4.79 (d, J=9.2 Hz, 1H), 4.33 (m, 1H), 3.85 (d, J=14.9 Hz, 1H), 3.06 (dd, J=17.6, 5.0 Hz, 1H), 2.80 (m, 1H), 1.91 (d, J=1.2 Hz, 3H), 1.56 (d, J=1.2 Hz, 3H)

EXAMPLE 100
Synthesis of Compound 105

From methyl 3-(2-bromophenyl)-4-nitrobutyrate (301 mg, 1.0 mmol), 3-formylbenzoic acid (150 mg, 1.0 mmol) and 3-aminomethylpyridine (0.20 mL, 2.0 mmol), Compound 105 (14 mg, yield 2.7%) was obtained in the same manner as in Example 1.

$^1$HNMR (DMSO-d$_6$, 400 MHz) δ13.07 (br s, 1H), 8.41 (dd, J=4.9, 1.7 Hz, 1H), 8.03 (d, J=1.9 Hz, 1H), 7.85 (m, 1H), 7.84–7.80 (m, 2H), 7.62 (dd, J=8.1, 1.2 Hz, 1H), 7.55 (d, J =7.8 Hz, 1H), 7.45–7.33 (m, 3H), 7.25–7.17 (m, 2H), 6.01 (dd, J=11.5, 9.7 Hz, 1H), 5.24 (d, J=9.7 Hz, 1H), 4.50–4.31 (m, 3H), 3.11 (dd, J=17.1, 12.9 Hz, 1H), 2.78 (dd, J=17.1, 4.9 Hz, 1H)

EXAMPLE 101
Synthesis of Compound 106

From methyl 3-(2-bromophenyl)-4-nitrobutyrate (124 mg, 0.40 mmol), N-trityl-5-benzimidazolecarbaldehyde (192 mg, 2.0 mmol) and 3-aminomethylpyridine (0.082 mL, 0.80 mmol), an N-trityl derivative of Compound 106 was obtained in the same manner as in Example 1.

Next, trifluoroacetic acid (0.5 mL) was added to a solution (10 mL) of this N-trityl derivative in methanol, followed by stirring at room temperature for 3 hours. After evaporating the solvent under reduced pressure, the residue was purified by silica gel thin layer chromatography (developed with chloroform/methanol=9/1) to give Compound 106 (32 mg, yield 16%).

$^1$HNMR (CDCl$_3$, 300 MHz) δ8.48 (dd, J=4.8, 1.4 Hz, 1H), 8.09 (br s, 2H), 7.59–7.50 (m, 4H), 7.27–7.25 (m, 4H), 7.15–7.08 (m, 2H), 5.44 (m, 1H), 5.13 (d, J=14.9 Hz, 1H), 5.03 (d, J=5.1 Hz, 1H), 4.23 (m, 1H), 3.75 (d, J=14.9 Hz, 1H), 3.09 (dd, J=17.6, 5.1 Hz, 1H), 2.86 (m, 1H)

EXAMPLE 102
Synthesis of Compounds 107 and 108

Compound 14 (10 mg, 0.02 mmol) was optically resolved by high performance liquid chromatography (HPLC) with the use of Chiralcel OD (0.46 cm in diameter, 25 cm in length; eluent: ispropylamine: n-hexane: diethylamine=4:6: 0.01) to give the (+)-optical isomer of Compound 14, i.e., Compound 107 (2.1 mg, 98% ee, yield 21%) and the (−)-optical isomer thereof, i.e., Compound 108 (1.3 mg, 86% ee, yield 13%).

Compound 107: $[\alpha]^{28}{}_D$=+90.7° (c=0.10, methanol).
Compound 108: $[\alpha]^{28}{}_D$=−85.50° (c=0.04, methanol).

EXAMPLE 103
Synthesis of Compound 109

From methyl 3-(2-bromophenyl)-4-nitrobutyrate (602 mg, 2.0 mmol), 4-hydroxy-3-nitrobenzaldehyde (330 mg, 2.0 mmol) and 3-aminomethylpyridine (0.40 mL, 4.0 mmol), Compound 109 (34 mg, yield 3.4%) was obtained in the same manner as in Example 1.

$^1$HNMR (DMSO-d$_6$, 300 MHz) δ11.16 (br s, 1H), 8.30 (m, 1H), 8.04 (br s, 1H), 7.92 (d, J=2.2 Hz, 1H), 7.74 (d, J=6.8 Hz, 1H), 7.59 (d, J=6.8 Hz, 1H), 7.45–7.33 (m, 3H), 7.23–7.14 (m, 2H), 6.92 (d, J=8.4 Hz, 1H), 5.98 (dd, J=11.3, 10.0 Hz, 1H), 5.17 (d, J=10.0 Hz, 1H), 4.51 (d, J=15.6 Hz, 1H), 4.41 (m, 1H), 4.10 (d, J=15.6 Hz, 1H), 3.02 (dd, J=17.2, 12.8 Hz, 1H), 2.74 (dd, J=17.2, 5.1 Hz, 1H)

EXAMPLE 104
Synthesis of Compound 110

Compound 109 (10 mg, 0.019 mmol) obtained in Example 103 was dissolved in ethanol (5.0 mL). After adding palladium-carbon (10%, 1.0 mg) thereto, the mixture was stirred under a hydrogen atmosphere at room temperature for 5 hours. Next, the palladium-carbon was removed by filtration and the filtrate was purified by preparative thin layer chromatography (developed with chloroform/methanol=95/5) to give Compound 110 (4.1 mg, yield 44%.).

$^1$HNMR (CDCl$_3$, 300 MHz) δ8.51 (br s, 1H), 8.04 (br s, 1H), 7.83 (d, J=7.9 Hz, 1H), 7.56 (d, J=7.3 Hz, 1H), 7.41–7.26 (m, 3H), 7.11 (m, 1H), 6.96–6.95 (m, 2H), 6.22 (d, J=7.2 Hz, 1H), 5.31–5.20 (m, 2H), 4.63 (d, J=9.4Hz, 1H), 4.32 (m, 1H), 3.98 (d, J=14.9 Hz, 1H), 3.07 (dd, J=5.0, 17.6 Hz. 1H), 2.70 (m, 1H)

EXAMPLE 105
Synthesis of Compound 111

Methyl 3-(2-bromophenyl)-4-nitrobutyrate (903 mg, 3.0 mmol), 2-nitrobenzaldehyde (453 mg, 3.0 mmol) and 3-aminomethylpyridine (0.61 mL, 6.0 mmol) were heated under reflux in acetic acid/ethanol (1/1, 2 mL) for 5 hours. After evaporating the solvent under reduced pressure, the residue was purified by silica gel column chromatography (eluted with chloroform/methanol=95/5) to give Compound 111 (230 mg, yield 15%).

$^1$HNMR (CDCl$_3$, 270 MHz) δ8.49 (dd, J=4.6, 1.3 Hz, 1H), 8.06 (br s, 1H), 7.94 (dd, J=5.9, 3.6 Hz, 1H), 7.58–7.55 (m, 4H), 7.33–7.12 (m, 5H), 5.75 (br s, 1H), 5.53 (m, 1H), 4.89 (d, J=14.9 Hz, 1H), 4.35 (m, 1H), 4.19 (d, J=14.9 Hz, 1H), 2.93–2.86 (m, 2H)

EXAMPLE 106
Synthesis of Compound 112

Palladium-carbon (10 mg) was added to a solution (2 mL) of Compound 111 (26 mg, 0.05 mmol) in ethanol under a hydrogen atmosphere, followed by stirring at room temperature for 5 hours. Next, the catalyst was removed by filtration through celite, and the solvent was evaporated under reduced pressure. The obtained residue was purified by silica gel thin layer chromatography (chloroform/methanol=1/20) to give Compound 112 (5.4 mg, yield 21%).

$_1$HNMR (CDCl$_3$, 300 MHz) δ8.50 (dd, J=4.8, 1.5 Hz, 1H), 8.18 (br s, 1H), 7.59–7.53 (m, 2H), 7.45–7.40 (m, 2H), 7.37–7.24 (m, 4H), 7.40–7.01 (m, 2H), 6.53 (br s, 1H), 5.66 (m, 1H), 5.13–5.06 (m, 2H), 4.39 (m, 1H), 3.95 (d, J=14.7 Hz, 1H), 3.01 (dd, J=17.6, 4.9 Hz, 1H), 2.72 (m, 1H)

EXAMPLE 107
Synthesis of Compound 113

From methyl 3-(2-bromophenyl)-4-nitrobutyrate (171 mg, 0.57 mmol), 3-(1-tritylimidazol-4-yl)-2-propen-1-al (207 mg, 0.57 mmol) and 3-aminomethylpyridine (0.116 mL, 1.1 mmol), Compound 113 (123 mg, yield 30%) was obtained in the same manner as in Example 1.

$^1$HNMR (CDCl$_3$, 300 MHz) δ10.93 (m, 1H), 8.54 (dd, J=4.6, 1.4 Hz, 1H), 8.48 (br s, 1H), 7.56–7.47 (m, 2H), 7.32–6.99 (m, 19H), 6.69 (br s, 1H), 6.57 (d, J=12.5 Hz, 1H), 5.47 (dd, J=11.2, 10.8 Hz, 1H), 4.41–4.27 (m, 5H), 2.84 (dd, J=18.0, 5.8 Hz, 1H), 2.55 (m, 1H)

EXAMPLE 108
Synthesis of Compound 114

Hydrochloric acid (1 mol/L, 1 mL) was added to a solution (10 mL) of Compound 113 (72 mg, 0.1 mmol) in tetrahydrofuran, followed by stirring at room temperature for 5 hours. Next, the reaction solution was poured into a solution of sodium bicarbonate to neutralize the reaction solution, and the mixture was then extracted with chloroform. After drying the extract over magnesium sulfate, the solvent was evaluated under reduced pressure. The obtained residue was purified by silica gel thin layer chromatography (chloroform/methanol=1/20) to give Compound 114 (23 mg, yield 48%).

$^1$HNMR (CD$_3$OD, 300 MHz) δ9.01 (br s, 1H), 8.70 (dd, J 14.1, 3.8 Hz, 1H), 8.64 (br s, 1H), 8.08 (br d, J=7.3 Hz, 1H), 7.74–7.69 (m, 2H), 7.61–7.57 (m, 2H), 7.47 (dd, J=7.3, 6.8 Hz, 1H), 7.29 (td, J=7.9, 1.6 Hz, 1H), 7.02 (br s, 1H), 5.72 (dd, J=10.8, 10.4 Hz, 1H), 4.99–4.92 (m, 4H), 4.54 (m, 1H), 2.82 (m, 2H)

EXAMPLE 109
Synthesis of Compound 115

From methyl 3-(2-bromophenyl)-4-nitrobutyrate (602 mg, 2.0 mmol), 3,4-bis(t-butoxycarbonylamino) benzaldehyde (152 mg, 1.0 mmol) and 3-aminomethylpyridine (0.20 mL, 2.0 mmol), Compound 115 (192 mg, yield 15%) was obtained in the same manner as in Example 1.

$^1$HNMR (CDCl$_3$, 300 MHz) δ8.52–8.46 (m, 2H), 7.64 (d, J=7.7 Hz, 1H), 7.58 (d, J=8.4 Hz, 1H), 7.52 (dd, J=7.9, 1.1 Hz, 1H), 7.35 (d, J=7.7 Hz, 1H), 7.30–7.20 (m, 3H), 7.08 (m, 1H), 7.67 (br s, 1H), 4.97 (dd, J=10.9, 9.5 Hz, 1H), 4.41 (d, J=14.6 Hz, 1H), 4.17 (m, 1H), 3.82 (d, J=9.5 Hz, 1H), 3.79 (d, J=14.6 Hz, 1H), 3.00 (m, 1H), 2.80 (m, 1H), 1.52 (s, 9H), 1.46 (s, 9H)

EXAMPLE 110
Synthesis of Compound 116

Compound 115 (11 mg, 0.015 mmol) and 3-pyridinecarbaldehyde (0.003 mL, 0.03 mmol) were dissolved in trifluoroacetic acid (3 mL), followed by stirring at room temperature for 5 hours. Next, the reaction solution was poured into a solution of sodium bicarbonate to neutralize the reaction solution, and the mixture was then extracted with chloroform. After drying the extract over magnesium sulfate, the solvent was evaporated under reduced pressure. The obtained residue was purified by silica gel thin layer chromatography (developed with chloroform/methanol=1/20) to give Compound 116 (3.3 mg, yield 36%).

¹HNMR (DMSO-d$_6$, 300 MHz) δ9.34 (s, 1H), 8.74 (d, J=4.4 Hz, 1H), 8.60 (d, J=4.9 Hz, 1H), 8.54 (dd, J=8.0, 1.8 Hz, 1H), 8.29 (br s, 1H), 7.96 (d, J=8.3 Hz, 1H), 7.81 (d, J=8.0 Hz, 1H), 7.71–7.59 (m, 6H), 7.53 (d, J=8.4 Hz, 1H), 7.46 (t, J=8.4 Hz, 1H), 7.33 (d, J=8.4 Hz, 1H), 7.24 (m, 1H), 6.06 (dd, J=11.2, 10.0 Hz, 1H), 5.37 (d, J=10.0 Hz, 1H), 4.56 (m, 1H), 3.10 (dd, J=17.2, 12.4 Hz, 1H), 2.82 (dd, J=17.2, 5.3 Hz, 1H)

EXAMPLE 111
Synthesis of Compounds 117 and 118

Compound 115 (45 mg, 0.064 mmol) was dissolved in trifluoroacetic acid (3 mL), followed by stirring at room temperature for 2 hours. Next, the reaction solution was poured into a solution of sodium bicarbonate to neutralize the reaction solution, and the mixture was then extracted with chloroform. After drying the extract over magnesium sulfate, the solvent was evaporated under reduced pressure. The obtained residue was purified by silica gel thin layer chromatography (developed with chloroform/methanol=1/20) to give Compound 117 (20 mg, yield 63%) and Compound 118 (5.1 mg, yield 14%).

Compound 117

¹HNMR (DMSO-d$_6$, 300 MHz) δ8.44 (dd, J=4.6, 1.3 Hz, 1H), 8.23 (d, J=2.2 Hz, 1H), 7.79 (d, J=4.9 Hz, 1H), 7.60 (d, J=7.9 Hz, 1H), 7.48 (d, J=7.9 Hz, 1H), 7.42 (m, 1H), 7.31 (dd, J=7.9, 4.8 Hz, 1H), 7.21 (m, 1H), 6.45 (d, J=1.8 Hz, 1H), 6.43 (d, J=8.1 Hz, 1H), 6.34 (dd, J=8.1, 1.8 Hz, 1H), 5.79 (dd, J=11.4, 10.0 Hz, 1H), 4.78 (d, J=15.3 Hz, 1H), 4.67–4.64 (m, 2H), 4.54 (br s, 1H), 4.29 (m, 1H), 3.88 (d, J=15.3 Hz, 1H), 2.99 (dd, J=17.0, 12.9 Hz, 1H), 2.71 (dd, J=17.0, 5.0 Hz, 1H)

Compound 118

¹HNMR (DMSO-d$_6$, 300 MHz) δ14.0 (br s, 1H), 8.32 (d, J=7.2 Hz, 1H), 8.05 (br s, 1H), 7.81 (d, J=7.9 Hz, 1H), 7.47–7.36 (m, 4H), 7.26–7.16 (m, 3H), 6.04 (dd, J=11.0, 10.1 Hz, 1H), 5.26 (d, J=10.1 Hz, 1H), 4.48–4.41 (m, 2H), 4.23 (d, J=15.6 Hz, 1H), 3.10 (dd, J=17.1, 13.0 Hz, 1H), 2.83 (dd, J=17.1, 5.0 Hz, 1H)

EXAMPLE 112
Synthesis of Compound 119

From methyl 3-(2-bromophenyl)-4-nitrobutyrate (1.2 g, 4.0 mmol), 3,4-dimethoxybenzaldehyde (664 mg, 4.0 mmol) and 3-aminomethylpyridine (0.80 mL, 8.0 mmol), Compound 119 (1.35 g, yield 64%) was obtained in the same manner as in Example 1.

¹HNMR (CDCl$_3$, 300 MHz) δ8.36 (d, J=4.4 Hz, 1H), 8.14 (br s, 1H), 7.77 (d, J=6.9 Hz, 1H), 7.62 (d, J=8.0 Hz, 1H), 7.46 (dd, J=7.7, 7.3 Hz, 1H), 7.36 (d, J=7.7 Hz, 1H), 7.21 (m, 2H), 6.97 (br s, 1H), 6.84–6.77 (m, 2H), 5.95 (t, J=10.8 Hz, 1H), 5.04 (d, J=10.8 Hz, 1H), 4.48–4.26 (m, 3H), 3.71 (s, 3H), 3.58 (s, 3H), 3.03 (dd, J=16.8, 12.8 Hz, 1H), 2.78 (dd, J=16.8, 5.3 Hz, 1H)

EXAMPLE 113
Synthesis of Compound 120

From methyl 3-(2-bromophenyl)-4-nitrobutyrate (301 mg, 1.0 mmol), vanillin (152 mg, 1.0 mmol) and 3-aminomethylpyridine (0.20 mL, 2.0 mmol), Compound 120 (320 mg, yield 63%) was obtained in the same manner as in Example 1.

¹HNMR (DMSO-d$_6$, 300 MHz) δ9.16 (br s, 1H), 8.36 (dd, J=4.4 Hz, 1H), 8.13 (br s, 1H), 7.78 (d, J=7.5 Hz, 1H), 7.62 (d, J=8.1 Hz, 1H), 7.46 (t, J=7.5 Hz, 1H), 7.37 (d, J=8.1 Hz, 1H), 7.26–7.20 (m, 2H), 6.93 (br s, 1H), 6.68–6.61 (m, 2H), 5.93 (dd, J=10.6, 9.8 Hz, 1H), 4.98 (d, J=9.8 Hz, 1H), 4.44–4.28 (m, 3H), 3.59 (s, 3H), 2.98 (dd, J=16.9, 12.8 Hz, 1H), 2.76 (dd, J=16.9, 5.0 Hz, 1H)

EXAMPLE 114
Synthesis of Compound 121

From methyl 3-cyclohexyl-4-nitrobutyrate (463 mg, 2.0 mmol), 3,4-dihydroxybenzaldehyde (264 mg, 8.7 mmol) and 3-aminomethylpyridine (0.407 mL, 4.0 mmol), Compound 121 (162 mg, yield 19%) was obtained in the same manner as in Example 1.

¹HNMR (DMSO-d$_6$, 300 MHz) δ9.18 (br s, 2H), 8.96 (br s, 1H), 8.42 (dd, J=4.8, 1.5 Hz, 1H), 7.46 (d, J=8.1 Hz, 1H), 7.28 (dd, J=7.9, 4.8 Hz, 1H), 6.65 (d, J=8.2 Hz, 1H), 6.64 (s, 1H), 6.46 (d, J=8.2 Hz, 1H), 5.17 (dd, J=9.7, 9.1 Hz, 1H), 4.81 (d, J=15.4 Hz, 1H), 4.61 (d, J=9.1 Hz, 1H), 4.09 (m, 1H), 3.50 (d, J=15.4 Hz, 1H), 2.63–2.51 (m, 2H), 1.67–1.52 (m, 4H), 1.46 (m, 1H), 1.26–1.07 (m, 6H)

EXAMPLE 115
Synthesis of Compound 122

From methyl 3-(2-bromophenyl)-4-nitrobutyrate (22 mg, 0.073 mmol), 3-acetylamino-4-hydroxybenzaldehyde (13 mg, 0.073 mmol) and 3-aminomethylpyridine (0.015 mL, 0.146 mmol), Compound 122 (18.6 mg, yield 47%) was obtained in the same manner as in Example 1.

¹HNMR (CDCl$_3$, 300 MHz) δ8.64 (br s, 1H), 7.98 (br s, 1H), 7.82 (d, J=7.9 Hz, 1H), 7.61–7.36 (m, 3H), 7.31–7.11 (m, 3H), 6.73 (d, J=8.3 Hz, 1H), 6.57 (dd, J=8.3, 1.1 Hz, 1H), 5.29 (m, 1H), 5.11 (d, J=15.2 Hz, 1H), 4.73 (d, J=9.5 Hz, 1H), 4.40 (m, 1H), 4.07 (d, J=15.2 Hz, 1H), 3.07 (m, 1H), 2.80 (m, 1H), 2.74 (s, 3H)

EXAMPLE 116
Synthesis of Compounds 123 and 124

From methyl 5-methyl-3-nitromethyl-4-hexenoate (301 mg, 1.0 mmol), 3,4-dihydroxybenzaldehyde (152 mg, 1.0 mmol) and 3-aminomethylpyridine (0.20 mL, 2.0 mmol), Compound 123 (130 mg, yield 16%) and Compound 124 (43 mg, yield 5.9%) were obtained in the same manner as in Example 1.

Compound 123

¹HNMR (CDCl$_3$, 300 MHz) δ8.64 (d, J=4.7 Hz, 1H), 8.53 (d, J=4.7 Hz, 1H), 8.39 (br s, 1H), 8.21 (br s, 1H), 7.45–7.40 (m, 2H), 7.32–7.22 (m, 2H), 5.14 (d, J=15.4 Hz, 1H), 4.87 (d, J=9.4 Hz, 1H), 4.86 (s, 1H), 4.63 (dd, J=11.0, 9.4 Hz, 1H), 3.73 (d, J=15.4 Hz, 1H), 3.16 (m, 1H), 2.82 (dd, J=17.8, 4.9 Hz, 1H), 2.48 (dd, J=17.8, 12.7 Hz, 1H), 1.67 (s, 3H), 1.62 (s, 3H)

Compound 124

¹HNMR (CDCl$_3$, 300 MHz) δ8.43 (d, J=3.5 Hz, 1H), 7.96 (br s, 1H), 7.76 (d, J=7.7 Hz, 1H), 7.36 (dd, J=8.0, 4.9 Hz, 1H), 6.72 (d, J=8.0 Hz, 1H), 6.60 (d, J=1.9 Hz, 1H), 6.40 (dd, J=8.0, 1.9 Hz, 1H), 5.02 (d, J=14.8 Hz, 1H), 4.88 (d, J=9.4 Hz, 1H), 4.67–4.53 (m, 2H), 4.05 (d, J=14.8 Hz, 1H), 3.40 (m, 1H), 2.76 (dd, J=17.8, 5.0 Hz, 1H), 2.48 (dd, J=17.8, 12.7 Hz, 1H), 1.68 (s, 3H), 1.62 (s, 3H)

EXAMPLE 117
Synthesis of Compound 125

From methyl 3-(2-bromophenyl)-4-nitrobutyrate (105 mg, 0.5 mmol), 3-carboxy-4-hydroxybenzaldehyde (83 mg, 0.50 mmol) and 3-aminomethylpyridine (0.11 mL, 1.0 mmol), Compound 125 (20 mg, yield 7.7%) was obtained in the same manner as in Example 1.

¹HNMR (DMSO-d$_6$, 300 MHz) δ8.38 (br s, 1H), 8.13 (br s, 1H), 7.60 (dd, J=7.9, 1.0 Hz, 1H), 7.75 (br s, 1H), 7.59 (d, J=7.9 Hz, 1H), 7.45–7.38 (m, 2H), 7.26–7.19 (m, 3H), 6.61 (d, J=8.3 Hz, 1H), 5.92 (dd, J=10.8, 9.7 Hz, 1H), 4.94 (d, J=9.7 Hz, 1H), 4.54 (d, J=16.4 Hz, 1H), 4.38 (m, 1H), 4.15 (d, J=16.4 Hz, 1H), 3.07 (dd, J=17.1, 13.0 Hz, 1H), 2.74 (dd, J=17.1, 5.0 Hz, 1H)

EXAMPLE 118
Synthesis of Compound 126

From methyl 3-(2-bromophenyl)-4-nitrobutyrate (79 mg, 0.263 mmol), 1-benzyl-5-formyl-2-pyridone (56 mg, 0.263 mmol) and 3-aminomethylpyridine (0.054 mL, 0.526 mmol), Compound 126 (29 mg, yield 19%) was obtained in the same manner as in Example 1.

$^1$HNMR (CDCl$_3$, 300 MHz) δ8.46 (d, J=4.8 Hz, 1H), 8.30 (br s, 1H), 7.78 (m, 1H), 7.64–7.56 (m, 2H), 7.39–7.13 (m, 9H), 6.65 (m, 1H), 6.26 (t, J=6.6 Hz, 1H), 5.85 (m, 1H), 5.19 (s, 2H), 4.89 (d, J=7.5 Hz, 1H), 4.80 (d, J=15.3 Hz, 1H), 4.44–4.39 (m, 2H), 2.95–2.90 (m, 2H)

EXAMPLE 119
Synthesis of Compound 127

From methyl 3-(2-bromophenyl)-4-nitrobutyrate (105 mg, 0.50 mmol), benzaldehyde (53 mg, 1.0 mmol) and 3-aminomethylpyridine (0.11 mL, 1.0 mmol), Compound 127 (110 mg, yield 24%) was obtained in the same manner as in Example 1.

$^1$HNMR (CDCl$_3$, 300 MHz) δ8.55 (dd, J=4.7, 1.7 Hz, 1H), 8.21 (d, J=1.8 Hz, 1H), 7.58 (dd, J=7.9, 1.2 Hz, 1H), 7.51 (dt, J=7.9, 1.8 Hz, 1H), 7.45–7.37 (m, 3H), 7.33–7.11 (m, 6H), 5.32–5.21 (m, 2H), 4.88 (d, J=9.0 Hz, 1H), 4.38 (m, 1H), 3.80 (d, J=14.9 Hz, 1H), 3.07 (dd, J=17.6, 5.2 Hz, 1H), 2.83 (m, 1H)

EXAMPLE 120
Synthesis of Compound 128

From methyl 3-(2-bromophenyl)-4-nitrobutyrate (105 mg, 0.50 mmol), 4-fluorobenzaldehyde (62 mg, 0.50 mmol) and 3-aminomethylpyridine (0.11 mL, 1.0 mmol), Compound 128 (160 mg, yield 33%) was obtained in the same manner as in Example 1.

$^1$HNMR (DMSO-d$_6$, 300 MHz) δ8.37 (dd, J=5.0, 1.5 Hz, 1H), 8.08 (d, J=1.5 Hz, 1H), 7.77 (dd, J=8.0, 1.5 Hz, 1H), 7.62 (dd, J=8.0, 1.3 Hz, 1H), 7.47–7.34 (m, 4H), 7.26–7.12 (m, 2H), 7.11 (d, J=8.9 Hz, 1H), 7.08 (d, J=8.9 Hz, 1H), 5.95 (dd, J=11.7, 9.8 Hz, 1H), 5.15 (d, J=9.8 Hz, 1H), 4.48–4.43 (m, 3H), 3.05 (dd, J=17.0, 13.4 Hz, 1H), 2.77 (dd, J=17.0, 5.5 Hz, 1H)

EXAMPLE 121
Synthesis of Compound 129

From methyl 3-(2-bromophenyl)-4-nitrobutyrate (105 mg, 0.50 mmol), 3,3-dimethylacrylaldehyde (0.048 mL, 0.50 mmol) and 3-aminomethylpyridine (0.102 mL, 1.0 mmol), Compound 129 (48 mg, yield 22%) was obtained in the same manner as in Example 1.

$^1$HNMR (CDCl$_3$, 300 MHz) δ8.56 (br s, 1H), 7.67 (dd, J=8.2, 1.7 Hz, 1H), 7.59 (dd, J=8.2, 1.1 Hz, 1H), 7.37–7.25 (m, 3H), 7.20–7.14 (m, 2H), 5.07–5.01 (m, 2H), 4.54 (d, J=15.4 Hz, 1H), 4.31 (m, 1H), 4.14–3.99 (m, 2H), 2.94 (dd, J=17.4, 5.3 Hz, 1H), 2.71 (dd, J=17.4, 11.9 Hz, 1H), 1.33 (s, 3H), 1.31 (s, 3H)

EXAMPLE 122
Synthesis of Compounds 130 and 131

[Step 1]

From a mixture of 3-(6-methoxypyridyl)carbaldehyde and 3-(2-methoxypyridyl)carbaldehyde (4/1, 274 mg, 2.0 mmol), methyl 3-(2-bromophenyl)-4-nitrobutyrate (602 mg, 2.0 mmol) and 3-aminomethylpyridine (0.407 mL, 4.0 mmol), a crude piperidone Compound having a methoxypyridyl group (370 mg, yield 37%) was obtained in the same manner as in the synthesis of Compound 111.

FAB-MS (m/z) 499, 497 (M+H)$^+$

[Step 2]

The above methoxypyridyl Compound (120 mg, 0.24 mmol) was dissolved in a 60% solution of hydrogen bromide in acetic acid, followed by stirring at 90° C. for 3 hours. Next, the solvent was evaporated under reduced pressure, and the residue was diluted with chloroform/methanol (9/1), subsequently neutralized with a solution of sodium hydroxide (1 mol/L), and then extracted with chloroform. After the extract was washed with a saturated brine and dried over sodium sulfate, the solvent was evaporated under reduced pressure. The residue was purified by silica gel thin layer chromatography (developed with chloroform/methanol=9/1) to give Compound 130 (7.6 mg, yield 6.2%) and Compound 131 (28 mg, yield 23%) as the target demethylation products.

Compound 130

$^1$HNMR (CDCl$_3$, 300 MHz) δ12.4 (br s, 1H), 8.46 (d, J=4.8 Hz, 1H), 8.30 (br s, 1H), 7.64–7.56 (m, 2H), 7.36–7.13 (m, 6H), 6.26 (t, J=6.6 Hz, 1H), 5.85 (m, 1H), 4.89 (d, J=7.5 Hz, 1H), 4.80 (d, J=15.3 Hz, 1H), 4.44–4.39 (m, 2H), 2.95–2.90 (m, 2H)

Compound 131

$^1$HNMR (CDCl$_3$, 300 MHz) δ12.8 (br s, 1H), 8.51 (d, J=3.5 Hz, 1H), 8.34 (br s, 1H), 7.58–7.51 (m, 2H), 7.31–7.12 (m, 6H), 6.53 (d, J=9.5 Hz, 1H), 5.32 (m, 1H), 5.01 (d, J=15.2 Hz, 1H), 4.73 (d, J=9.3 Hz, 1H), 4.37 (m, 1H), 4.17 (d, J=15.2 Hz, 1H), 3.06 (dd, J=17.6, 15.1 Hz, 1H), 2.82 (m, 1H)

EXAMPLE 123
Synthesis of Compound 132

From methyl 3-(2-bromophenyl)-4-nitrobutyrate (105 mg, 0.50 mmol), 3-thiophenecarbaldehyde (0.044 mL, 0.50 mmol) and 3-aminomethylpyridine (0.102 mL, 1.0 mmol), Compound 132 (75 mg, yield 32%) was obtained in the same manner as in Example 1.

$^1$HNMR (CDCl$_3$, 300 MHz) δ8.61 (dd, J=4.2, 1.1 Hz, 1H), 8.26 (d, J=1.1 Hz, 1H), 7.56–7.49 (m, 2H), 7.37 (m, 1H), 7.31–7.11 (m, 5H), 6.94 (d, J=4.0 Hz, 1H), 5.33 (dd, J=10.6, 9.0 Hz, 1H), 5.17–5.06 (m, 2H), 4.37 (m, 1H), 3.95 (d, J=14.8 Hz, 1H), 3.03 (dd, J=17.6, 5.2 Hz, 1H), 2.77 (m, 1H)

EXAMPLE 124
Synthesis of Compound 133

From methyl 3-(2-bromophenyl)-4-nitrobutyrate (105 mg, 0.50 mmol), 3-furaldehyde (0.043 mL, 0.50 mmol) and 3-aminomethylpyridine (0.102 mL, 1.0 mmol), Compound 133 (66 mg, yield 29%) was obtained in the same manner as in Example 1.

$^1$HNMR (CDCl$_3$, 300 MHz) δ8.56 (d, J=3.8 Hz, 1H), 8.35 (br s, 1H), 7.59–7.56 (m, 2H), 7.47 (s, 1H), 7.35–7.27 (m, 4H), 7.17 (m, 1H), 6.32 (s, 1H), 5.52–5.11 (m, 2H), 4.95 (d, J=8.8 Hz, 1H), 4.36 (m, 1H), 4.04 (d, J=15.1 Hz, 1H), 3.05 (dd, J=17.6, 5.3 Hz, 1H), 2.78 (m, 1H)

EXAMPLE 125
Synthesis of Compound 134

From methyl 3-(2-bromophenyl)-4-nitrobutyrate (105 mg, 0.50 mmol), furfural (0.041 mL, 0.5 mmol) and 3-aminomethylpyridine (0.102 mL, 1.0 mmol), Compound 134 (98 mg, yield 43%) was obtained in the same manner as in Example 1.

$^1$HNMR (CDCl$_3$, 300 MHz) δ8.53 (d, J=3.7 Hz, 1H), 8.32 (br s, 1H), 7.59–7.56 (m, 2H), 7.38–7.16 (m, 5H), 7.16 (m, 1H), 6.34–6.30 (m, 2H), 5.52 (dd, J=10.6, 8.6 Hz, 1H), 5.08–4.98 (m, 2H), 4.41 (m, 1H), 4.10 (d, J=15.2 Hz, 1H), 3.01 (dd, J=17.6, 5.1 Hz, 1H), 2.80 (m, 1H)

EXAMPLE 126
Synthesis of Compound 135

From methyl 3-(2-bromophenyl)-4-nitrobutyrate (150 mg, 0.50 mmol), 3-chlorobenzaldehyde (70 mg, 0.50 mmol) and 3-aminomethylpyridine (0.10 mL, 1.0 mmol), Compound 135 (79.4 mg, yield 32%) was obtained in the same manner as in the synthesis of Compound 111.

$^1$HNMR (CDCl$_3$, 300 MHz) δ8.54 (dd, J=4.6, 1.3 Hz, 1H), 8.22 (d, J=2.0 Hz, 1H), 7.55 (br d, J=7.9 Hz, 1H), 7.50 (d, J=7.6 Hz, 1H), 7.39–7.11 (m, 7H), 6.99 (d, J=7.6 Hz, 1H), 5.25 (dd, J=9.9, 10.5 Hz, 1H), 5.17 (d, J=14.8 Hz, 1H), 4.90 (d, J=8.9 Hz, 1H), 4.37 (m, 1H), 3.85 (d, J=14.8 Hz, 1H), 3.07 (dd, J=17.4, 4.2 Hz, 1H), 2.85 (m, 1H)

EXAMPLE 127
Synthesis of Compound 136

From methyl 3-(2-bromophenyl)-4-nitrobutyrate (1.4 g, 4.7 mmol), 3-iodo-4-hydroxybenzaldehyde (1.0 g, 4.7 mmol) and 3-aminomethylpyridine (1.0 mL, 9.4 mmol), Compound 136 (1.7 g, yield 60%) was obtained in the same manner as in the synthesis of Compound 111.

$^1$HNMR (DMSO-d$_6$, 300 MHz) δ10.4 (br s, 1H), 8.36 (d, J=1.7 Hz, 1H), 8.08 (d, J=1.6 Hz, 1H), 7.78 (d, J=7.6 Hz, 1H), 7.71 (d, J=2.0 Hz, 1H), 7.60 (d, J=7.9 Hz, 1H), 7.44 (m, 1H), 7.35 (d, J=7.6 Hz, 1H), 7.22 (d, J=5.0 Hz, 1H), 7.19 (d, J=7.6 Hz, 1H), 7.07 (dd, J=8.4, 2.0 Hz, 1H), 6.68 (d, J=8.4 Hz, 1H), 5.92 (dd, J=11.2, 9.9 Hz, 1H), 4.98 (d, J=9.9 Hz, 1H), 4.38 (d, J=15.2 Hz, 1H), 4.36 (m, 1H), 4.32 (d, J=15.2 Hz, 1H), 2.98 (dd, J=16.8, 13.2 Hz, 1H), 2.73 (dd, J=16.8, 5.0 Hz, 1H)

EXAMPLE 128
Synthesis of Compound 137

From methyl 3-(2-bromophenyl)-4-nitrobutyrate (150 mg, 0.50 mmol), p-tolualdehyde (60 mg, 0.50 mmol) and 3-aminomethylpyridine (0.10 mL, 1.0 mmol), Compound 137 (74 mg, yield 31%) was obtained in the same manner as in the synthesis of Compound 111.

$^1$HNMR (CDCl$_3$, 300 MHz) δ8.53 (d, J=4.6 Hz, 1H), 8.19 (d, J=2.0 Hz, 1H), 7.55 (d, J=7.9 Hz, 1H), 7.50 (d, J=6.3 Hz, 1H), 7.30–7.11 (m, 6H), 6.93–6.95 (m, 2H), 5.28 (dd, J=11.2, 8.9 Hz, 1H), 5.16 (d, J=14.8 Hz, 1H), 4.86 (d, J=8.9 Hz, 1H), 4.38 (m, 1H), 3.85 (d, J=14.8 Hz, 1H), 3.05 (dd, J=17.4, 4.9 Hz, 1H), 2.79 (m, 1H), 2.33 (s, 3H)

EXAMPLE 129
Synthesis of Compound 138

From methyl 3-(2-bromophenyl)-4-nitrobutyrate (150 mg, 0.50 mmol), m-tolualdehyde (60 mg, 0.50 mmol) and 3-aminomethylpyridine (0.10 mL, 1.0 mmol), Compound 138 (50 mg, yield 21%) was obtained in the same manner as in the synthesis of Compound 111.

$^1$HNMR (CDCl$_3$, 300 MHz) δ8.54 (dd, J=5.0, 1.3 Hz, 1H), 8.22 (d, J=2.0 Hz, 1H), 7.56 (d, J=7.9 Hz, 1H), 7.50 (d, J=7.6 Hz, 1H), 7.32–7.11 (m, 6H), 7.04 (d, J=8.2 Hz, 2H), 5.28–5.22 (m, 2H), 4.83 (d, J=8.9 Hz, 1H), 4.37 (m, 1H), 3.77 (d, J=14.8 Hz, 1H), 3.05 (dd, J=17.4, 5.3 Hz, 1H), 2.79 (m, 1H), 2.37 (s, 3H)

EXAMPLE 130
Synthesis of Compound 139

From methyl 3-(2-bromophenyl)-4-nitrobutyrate (150 mg, 0.50 mmol), o-tolualdehyde (60 mg, 0.50 mmol) and 3-aminomethylpyridine (0.10 mL, 1.0 mmol), Compound 139 (44 mg, yield 9.2%) was obtained in the same manner as in the synthesis of Compound 111.

$^1$HNMR (CDCl$_3$, 300 MHz) δ8.53 (dd, J=4.7, 1.6 Hz, 1H), 8.13 (d, J=1.6 Hz, 1H), 7.56 (dd, J=7.9, 1.0 Hz, 1H), 7.46 (d, J=7.9 Hz, 1H), 7.33–7.10 (m, 8H), 5.33–5.20 (m, 2H), 4.51 (m, 2H), 3.73 (d, J=15.2 Hz, 1H), 3.11 (dd, J=17.4, 5.0 Hz, 1H), 2.79 (m, 1H), 1.96 (s, 3H)

EXAMPLE 131
Synthesis of Compound 140

From methyl 3-(2-bromophenyl)-4-nitrobutyrate (15 mg, 0.05 mmol), 2-thiophenecarbaldehyde (4.6 mg, 0.05 mmol) and 3-aminomethylpyridine (0.010 mL, 0.10 mmol), Compound 140 (7.9 mg, yield 35%) was obtained in the same manner as in the synthesis of Compound 111.

$^1$HNMR (CDCl$_3$, 300 MHz) δ8.55 (dd, J=4.8, 1.3 Hz, 1H), 8.32 (d, J=1.9 Hz, 1H), 7.56 (dd, J=7.9, 1.0 Hz, 2H), 7.41 (dd, J=5.2, 0.8 Hz, 1H), 7.33–7.12 (m, 3H), 6.98 (d, J=8.5 Hz, 1H), 6.96 (d, J=3.6 Hz, 1H), 6.91 (dd, J=3.0, 1.0 Hz, 1H), 5.36 (dd, J=10.6, 9.3 Hz, 1H), 5.27–5.22 (m, 2H), 4.36 (m, 1H), 3.98 (d, J=15.2 Hz, 1H), 3.04 (dd, J=17.5, 5.3 Hz, 1H), 2.82 (m, 1H)

EXAMPLE 132
Synthesis of Compound 141

Under an argon atmosphere, triethylamine (0.1 mL), methyl acrylate (0.10 mL) and Compound 136 (62 mg, 0.1 mmol) were added to a solution (1 mL) of palladium (II) diacetate (2.2 mg, 0.01 mmol) and triphenylphosphine (11 mg, 0.04 mmol) in N,N-dimethylformamide, followed by stirring at 55° C. for 1 hour. Next, the reaction solution was filtered through celite, and the solvent contained in the filtrate was evaporated under reduced pressure. The residue was purified by silica gel thin layer chromatography (developed with chloroform/methanol=9/1) to give Compound 141 (37 mg, yield 65%).

$^1$HNMR (CDCl$_3$, 300 MHz) δ8.43 (d, J=4.0 Hz, 1H), 7.89 (br s, 1H), 7.85 (d, J=15.9 Hz, 1H), 7.79 (d, J=8.2 Hz, 1H), 7.56 (d, J=7.9 Hz, 1H), 7.38–7.27 (m, 4H), 7.13 (m, 1H), 6.83 (dd, J=8.5, 1.8 Hz, 1H), 6.74 (d, J=8.5 Hz, 1H), 6.57 (d, J=15.9 Hz, 1H), 5.32 (m, 1H), 4.90 (d, J=14.9 Hz, 1H), 4.79 (d, J=9.6 Hz, 1H), 4.70 (m, 1H), 4.25 (d, J=14.9 Hz, 1H), 3.81 (s, 3H), 3.10 (dd, J=17.4, 5.0 Hz, 1H), 2.86 (br m, 1H)

EXAMPLE 133
Synthesis of Compound 142

Palladium-carbon (5 mg) was added to a solution (3 mL) of Compound 141 (20 mg, 0.035 mmol) in ethyl acetate under a hydrogen atmosphere, followed by stirring at room temperature for 5 hours. Next, the catalyst was removed by filtration through celite, and the solvent was evaporated under reduced pressure. The obtained residue was purified by silica gel thin layer chromatography (chloroform/methanol=9/1) to give Compound 142 (14.3 mg, yield 72%).

$^1$HNMR (CDCl$_3$, 300 MHz) δ8.50 (s, 1H), 8.00 (s, 1H), 7.71 (d, J=7.9 Hz, 1H), 7.56 (d, J=7.9 Hz, 1H), 7.38–7.11 (m, 4H), 6.92 (br s, 1H), 6.80–7.72 (br s, 2H), 5.30 (m, 1H), 5.06 (d, J=14.6 Hz, 1H), 4.75 (d, J=9.2 Hz, 1H), 4.38 (m, 1H), 4.08 (d, J=14.6 Hz, 1H), 3.69 (s, 3H), 3.10–2.82 (m, 4H), 2.66 (t, J=6.9 Hz, 2H)

EXAMPLE 134
Synthesis of Compound 143

From methyl 3-(2-bromophenyl)-4-nitrobutyrate (301 mg, 1.0 mmol), 3,5-dimethyl-4-hydroxybenzaldehyde (150 mg, 1.0 mmol) and 3-aminomethylpyridine (0.2 mL, 2.0 mmol), Compound 143 (127 mg, yield 25%) was obtained in the same manner as in Example 1.

$^1$HNMR (DMSO-d$_6$, 300 MHz) δ8.41(s, 1H), 8.35 (d, J=4.9 Hz, 1H), 8.08 (s, 1H), 7.79 (d, J=6.9 Hz, 1H), 7.60 (d, J=8.3 Hz, 1H), 7.45–7.34 (m, 2H), 7.24–7.18 (m, 2H), 6.85 (s, 2H), 5.85 (dd, J=11.2, 9.9 Hz, 1H), 4.86 (d, J=9.9 Hz,

1H), 4.88–4.20 (m, 3H), 3.01 (dd, J=17.1, 13.2 Hz, 1H), 2.71 (dd, J=17.1, 5.3 Hz, 1H), 2.03 (s, 6H)

EXAMPLE 135

Synthesis of Compound 144

[Step 1]

Under an argon atmosphere, copper iodide (190 mg, 1.0 mmol), 1-octyne (0.55 mL, 5.0 mmol) and 3-iodo-4-methoxymethoxybenzaldehyde (291 mg, 1.0 mmol) were added to a solution (2 mL) of palladium (II) diacetate (11 mg, 0.05 mmol) and triphenylphosphine (52 mg, 0.20 mmol) in methylene chloride, followed by stirring at room temperature for 2 hours. Next, the reaction solution was filtered through celite, and the solvent contained in the filtrate was evaporated under reduced pressure. The residue was purified by silica gel column chromatography (eluted with ethyl acetate/hexane=1/10) to give 3-(1-octyn-1-yl)-4-methoxymethoxybenzaldehyde (124 mg, yield 45%).

$^1$HNMR (CDCl$_3$, 300 MHz) δ9.86 (s, 1H), 7.99 (d, J=2.3 Hz, 1H), 7.74 (dd, J=8.6, 2.3 Hz, 1H), 7.21 (d, J=8.6 Hz, 1H), 5.32 (s, 2H), 3.52 (s, 3H), 2.74 (t, J=7.0 Hz, 2H), 1.66–1.58 (m, 2H), 1.52–1.45 (m, 2H), 1.34–1.31 (m, 4H), 0.91 (t, J=6.7 Hz, 3H) EI-MS (m/z) 274 (M$^+$)

[Step 2]

From methyl 3-(2-bromophenyl)-4-nitrobutyrate (136 mg, 0.45 mmol), the 3-(1-octyn-1-yl)-4-methoxymethoxybenzaldehyde (124 mg, 0.45 mmol) and 3-aminomethylpyridine (0.11 mL, 1.0 mmol), a Compound having a nitropiperidone structure was obtained in the same manner as in the synthesis of Compound 111. This Compound was dissolved in hydrochloric acid (1 mol/L)/methanol (1/1), and the resulting solution was subjected to reaction at 80° C. for 2 hours. The obtained reaction solution was neutralized with a dilute aqueous solution of sodium hydroxide and then extracted with chloroform/methanol (9/1). After the extract was washed with a saturated brine and dried over anhydrous sodium sulfate, the solvent was evaporated under reduced pressure. The residue was purified by silica gel column chromatography (eluted with chloroform/methanol=1/10) to give Compound 144 (11.4 mg, yield 62%).

$^1$HNMR (CDCl$_3$, 300 MHz) δ9.96 (s, 1H), 8.36 (dd, J=5.0, 1.5 Hz, 1H), 8.12 (d, J=1.5 Hz, 1H), 7.77 (d, J=6.0 Hz, 1H), 7.60 (d, J=7.9 Hz, 1H), 7.45–7.40 (m, 2H), 7.29–7.21 (m, 3H), 6.98 (dd, J=8.2, 2.2 Hz, 1H), 6.68 (d, J=5.5 Hz, 1H), 5.90 (dd, J=11.2, 10.0 Hz, 1H), 4.94 (d, J=10.0 Hz, 1H), 4.43–4.29 (m, 2H), 4.14 (d, J=15.8 Hz, 1H), 2.76 (dd, J=17.1, 12.9 Hz, 1H), 2.72 (dd, J=17.1, 5.3 Hz, 1H), 2.38 (t, J=6.8 Hz, 2H), 1.60–1.21 (m, 8H), 0.88 (t, J=6.8 Hz, 3H)

EXAMPLE 136

Synthesis of Compound 145

From methyl 3-(2-bromophenyl)-4-nitrobutyrate (301 mg, 1.0 mmol), 3-formylphenylboric acid (148 mg, 1.0 mmol) and 3-aminomethylpyridine (0.20 mL, 2.0 mmol), Compound 145 (113 mg, yield 22%) was obtained in the same manner as in Example 1.

$^1$HNMR (DMSO-d$_6$, 270 MHz) δ8.36 (d, J=3.3 Hz, 1H), 8.10 (d, J=3.0 Hz, 1H), 8.07 (br s, 1H), 7.79–7.74 (m, 3H), 7.61 (d, J=7.9 Hz, 1H), 7.44–7.35 (m, 4H), 7.26–7.21 (m, 3H), 5.90 (dd, J=11.2, 9.8 Hz, 1H), 5.03 (d, J=9.8 Hz, 1H), 4.51 (d, J=15.8 Hz, 1H), 4.48 (m, 1H), 4.11 (d, J=15.8 Hz, 1H), 3.08 (dd, J=17.1, 12.2 Hz, 1H), 2.76 (d, J=17.1, 5.3 Hz, 1H)

EXAMPLE 137

Synthesis of Compound 146

From methyl 3-(2-ethylphenyl)-4-nitrobutyrate (1.0 g, 4.0 mmol), 4-hydroxybenzaldehyde (488 mg, 4.0 mmol) and 3-aminomethylpyridine (0.82 mL, 8.0 mmol), Compound 146 (1.4 g, yield 82%) was obtained in the same manner as in Example 1.

$^1$HNMR (DMSO-d$_6$, 270 MHz) δ9.58 (s, 1H), 8.38 (br s, 1H), 8.11 (br s, 1H), 7.64 (d, J=7.2 Hz, 1H), 7.39 (d, J=7.9 Hz, 1H), 7.21–7.09 (m, 6H), 6.60 (d, J=6.9 Hz, 2H), 5.79 (dd, J=10.9, 9.9 Hz, 1H), 4.89 (d, J=9.9 Hz, 1H), 4.45 (d, J=14.8 Hz, 1H), 4.20–4.14 (m, 2H), 3.00 (dd, J=16.5, 12.9 Hz, 1H), 2.73–2.60 (m, 3H), 1.13 (t, J=7.2 Hz, 3H)

EXAMPLE 138

Synthesis of Compound 147

Concentrated nitric acid (0.05 mL) was added to a solution (5.0 mL) of Compound 146 in acetic acid, and this solution was subjected to reaction at room temperature for 3 hours. Next, the reaction solution was neutralized with a saturated aqueous solution of sodium bicarbonate and then extracted with chloroform/methanol (9/1). After the extract was washed with a saturated brine and dried over anhydrous sodium sulfate, the solvent was evaporated under reduced pressure. The residue was purified by silica gel thin layer chromatography (developed with chloroform/methanol=1/20) to give Compound 147 (49 mg, yield 51%).

$^1$HNMR (CDCl$_3$, 300 MHz) δ8.50 (d, J=4.3 Hz, 1H), 8.21 (br s, 1H), 7.89 (d, J=2.0 Hz, 1H), 7.53 (d, J=7.9 Hz, 1H), 7.37 (dd, J=7.9, 2.3 Hz, 1H), 7.31–7.12 (m, 6H), 5.19 (dd, J=11.2, 9.5 Hz, 1H), 4.97–4.83 (m, 2H), 4.24–4.07 (m, 2H), 3.06–2.60 (m, 6H), 1.22 (t, J=7.2 Hz, 3H)

EXAMPLE 139

Synthesis of Compound 148

[Step 1]

A solution (1 mol/L, 60 mL) of ethylmagnesium bromide in tetrahydrofuran was added to a solution (200 mL) of 2-bromobenzaldehyde (5.55 g, 3.0 mmol) in tetrahydrofuran under ice-cooling, followed by stirring for 1 hour while gradually heating the mixture to room temperature. Next, the reaction solution was poured into ice water, and this mixture was neutralized with hydrochloric acid (1 mol/L) and then extracted with ethyl acetate. After the extract was washed with a saturated brine and then dried over sodium sulfate, the solvent was evaporated under reduced pressure. The obtained residue was purified by silica gel column chromatography (developed with ethyl acetate/hexane=1/4) to give 1-(2-bromophenyl)-1-propanol (4.5 g, yield 70%).

$^1$HNMR (DMSO-d$_6$, 270 MHz) δ7.52 (dd, J=7.3, 1.6 Hz, 1H), 7.50 (dd, J=7.3, 0.9 Hz, 1H), 7.32 (dt, J=7.3, 0.9 Hz, 1H), 7.11 (dt, J=7.3, 1.6 Hz, 1H), 5.00 (td, J=7.3, 1.1 Hz, 1H), 2.03 (m, 1H), 1.90–1.63 (m, 2H), 1.00 (t, J=7.5 Hz, 3H)

[Step 2]

p-Toluenesulfonic acid (30 mg) was added to a solution (50 mL) of 1-(2-bromophenyl)-1-propanol (5.55 g, 3.0 mmol) in toluene, followed by reflux for 5 hours. Next, the reaction solution was added to a saturated aqueous solution of sodium bicarbonate under ice-cooling to neutralize the reaction solution, and the mixture was then extracted with diethyl ether. After the extract was washed with a saturated brine and then dried over sodium sulfate, the solvent was evaporated under reduced pressure. The obtained residue was purified by silica gel column chromatography (developed with diethyl ether/hexane=1/10) to give 2-((E)-1-propenyl)bromobenzene (4.75 g, yield 100%).

FAB-MS (m/z) 199, 197 (M+H)$^+$ $^1$HNMR (CDCl$_3$, 270 MHz) δ7.50 (dd, J=7.8, 1.1 Hz, 1H), 7.46 (dd, J=7.8, 1.5 Hz, 1H), 7.23 (dt, J=7.8, 1.1 Hz, 1H), 7.04 (dt, J=7.8, 1.6 Hz, 1H), 6.73 (dd, J=15.6, 1.1 Hz, 1H), 6.17 (qd, J=15.6, 1.1 Hz, 1H), 1.91 (dd, J=6.7, 1.8 Hz, 3H)

[Step 3]

Under an argon atmosphere, 2-((E)-1-propenyl) bromobenzene (2.1 g, 11.0 mmol), methyl acrylate (4.5 mL, 50 mmol) and triethylamine (1 mL) were added to a solution (15 mL) of palladium (II) diacetate (11 mg, 0.05 mmol) and tris(2-methylphenyl)phosphine (60 mg, 0.2 mmol) in N,N-dimethylformamide, followed by stirring at 80° C. for 1 hour. Next, the reaction solution was filtered through Florisil, and the solvent contained in the filtrate was evaporated under reduced pressure. The residue was purified by silica gel column chromatography (eluted with ethyl acetate/hexane=1/10) to give methyl 2-((E)-1-propenyl)cinnamate (740 mg, yield 34%).

FAB-MS (m/z) 203 (M+H)$^+$ $^1$HNMR (CDCl$_3$, 270 MHz) δ8.00 (dd, J=16.0, 1.6 Hz, 1H), 7.46 (d, 1H, J=7.7 Hz), 7.39–7.01 (m, 3H), 6.67 (d, J=15.6 Hz, 1H), 6.29 (dd, J=16.0, 1.6 Hz, 1H), 6.05 (dqd, J=15.6, 6.8, 1.6 Hz, 1H), 3.77 (d, J=1.6 Hz, 3H), 1.88 (td, J=4.9, 1.6 Hz, 3H)

[Step 4]

1,8-Diazabicyclo[5.4.0]-7-undecene (0.1 mL) was added to a solution (10 mL) of methyl 2-((E)-1-propenyl) cinnamate (102 mg, 0.50 mmol) in nitromethane, followed by-stirring at room temperature for 3 hours. Next, the reaction solution was added to a saturated aqueous solution of sodium bicarbonate under ice-cooling to neutralize the reaction solution, and the mixture was then extracted with diethyl ether. After the extract was washed with a saturated brine and then dried over sodium sulfate, the solvent was evaporated under reduced pressure. The obtained residue was purified by silica gel column chromatography (developed with diethyl ether/hexane=1/4) to give methyl 3-[2-((E)-1-propenyl)phenyl]-4-nitrobutyrate (52 g, yield 40%).

FAB-MS (m/z) 264 (M+H)$^+$ $^1$HNMR (CDCl$_3$, 270 MHz) δ7.39 (m, 1H), 7.23–7.19 (m, 2H), 7.13 (m, 1H), 6.77 (dd, J=15.4, 1.5 Hz, 1H), 6.08 (dq, J=15.4, 6.6 Hz, 1H), 4.71–4.59 (m, 2H), 4.37 (m, 1H), 3.63 (s, 3H), 2.78 (d, J=7.1 Hz, 2H), 1.94 (dd, J=6.6, 1.7 Hz, 3H)

[Step 5]

From the methyl 3-[2-((E)-1-propenyl)phenyl]-4-nitrobutyrate (2.3 g, 8.7 mmol), 4-hydroxybenzaldehyde (1.1 g, 8.7 mmol) and 3-aminomethylpyridine (1.77 mL, 17.4 mmol), Compound 148 (1.3 g, yield 34%) was obtained in the same manner as for Compound 111.

$^1$HNMR (DMSO-d$_6$, 270 MHz) δ9.50 (br s, 1H), 8.41 (d, J=4.2 Hz, 1H), 8.19 (br s, 1H), 7.65 (d, J=7.5 Hz, 1H), 7.47 (d, J=8.9 Hz, 1H), 7.34–7.12 (m, 6H), 6.88–6.62 (m, 3H), 6.10 (dq, J=15.0, 6.2 Hz, 1H), 5.73 (dd, J=11.0, 10.0 Hz, 1H), 4.78 (d, J=10.0 Hz, 1H), 4.67 (d, J=15.4 Hz, 1H), 4.32 (ddd, J=12.9, 11.0, 4.4 Hz, 1H), 3.99 (d, J=15.4 Hz, 1H), 3.01 (dd, J=17.2, 12.9 Hz, 1H), 2.65 (dd, J=17.2, 4.4 Hz, 1H), 1.89 (d, J=6.2 Hz, 3H)

EXAMPLE 140

Synthesis of Compound 149

[Step 1]

Methanethiol sodium salt (4.0 g, 52 mmol) was added to a solution (70 mL) of 2-bromobenzaldehyde (9.25 g, 50 mmol) in N,N-dimethylformamide, followed by reflux for 2 hours. Next, the reaction solution was added to dilute hydrochloric acid (0.5 mol/L) under ice-cooling to neutralize the reaction solution, and the mixture was then extracted with ethyl acetate. After the extract was washed with a saturated aqueous solution of sodium bicarbonate and with a saturated brine and then dried over sodium sulfate, the solvent was evaporated under reduced pressure. The obtained crude 2-methylthiobenzaldehyde was dissolved in ethyl acetate (30 mL), and methyl triphenylphosphoranylideneacetate (16.7 g, 50 mmol) was added thereto, followed by stirring at room temperature for 12 hours. Thereafter, the solvent was evaporated under reduced pressure, and the residue was powdered with hexane to give methyl o-methylthiocinnamate (5.43 g, yield 51%).

TOF-MS (m/z) 209 (M+H)$^+$ $^1$HNMR (CDCl$_3$, 270 MHz) δ8.18 (d, J=15.8 Hz, 1H), 7.52 (dd, J=7.6, 0.6 Hz, 1H), 7.34–7.30 (m, 2H), 7.21–7.15 (m, 1H), 6.38 (d, J=15.8 Hz, 1H), 3.81 (s, 3H), 2.47 (s, 3H)

[Step 2]

1,8-Diazabicyclo[5.4.0]-7-undecene (1.0 mL) was added to a solution (200 mL) of the methyl o-methylthiocinnamate (5.4 g, 26 mmol) in nitromethane, followed by stirring at room temperature for one day. Next, the reaction solution was added to a saturated aqueous solution of sodium bicarbonate under ice-cooling to neutralize the reaction solution, and the mixture was then extracted with diethyl ether. After the extract was washed with a saturated brine and then dried over sodium sulfate, the solvent was evaporated under reduced pressure to give crude methyl 3-(2-methylthiophenyl)-4-nitrobutyrate (8.6 g, yield 100%).

FAB-MS (m/z) 264 (M+H)$^+$ $^1$HNMR (CDCl$_3$, 270 MHz) δ7.33–7.23 (m, 2H), 7.17–7.13 (m, 2H), 4.75–4.78 (m, 2H), 4.51 (m, 1H), 3.64 (s, 3H), 2.85 (d, J=7.3 Hz, 2H), 2.50 (s, 3H)

[Step 3]

From the methyl 3-(2-methylthiophenyl)-4-nitrobutyrate (2.7 g, 10 mmol), 4-hydroxybenzaldehyde (1.2 g, 10 mmol) and 3-aminomethylpyridine (1.77 mL, 17.4 mmol), Compound 149 (3.27 g, yield 73%) was obtained in the same manner as in Example 1.

$^1$HNMR (DMSO-d$_6$, 270 MHz) δ9.61 (br s, 1H), 8.37 (d, J=4.3 Hz, 1H), 8.10 (br s, 1H), 7.62 (d, J=7.3 Hz, 1H), 7.40–7.11 (m, 7H), 6.62 (d, J=8.3 Hz, 2H), 5.87 (dd, J=10.9, 9.9 Hz, 1H), 4.89 (d, J=9.9 Hz, 1H), 4.38 (d, J=15.5 Hz, 1H), 4.26 (m, 1H), 4.15 (d, J=15.5 Hz, 1H), 2.98 (dd, J=16.8, 12.9 Hz, 1H), 2.68 (dd, J=16.8, 5.0 Hz, 1H), 2.44 (s, 3H)

EXAMPLE 141

Synthesis of Compound 150

From methyl 3-(2-bromophenyl)-4-nitrobutyrate (301 mg, 1.0 mmol), 3-cyanobenzaldehyde (131 mg, 1.0 mmol) and 3-aminomethylpyridine (0.20 mL, 2.0 mmol), Compound 150 (211 mg, yield 43%) was obtained in the same manner as in Example 1.

$^1$HNMR (DMSO-d$_6$, 270 MHz) δ8.56 (d, J=3.6 Hz, 1H), 8.14 (br s, 1H), 7.68 (td, J=7.9, 1.3 Hz, 1H), 7.59–7.45 (m, 4H), 7.38–7.13 (m, 5H), 5.26 (m, 1H), 5.12 (d, J=15.2 Hz, 1H), 4.98 (d, J=8.6 Hz, 1H), 4.40 (m, 1H), 3.92 (d, J=15.2 Hz, 1H), 3.10 (dd, J=17.8, 5.0 Hz, 1H), 2.86 (dd, J=17.8, 13.2 Hz, 1H)

EXAMPLE 142

Synthesis of Compound 151

From methyl 3-(2-bromophenyl)-4-nitrobutyrate (301 mg, 1.0 mmol), sodium 5-formyl-2-furansulfonate (198 mg, 1.0 mmol) and 3-aminomethylpyridine (0.20 mL, 2.0 mmol), Compound 151 (6.6 mg, yield 1.2%) was obtained in the same manner as in Example 1.

$^1$-HNMR (DMSO-d$_6$, 270 MHz) δ8.42 (d, J=4.0 Hz, 1H), 8.39 (br s, 1H), 7.77 (d, J=7.6 Hz, 1H), 7.61 (d, J=7.9 Hz, 1H), 7.52 (d, J=7.9 Hz, 1H), 7.43 (d, J=7.6 Hz, 1H), 7.26–7.20 (m, 2H), 6.45 (d, J=3.3 Hz, 1H), 6.30 (d, J=3.3 Hz, 1H), 5.94 (dd, J=10.9, 8.9 Hz, 1H), 5.34 (d, J=8.9 Hz, 1H), 4.67 (d, J=15.5 Hz, 1H), 4.41 (m, 1H), 4.13 (d, J=15.5 Hz, 1H), 2.97 (dd, J=17.2, 12.9 Hz, 1H), 2.70 (dd, J=17.2, 15.3 Hz, 1H)

EXAMPLE 143
Synthesis of Compound 152

From methyl 3-(2-bromophenyl)-4-nitrobutyrate (301 mg, 1.0 mmol), 5-formyl-2-thiophenecarboxylic acid (155 mg, 1.0 mmol) and 3-aminomethylpyridine (0.20 mL, 2.0 mmol), Compound 152 (120 mg, yield 23%) was obtained in the same manner as in Example 1.

$^1$HNMR (DMSO-$d_6$, 270 MHz) δ8.41 (d, J=3.3 Hz, 1H), 8.27 (br s, 1H), 7.81 (d, J=7.2 Hz, 1H), 7.62 (d, J=6.9 Hz, 1H), 7.51 (d, J=7.6 Hz, 1H), 7.45 (m, 1H), 7.31–7.20 (m, 2H), 7.07 (m, 1H), 6.98 (m, 1H), 5.94 (dd, J=10.5, 9.6 Hz, 1H), 5.35 (d, J=9.6 Hz, 1H), 4.64 (d, J=15.6 Hz, 1H), 4.39 (m, 1H), 4.27 (d, J=15.6 Hz, 1H), 3.03 (dd, J=16.5, 13.0 Hz, 1H), 2.72 (dd, J=16.5, 6.3 Hz, 1H)

Compounds 153 to 231 were synthesized in the same manner as in Example 1.

EXAMPLE 144
Synthesis of Compound 232

Methanesulfonyl chloride (0.008 mL, 0.10 mol) was added to a solution (5 mL) of Compound 110 (25 mg, 0.05 mmol) in N,N-dimethylacetamide, followed by stirring at room temperature for 1 hour. Thereafter, the reaction solution was poured into water and the mixture was extracted with a mixed solvent of chloroform/methanol (9/1). The extract was dried over sodium sulfate and the solvent was evaporated under reduced pressure. The obtained residue was purified by silica gel column chromatography (eluted with chloroform/methanol=20/1) and reprecipitated from diethyl ether/hexane to give Compound 232 (16 mg, yield 55%).

$^1$HNMR (DMSO-$d_6$, 270 MHz) δ8.36 (d, J=3.3 Hz, 1H), 8.08 (s, 1H), 7.78 (d, J=7.5 Hz, 1H), 7.60 (d, J=8.3 Hz, 1H), 7.45–7.39 (m, 2H), 7.24–7.18 (m, 3H), 6.96 (dd, J=8.3, 2.0 Hz, 1H), 6.67 (d, J=8.4 Hz, 1H), 5.89 (dd, J=11.2, 10.0 Hz, 1H), 4.93 (d, J=10.0 Hz, 1H), 4.48 (d, J=15.4 Hz, 1H), 4.37 (m, 1H), 4.21 (d, J=15.4 Hz, 1H), 3.03 (dd, J=16.9, 12.5 Hz, 1H), 2.92 (s, 3H), 2.73 (dd, J=16.9, 5.0 Hz, 1H)

EXAMPLE 145
Synthesis of Compound 233

Acetic acid (1.0 mL) and potassium cyanate (162 mg, 2.0 mmol) were added to a solution (10 ml) of Compound 110 (25 mg, 0.05 mmol) in tetrahydrofuran, followed by stirring at room temperature for 1 hour. Thereafter, the reaction solution was poured into water and the mixture was extracted with a mixed solvent of chloroform/methanol (9/1). The extract was dried over sodium sulfate and the solvent was evaporated under reduced pressure. The obtained residue was purified by silica gel column chromatography (eluted with chloroform/methanol=20/1) and reprecipitated from diethyl ether/hexane to give Compound 233 (10.2 mg, yield 38%).

$^1$HNMR (DMSO-$d_6$, 300 MHz) δ10.2 (br s, 1H), 8.38 (d, J=5.6 Hz, 1H), 8.14 (br s, 1H), 8.01 (s, 1H), 7.84 (s, 1H), 7.78 (d, J=8.9 Hz, 1H), 7.59 (d, J=7.6 Hz, 1H), 7.46–7.37 (m, 2H), 7.27–7.20 (m, 2H), 6.73 (d, J=7.9 Hz, 1H), 6.65 (d, J=7.9 Hz, 1H), 6.22 (br s, 1H), 5.82 (dd, J=11.5, 9.9 Hz, 1H), 4.82 (d, J=9.9 Hz, 1H), 4.62 (d, J=14.8 Hz, 1H), 4.35 (m, 1H), 4.04 (d, J=14.8 Hz, 1H), 3.10 (m, 1H), 2.72 (m, 1H)

EXAMPLE 146
Synthesis of Compound 234

Sodium triacetoxyborohydride (152 mg, 40 mmol) and benzaldehyde (0.02 mL, 2.0 mmol) were added to a solution (20 mL) of Compound 110 (24 mg, 0.05 mmol) in a mixed solvent of chloroform/methanol (9/1) under ice-cooling, followed by stirring at room temperature for 1 hour. Thereafter, the reaction solution was poured into water, and the mixture was washed with dilute hydrochloric acid, neutralized with an aqueous solution of sodium bicarbonate, and extracted with a mixed solvent of chloroform/methanol (9/1). The extract was dried over sodium sulfate and the solvent was evaporated under reduced pressure. The obtained residue was purified by silica gel column chromatography (eluted with chloroform/methanol=98/2) to give Compound 234 (11.4 mg, yield 39%).

$^1$HNMR (CDCl$_3$, 300 MHz) δ8.49 (dd, J=2.6, 1.0 Hz, 1H), 7.92 (br s, 1H), 7.82 (d, J=7.5 Hz, 1H), 7.54 (d, J=7.5 Hz, 1H), 7.40–7.14 (m, 9H), 6.55 (d, J=7.5 Hz, 1H), 6.27 (s, 1H), 6.10 (d, J=7.5 Hz, 1H), 5.15–5.05 (m, 2H), 4.57 (d, J=8.9 Hz, 1H), 4.36–4.21 (m, 3H), 3.90 (m, 1H), 2.97 (m, 1H), 2.66 (m, 1H)

EXAMPLE 147
Synthesis of Compound 235

From methyl 3-(2-methylthiophenyl)-4-nitrobutyrate (269 mg, 1.0 mmol), benzaldehyde (122 mg, 1.0 mmol) and 3-aminomethylpyridine (0.20 mL, 2.0 mmol), Compound 235 (220 mg, yield 51%) was obtained in the same manner as in Example 1.

$^1$HNMR (CDCl$_3$, 270 MHz) δ8.52 (dd, J=4.6, 1.3 Hz, 1H), 8.20 (d, J=2.0 Hz, 1H), 7.53 (dt, J=7.9, 2.0 Hz, 1H), 7.37–7.14 (m, 10H), 5.40 (m, 1H), 5.13 (d, J=14.9 Hz, 1H), 4.91 (d, J=8.9 Hz, 1H), 4.51 (m, 1H), 3.88 (d, J=14.9 Hz, 1H), 3.04 (dd, J=17.5, 5.3 Hz, 1H), 2.85 (m, 1H), 2.44 (s, 3H)

EXAMPLE 148
Synthesis of Compound 236

From methyl 3-(2-bromophenyl)-4-nitrobutyrate (301 mg, 1.0 mmol), 3-pyridinecarbaldehyde (0.094 mL, 1.0 mmol) and 3-aminomethylpyridine (0.20 mL, 2.0 mmol), Compound 236 (370 mg, yield 79%) was obtained in the same manner as in Example 1.

$^1$HNMR (CDCl$_3$, 270 MHz) δ8.67 (dd, J=4.8, 1.7 Hz, 1H), 8.55 (dd, J=4.6, 1.9 Hz, 1H), 8.45 (d, J=1.9 Hz, 1H), 8.21 (d, J=1.7 Hz, 1H), 7.58 (dd, J=7.9, 1.3 Hz, 1H), 7.48–7.44 (m, 2H), 7.32–7.13 (m, 5H), 5.29 (dd, J=10.2, 9.4 Hz, 1H), 5.17 (d, J=15.0 Hz, 1H), 4.97 (d, J=9.4 Hz, 1H), 4.38 (m, 1H), 3.90 (d, J=15.0 Hz, 1H), 3.10 (dd, J=17.6, 5.0 Hz, 1H), 2.68 (m, 1H)

EXAMPLE 149
Synthesis of Compound 6

From methyl 3-(3-bromophenyl)-4-nitrobutyrate (151 mg, 0.5 mmol), 4-cyanobenzaldehyde (66 mg, 0.50 mmol) and 3-aminomethylpyridine (0.10 mL, 1.0 mmol), Compound 6 (28 mg, yield 11%) was obtained in the same manner as in Example 1.

$^1$HNMR (CDCl$_3$, 300 MHz) δ8.59 (br d, J=4.5 Hz, 1H), 8.25 (br s, 1H), 7.80–7.10 (m, 10H), 5.34 (d, J=15.0 Hz, 1H), 5.00–4.80 (m, 2H), 3.70 (m, 1H), 3.64 (d, J=17.0 Hz, 1H), 3.03 (dd, J=17.5, 5.0 Hz, 1H), 2.89 (dd, J=17.5, 13.0 Hz, 1H)

EXAMPLE 150
Synthesis of Compound 8

From methyl 3-(3-bromophenyl)-4-nitrobutyrate (151 mg, 0.50 mmol), 4-carboxybenzaldehyde (75 mg, 0.50 mmol) and 3-aminomethylpyridine (0.10 mL, 1.0 mmol), Compound 8 (22 mg, yield 9%) was obtained in the same manner as in Example 1.

$^1$HNMR (DMSO-$d_6$, 300 MHz) d 8.41 (br d, J=3.5 Hz, 1H), 8.14 (br s, 1H), 7.84–7.20 (m, 10H), 5.81 (dd, J=11.2, 9.9 Hz, 1H), 5.04 (d, J=9.9 Hz, 1H), 4.66 (d, J=15.8 Hz, 1H), 4.03 (m, 1H), 4.02 (d, J=15.8 Hz, 1H), 3.19 (dd, J=17.0, 12.8 Hz, 1H), 2.79 (dd, J=17.0 Hz, 4.6 Hz, 1H)

EXAMPLE 151

Synthesis of Compound 89

D-Camphor-10-sulfonyl chloride (65 mg, 0.30 mmol) and triethylamine (0.068 mL, 0.50 mmol) were added under ice-cooling to a solution (20 mL) of Compound 14 (96 mg, 0.20 mmol) in methylene chloride, followed by stirring at room temperature for 1 hour. After adding water thereto, the reaction solution was extracted with chloroform and the organic layer was dried over sodium sulfate. After evaporating the solvent under reduced pressure, the residue was purified by silica gel column chromatography (eluted with chloroform/methanol=98/2) to give Compound 89 (67 mg, a 1:1 mixture of diastereomers, yield 50%).

Industrial Applicability

The present invention provides 2-piperidone compounds, which have a potent activity of inhibiting the proliferation of tumor cells and thus are useful as medicaments, as well as antitumor agents containing these compounds.

What is claimed is:

1. A 2-piperidone compound represented by the following formula (I) or a pharmaceutically acceptable salt thereof:

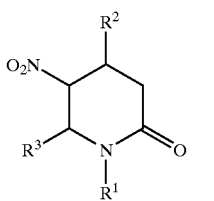

(I)

wherein $R^1$ represents $-(CH_2)_nR^{1a}$ {wherein n is an integer of from 0 to 5, and $R^{1a}$ represents amino, lower alkylamino, di(lower alkyl)amino, substituted or unsubstituted aryl, or a substituted or unsubstituted heterocyclic group}, and $R^2$ and $R^3$ independently represent lower alkyl which may be substituted by lower alkoxycarboyl; lower alkenyl, aralkyl or lower alkynyl which may be substituted by substituted or unsubstituted aryl or a substituted or unsubstituted heterocyclic group; substituted or unsubstituted aryl; or a substituted or unsubstituted heterocyclic group.

2. A 2-piperidone compound as claimed in claim 1 or a pharmaceutically acceptable salt thereof, wherein n is 1.

3. A 2-piperidone compound as claimed in any one of claims 1 to 2 or a pharmaceutically acceptable salt thereof, wherein $R^{1a}$ represents a substituted or unsubstituted heterocyclic group, and $R^2$ and $R^3$ independently represent substituted or unsubstituted aryl.

4. A 2-piperidone compound as claimed in claim 3 or a pharmaceutically acceptable salt thereof, wherein $R^{1a}$ represents a heterocyclic group, and $R^2$ and $R^3$ independently represent substituted aryl.

5. A 2-piperidone compound as claimed in any one of claim 4 or a pharmaceutically acceptable salt thereof, wherein $R^{1a}$ is pyridyl.

6. A pharmaceutical composition which comprises the 2-piperidone compound as claimed in any one of claim 5 or a pharmaceutically acceptable salt thereof.

7. An antitumor agent which comprises the 2-piperidone compound as claimed in any one of claim 5 or a pharmaceutically acceptable salt thereof.

8. A method for preventing or treating a patient having tumor, which comprises administering to the patient an effective amount of any one of the 2-piperidone compounds as claimed in any one of claim 5 or a pharmaceutically acceptable salt thereof.

9. A pharmaceutical composition which comprises a pharmaceutically acceptable carrier and an effective amount of any one of the 2-piperidone compounds as claimed in any one of claim 5 or a pharmaceutically acceptable salt thereof in a pharmaceutically acceptable dosage form.

* * * * *

UNITED STATES PATENT AND TRADEMARK OFFICE
CERTIFICATE OF CORRECTION

PATENT NO. : 6,492,392 B1
DATED : December 10, 2002
INVENTOR(S) : Yutaka Kanda et al.

It is certified that error appears in the above-identified patent and that said Letters Patent is hereby corrected as shown below:

Title page,
Item [56], References Cited, U.S. PATENT DOCUMENTS, insert:
-- 5,672,598    9/1997      De et al.  514/212 --.
OTHER PUBLICATIONS, after Chem. abstr. vol. 122, "Pascaal et al," should read
-- Pascual et al., --; and "Chem Abstr vol. 117," should read -- Chem. Abstr. vol. 117, --
and "Pascal et al," should read -- Pascual et al., --.

Column 51,
Line 36, "2.-92" should read -- 2.92 --.

Column 54,
Line 59, "Compound63" should read -- Compound 63 --.

Column 66,
Line 33, "J 14.1," should read -- J=14.1, --.

Column 76,
Line 60, "$^1$-HNMR" should read -- $^1$HNMR --.

Column 80,
Lines 18, 22, 25 and 30, "any one of" should be deleted;
Line 33, "carrier-and" should read -- carrier and --;
Line 34, "any" should be deleted; and
Line 35, "one of" should be deleted.

Signed and Sealed this

Sixteenth Day of September, 2003

JAMES E. ROGAN
*Director of the United States Patent and Trademark Office*